(12) United States Patent
Loomas et al.

(10) Patent No.: US 9,238,113 B2
(45) Date of Patent: *Jan. 19, 2016

(54) NASAL RESPIRATORY DEVICES FOR POSITIVE END-EXPIRATORY PRESSURE

(75) Inventors: Bryan Loomas, Los Gatos, CA (US); Rajiv Doshi, Los Altos, CA (US); Ryan Kendall Pierce, San Francisco, CA (US); Robert A. Howard, Palo Alto, CA (US); Motohide Hatanaka, Tokyo (JP)

(73) Assignee: Theravent, Inc., San Jose, CA (US)

( * ) Notice: Subject to any disclaimer, the term of this patent is extended or adjusted under 35 U.S.C. 154(b) by 317 days.

This patent is subject to a terminal disclaimer.

(21) Appl. No.: 12/877,836

(22) Filed: Sep. 8, 2010

(65) Prior Publication Data

US 2010/0326447 A1  Dec. 30, 2010

Related U.S. Application Data

(63) Continuation of application No. 11/811,401, filed on Jun. 7, 2007, now Pat. No. 7,806,120, which is a continuation-in-part of application No. 11/298,640, filed on Dec. 8, 2005, now Pat. No. 7,735,492.

(60) Provisional application No. 60/634,715, filed on Dec. 8, 2004, provisional application No. 60/811,814, filed on Jun. 7, 2006.

(51) Int. Cl.
*A61M 15/08* (2006.01)
*A61M 15/00* (2006.01)
*A61M 16/00* (2006.01)

(52) U.S. Cl.
CPC ............ *A61M 15/08* (2013.01); *A61M 15/002* (2014.02); *A61M 2016/003* (2013.01); *A61M 2016/0027* (2013.01); *A61M 2210/0618* (2013.01)

(58) Field of Classification Search
USPC ............ 128/204.21, 204.22, 204.23, 204.24, 128/204.25, 204.26, 204.28, 205.12, 128/205.13, 205.24, 206.11, 207.18
See application file for complete search history.

(56) References Cited

U.S. PATENT DOCUMENTS

| 69,396 A | 10/1867 | Curtis |
| 628,111 A | 7/1899 | McHatton |
| 669,098 A | 3/1901 | Overshiner |
| 675,275 A | 5/1901 | Gunning |

(Continued)

FOREIGN PATENT DOCUMENTS

| EP | 0434258 A2 | 6/1991 |
| EP | 1157663 A1 | 11/2001 |

(Continued)

OTHER PUBLICATIONS

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

(Continued)

*Primary Examiner* — Ophelia A Hawthorne
(74) *Attorney, Agent, or Firm* — Shay Glenn LLP

(57) ABSTRACT

Described herein are nasal respiratory devices, in particular, nasal respiratory devices configured to achieve positive end-expiratory pressure (PEEP) in a subject wearing the device. PEEP devices may have a threshold pressure for opening during expiration. In some variations, these devices have a threshold pressure for closing during expiration.

14 Claims, 38 Drawing Sheets

(56) References Cited

U.S. PATENT DOCUMENTS

| | | | |
|---|---|---|---|
| 718,785 A | 1/1903 | McNary | |
| 746,869 A | 12/1903 | Moulton | |
| 774,446 A | 11/1904 | Moulton | |
| 810,617 A | 1/1906 | Carence | |
| 1,819,884 A | 8/1931 | Fores | |
| 2,198,959 A | 4/1940 | Clarke | |
| 2,237,954 A | 4/1941 | Wilson | |
| 2,264,153 A | 11/1941 | Rowe | |
| 2,274,886 A | 3/1942 | Carroll | |
| 2,282,681 A | 5/1942 | Stotz | |
| 2,335,936 A | 12/1943 | Hanlon | |
| 2,433,565 A | 12/1947 | Korman | |
| 2,448,724 A | 9/1948 | McGovney | |
| 2,593,315 A | 4/1952 | Kraft | |
| 2,672,138 A | 3/1954 | Carlock | |
| 2,751,906 A | 6/1956 | Irvine | |
| 2,777,442 A | 1/1957 | Zelano | |
| 3,145,711 A | 8/1964 | Beber | |
| 3,315,701 A | 4/1967 | Stilwell | |
| 3,370,305 A | 2/1968 | Goott et al. | |
| 3,451,392 A | 6/1969 | Cook et al. | |
| 3,463,149 A | 8/1969 | Albu | |
| 3,513,839 A | 5/1970 | Vacante | |
| 3,556,122 A | 1/1971 | Laerdal | |
| 3,616,802 A | 11/1971 | Marinaccio | |
| 3,657,855 A | 4/1972 | Swezey | |
| 3,695,265 A | 10/1972 | Brevik | |
| 3,710,799 A | 1/1973 | Caballero | |
| 3,722,509 A | 3/1973 | Nebel | |
| 3,747,597 A | 7/1973 | Olivera | |
| 3,802,426 A | 4/1974 | Sakamoto | |
| 3,884,223 A | 5/1975 | Keindl | |
| 3,902,621 A | 9/1975 | Hidding | |
| 4,004,584 A | 1/1977 | Geaney | |
| 4,030,491 A | 6/1977 | Mattila | |
| 4,040,428 A | 8/1977 | Clifford | |
| 4,054,134 A | 10/1977 | Kritzer | |
| 1,062,135 A | 12/1977 | Kritzer | |
| 4,094,316 A | 6/1978 | Nathanson | |
| 4,143,872 A | 3/1979 | Havstad et al. | |
| 4,212,296 A | 7/1980 | Schaar | |
| 4,220,150 A | 9/1980 | King | |
| 4,221,217 A | 9/1980 | Amezcua | |
| 1,226,233 A | 10/1980 | Kritzer | |
| 4,240,420 A | 12/1980 | Riaboy | |
| 4,267,831 A | 5/1981 | Aguilar | |
| 4,325,366 A | 4/1982 | Tabor | |
| 4,327,719 A | 5/1982 | Childers | |
| RE31,040 E | 9/1982 | Possis | |
| 4,354,489 A | 10/1982 | Riaboy | |
| 4,403,616 A | 9/1983 | King | |
| 4,456,016 A | 6/1984 | Nowacki et al. | |
| 4,487,207 A | 12/1984 | Fitz | |
| 4,533,137 A | 8/1985 | Sonne | |
| 4,582,058 A | 4/1986 | Depel et al. | |
| 4,584,997 A | 4/1986 | Delong | |
| 4,601,465 A | 7/1986 | Roy | |
| 4,640,277 A | 2/1987 | Meyer et al. | |
| 4,651,873 A | 3/1987 | Stolcenberg et al. | |
| 4,702,374 A | 10/1987 | Kelner | |
| 4,718,554 A | 1/1988 | Barbato | |
| 4,739,987 A | 4/1988 | Nicholson | |
| 4,759,356 A | 7/1988 | Muir | |
| 4,822,354 A | 4/1989 | Elosegui | |
| 4,854,574 A | 8/1989 | Larson et al. | |
| 4,860,766 A * | 8/1989 | Sackner | 600/561 |
| 4,862,903 A | 9/1989 | Campbell | |
| 4,908,028 A | 3/1990 | Colon et al. | |
| 4,913,138 A | 4/1990 | Yoshida et al. | |
| 4,919,138 A | 4/1990 | Nordenstroom | |
| 4,973,047 A | 11/1990 | Norell | |
| 4,979,505 A | 12/1990 | Cox | |
| 4,984,302 A | 1/1991 | Lincoln | |
| 4,984,581 A | 1/1991 | Stice | |
| 5,016,425 A | 5/1991 | Weick | |
| 5,033,312 A | 7/1991 | Stupecky | |
| 5,038,621 A | 8/1991 | Stupecky | |
| 5,052,400 A * | 10/1991 | Dietz | 600/535 |
| 5,059,208 A | 10/1991 | Coe et al. | |
| 5,074,293 A | 12/1991 | Lott et al. | |
| 5,078,739 A | 1/1992 | Martin | |
| 5,092,781 A | 3/1992 | Casciotti et al. | |
| 5,117,820 A | 6/1992 | Robitaille | |
| 5,197,980 A | 3/1993 | Gorshkov et al. | |
| 5,255,687 A | 10/1993 | McKenna | |
| 5,383,470 A | 1/1995 | Kolbly | |
| 5,385,542 A | 1/1995 | Rawlings | |
| 5,391,205 A | 2/1995 | Knight | |
| 5,392,773 A | 2/1995 | Bertrand | |
| 5,394,867 A | 3/1995 | Swann | |
| 5,414,627 A | 5/1995 | Wada et al. | |
| 5,415,660 A | 5/1995 | Campbell et al. | |
| 5,425,359 A | 6/1995 | Liou | |
| 5,459,544 A | 10/1995 | Emura | |
| 5,522,382 A | 6/1996 | Sullivan et al. | |
| 5,535,739 A | 7/1996 | Rapoport et al. | |
| 5,562,641 A | 10/1996 | Flomenblit et al. | |
| 5,568,808 A | 10/1996 | Rimkus | |
| 5,572,994 A | 11/1996 | Smith | |
| 5,607,469 A | 3/1997 | Frey | |
| 5,649,533 A | 7/1997 | Oren | |
| 5,665,104 A | 9/1997 | Lee | |
| 5,727,546 A | 3/1998 | Clarke et al. | |
| 5,730,122 A * | 3/1998 | Lurie | 128/207.12 |
| 5,740,798 A | 4/1998 | McKinney | |
| 5,743,256 A | 4/1998 | Jalowayski | |
| 5,763,979 A | 6/1998 | Mukherjee et al. | |
| 5,775,335 A | 7/1998 | Seal | |
| 5,782,896 A | 7/1998 | Chen et al. | |
| 5,797,920 A | 8/1998 | Kim | |
| 5,803,121 A | 9/1998 | Estes | |
| 5,823,187 A | 10/1998 | Estes et al. | |
| 5,848,590 A * | 12/1998 | Smith | 128/201.13 |
| 5,865,170 A | 2/1999 | Moles | |
| 5,876,434 A | 3/1999 | Flomenblit et al. | |
| 5,890,998 A | 4/1999 | Hougen | |
| 5,899,832 A | 5/1999 | Hougen | |
| 5,910,071 A | 6/1999 | Hougen | |
| 5,911,756 A | 6/1999 | Debry | |
| 5,947,119 A | 9/1999 | Reznick | |
| 5,954,766 A | 9/1999 | Zadno-Azizi et al. | |
| 5,957,978 A | 9/1999 | Blom | |
| 5,992,006 A | 11/1999 | Datsikas | |
| 6,004,342 A | 12/1999 | Filis | |
| 6,058,932 A | 5/2000 | Hughes | |
| 6,083,141 A | 7/2000 | Hougen | |
| D430,667 S | 9/2000 | Rome | |
| 6,119,690 A | 9/2000 | Pantaleo | |
| 6,165,133 A | 12/2000 | Rapoport et al. | |
| 6,177,482 B1 | 1/2001 | Cinelli et al. | |
| 6,189,532 B1 | 2/2001 | Hely et al. | |
| 6,213,955 B1 | 4/2001 | Karakasoglu et al. | |
| 6,219,997 B1 | 4/2001 | Friberg et al. | |
| 6,258,100 B1 | 7/2001 | Alferness et al. | |
| 6,287,290 B1 | 9/2001 | Perkins et al. | |
| 6,293,951 B1 | 9/2001 | Alferness et al. | |
| 6,311,839 B1 | 11/2001 | Lo | |
| 6,328,038 B1 | 12/2001 | Kessler et al. | |
| 6,369,126 B1 | 4/2002 | Cinelli et al. | |
| 6,398,775 B1 | 6/2002 | Perkins et al. | |
| 6,439,233 B1 | 8/2002 | Geertsema | |
| 6,484,725 B1 | 11/2002 | Chi | |
| 6,500,095 B1 | 12/2002 | Hougen | |
| 6,510,846 B1 | 1/2003 | O'Rourke | |
| 6,527,761 B1 | 3/2003 | Soltesz et al. | |
| 6,561,188 B1 | 5/2003 | Ellis | |
| 6,562,057 B2 | 5/2003 | Santin | |
| 6,568,387 B2 | 5/2003 | Davenport et al. | |
| 6,573,421 B1 | 6/2003 | Lemaire | |
| 6,581,598 B1 | 6/2003 | Foran et al. | |
| 6,585,639 B1 | 7/2003 | Kotmel et al. | |
| 6,592,594 B2 | 7/2003 | Rimbaugh et al. | |
| 6,592,995 B2 | 7/2003 | Topolkaraev et al. | |
| 6,595,215 B2 | 7/2003 | Wood | |

(56) References Cited

U.S. PATENT DOCUMENTS

| | | | |
|---|---|---|---|
| 6,609,516 B2 | 8/2003 | Hollander et al. | |
| 6,626,172 B1 | 9/2003 | Karow et al. | |
| 6,626,179 B1 * | 9/2003 | Pedley | 128/857 |
| 6,631,721 B1 | 10/2003 | Salter et al. | |
| 6,679,264 B1 | 1/2004 | Deem et al. | |
| 6,694,979 B2 | 2/2004 | Deem et al. | |
| 6,722,360 B2 | 4/2004 | Doshi | |
| 6,726,598 B1 | 4/2004 | Jarvis et al. | |
| 6,737,160 B1 | 5/2004 | Full et al. | |
| 6,769,432 B1 | 8/2004 | Keifer | |
| 6,776,162 B2 | 8/2004 | Wood | |
| 6,776,163 B2 | 8/2004 | Dougill et al. | |
| 6,811,538 B2 | 11/2004 | Westbrook et al. | |
| 6,841,716 B1 | 1/2005 | Tsutsumi | |
| 6,848,446 B2 * | 2/2005 | Noble | 128/207.18 |
| 6,863,066 B2 | 3/2005 | Ogle | |
| 6,866,652 B2 | 3/2005 | Bierman | |
| 6,872,439 B2 | 3/2005 | Fearing et al. | |
| 6,913,017 B2 | 7/2005 | Roberts | |
| 6,921,574 B2 | 7/2005 | Cinelli et al. | |
| 6,997,177 B2 | 2/2006 | Wood | |
| 7,011,723 B2 | 3/2006 | Full et al. | |
| 7,013,896 B2 | 3/2006 | Schmidt | |
| 7,047,969 B2 | 5/2006 | Noble | |
| 7,156,098 B2 * | 1/2007 | Dolezal et al. | 128/206.11 |
| 7,175,723 B2 | 2/2007 | Jones et al. | |
| 7,178,524 B2 | 2/2007 | Noble | |
| 7,201,169 B2 | 4/2007 | Wilkie et al. | |
| D542,407 S | 5/2007 | Stallard et al. | |
| 7,263,996 B2 | 9/2007 | Yung Ho | |
| 7,334,581 B2 | 2/2008 | Doshi | |
| D566,834 S | 4/2008 | Barton | |
| 7,422,014 B1 * | 9/2008 | Smith | 128/204.23 |
| 7,506,649 B2 | 3/2009 | Doshi et al. | |
| 7,559,326 B2 * | 7/2009 | Smith et al. | 128/207.12 |
| 7,578,294 B2 | 8/2009 | Pierro et al. | |
| 7,640,934 B2 | 1/2010 | Zollinger et al. | |
| 7,735,491 B2 | 6/2010 | Doshi et al. | |
| 7,735,492 B2 | 6/2010 | Doshi et al. | |
| 7,798,148 B2 | 9/2010 | Doshi et al. | |
| 7,806,120 B2 * | 10/2010 | Loomas et al. | 128/207.18 |
| 7,880,051 B2 | 2/2011 | Madsen et al. | |
| 7,992,566 B2 | 8/2011 | Pflueger et al. | |
| 2001/0051799 A1 | 12/2001 | Ingenito | |
| 2001/0056274 A1 | 12/2001 | Perkins et al. | |
| 2002/0062120 A1 | 5/2002 | Perkins et al. | |
| 2002/0077593 A1 | 6/2002 | Perkins et al. | |
| 2002/0112729 A1 | 8/2002 | DeVore et al. | |
| 2002/0157673 A1 | 10/2002 | Kessler et al. | |
| 2003/0024527 A1 | 2/2003 | Ginn | |
| 2003/0050648 A1 | 3/2003 | Alferness et al. | |
| 2003/0070682 A1 | 4/2003 | Wilson et al. | |
| 2003/0106555 A1 | 6/2003 | Tovey | |
| 2003/0106556 A1 | 6/2003 | Alperovich et al. | |
| 2003/0140925 A1 | 7/2003 | Sapienza et al. | |
| 2003/0149387 A1 | 8/2003 | Barakat et al. | |
| 2003/0154988 A1 | 8/2003 | DeVore et al. | |
| 2003/0158515 A1 | 8/2003 | Gonzalez et al. | |
| 2003/0195552 A1 | 10/2003 | Santin | |
| 2003/0209247 A1 | 11/2003 | O'Rourke | |
| 2004/0016432 A1 | 1/2004 | Genger et al. | |
| 2004/0020489 A1 | 2/2004 | Gillespie et al. | |
| 2004/0020492 A1 | 2/2004 | Dubrul et al. | |
| 2004/0020493 A1 | 2/2004 | Wood | |
| 2004/0055606 A1 | 3/2004 | Hendricksen et al. | |
| 2004/0112379 A1 | 6/2004 | Djupesland | |
| 2004/0123868 A1 | 7/2004 | Rutter | |
| 2004/0149615 A1 | 8/2004 | Eisenbraun | |
| 2004/0254491 A1 | 12/2004 | Ricciardelli | |
| 2004/0261791 A1 | 12/2004 | Horian | |
| 2004/0261798 A1 | 12/2004 | Rimkus | |
| 2005/0010125 A1 | 1/2005 | Joy et al. | |
| 2005/0011524 A1 | 1/2005 | Thomlinson et al. | |
| 2005/0033344 A1 | 2/2005 | Dillard et al. | |
| 2005/0051170 A1 | 3/2005 | Koo | |
| 2005/0066965 A1 | 3/2005 | Cronk et al. | |
| 2005/0133039 A1 | 6/2005 | Wood | |
| 2005/0211250 A1 | 9/2005 | Dolezal et al. | |
| 2005/0279351 A1 | 12/2005 | Lewis et al. | |
| 2005/0284479 A1 | 12/2005 | Schrader et al. | |
| 2006/0000472 A1 | 1/2006 | Fenton | |
| 2006/0016450 A1 | 1/2006 | Pearson et al. | |
| 2006/0085027 A1 | 4/2006 | Santin et al. | |
| 2006/0169285 A1 | 8/2006 | Bovo | |
| 2006/0180149 A1 | 8/2006 | Matarasso | |
| 2006/0266361 A1 | 11/2006 | Hernandez | |
| 2006/0283461 A1 | 12/2006 | Lubke et al. | |
| 2007/0016123 A1 | 1/2007 | Jensen | |
| 2007/0051364 A1 | 3/2007 | Jacobson et al. | |
| 2007/0095349 A1 | 5/2007 | Hansmann et al. | |
| 2007/0175478 A1 | 8/2007 | Brunst | |
| 2007/0227542 A1 | 10/2007 | Kashmakov et al. | |
| 2007/0277832 A1 | 12/2007 | Doshi et al. | |
| 2007/0283962 A1 | 12/2007 | Doshi et al. | |
| 2007/0287976 A1 | 12/2007 | Sherrill | |
| 2008/0023007 A1 | 1/2008 | Dolezal et al. | |
| 2008/0032119 A1 | 2/2008 | Feldhahn et al. | |
| 2008/0041397 A1 | 2/2008 | Hirs | |
| 2008/0053460 A1 | 3/2008 | Wilson | |
| 2008/0087286 A1 | 4/2008 | Jones | |
| 2008/0099021 A1 | 5/2008 | Moore | |
| 2008/0135044 A1 | 6/2008 | Freitag et al. | |
| 2008/0142014 A1 | 6/2008 | Jiang | |
| 2008/0142018 A1 | 6/2008 | Doshi et al. | |
| 2008/0173309 A1 | 7/2008 | Doshi | |
| 2008/0178874 A1 | 7/2008 | Doshi et al. | |
| 2008/0221470 A1 | 9/2008 | Sather et al. | |
| 2009/0050144 A1 | 2/2009 | Pierce et al. | |
| 2009/0145441 A1 | 6/2009 | Doshi et al. | |
| 2009/0145788 A1 | 6/2009 | Doshi et al. | |
| 2009/0188493 A1 | 7/2009 | Doshi et al. | |
| 2009/0194100 A1 | 8/2009 | Minagi | |
| 2009/0194109 A1 | 8/2009 | Doshi et al. | |
| 2009/0241965 A1 | 10/2009 | Sather et al. | |
| 2009/0308398 A1 | 12/2009 | Ferdinand et al. | |
| 2009/0308402 A1 * | 12/2009 | Robitaille | 128/848 |
| 2010/0147308 A1 | 6/2010 | Doshi et al. | |
| 2011/0067709 A1 | 3/2011 | Doshi et al. | |
| 2011/0240032 A1 | 10/2011 | Doshi | |
| 2011/0240038 A1 | 10/2011 | Doshi et al. | |
| 2012/0055488 A1 | 3/2012 | Pierce et al. | |
| 2014/0345623 A1 | 11/2014 | Pierce et al. | |

FOREIGN PATENT DOCUMENTS

| | | |
|---|---|---|
| EP | 1205203 A2 | 5/2002 |
| EP | 1481702 A2 | 12/2004 |
| FR | 2862614 A1 | 5/2005 |
| GB | 2096574 A | 10/1982 |
| GB | 2324729 A | 4/1998 |
| JP | 52-123786 A | 10/1977 |
| JP | 55-122742 U | 9/1980 |
| JP | 58-136345 A | 8/1983 |
| JP | 63-189257 U | 12/1988 |
| JP | 7-47126 | 2/1995 |
| JP | 3059270 U | 3/1999 |
| JP | 2001-299916 A | 10/2001 |
| JP | 2002-153489 A | 5/2002 |
| JP | 2002-219174 A | 8/2002 |
| JP | 2002-345963 A | 12/2002 |
| JP | 2002-345966 | 12/2002 |
| JP | 05/40589 A | 2/2005 |
| JP | 2005-505355 | 2/2005 |
| JP | 2008-136496 | 6/2008 |
| JP | 2008-522763 | 7/2008 |
| RU | 2048820 C1 | 11/1995 |
| SU | 1586709 A1 | 8/1990 |
| WO | WO 90/12614 A1 | 11/1990 |
| WO | WO 93/08777 A1 | 5/1993 |
| WO | WO 95/17220 A1 | 6/1995 |
| WO | WO 95/33520 A1 | 12/1995 |
| WO | WO 98/46310 A2 | 10/1998 |
| WO | WO 99/03395 A1 | 1/1999 |
| WO | WO 00/29066 A1 | 5/2000 |

(56) References Cited

FOREIGN PATENT DOCUMENTS

| WO | WO 00/50121 A1 | 8/2000 |
|---|---|---|
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 0162342 A1 | 8/2001 |
| WO | WO 01/87170 A1 | 11/2001 |
| WO | WO 01/89381 A1 | 11/2001 |
| WO | WO 02/38038 A2 | 5/2002 |
| WO | WO 03/022124 A2 | 3/2003 |
| WO | WO 03/034927 A1 | 5/2003 |
| WO | WO 2004/084998 A1 | 10/2004 |
| WO | WO2005/000805 A2 | 1/2005 |
| WO | WO2006/040585 A1 | 4/2006 |
| WO | WO2007/023607 | 3/2007 |
| WO | WO 2007/129814 A1 | 11/2007 |
| WO | WO 2007/134458 A1 | 11/2007 |
| WO | WO 2007/146133 A2 | 12/2007 |

OTHER PUBLICATIONS http://chinookmed.com/index.cfm/fa/product.display&Product_ID=275; accessed Nov. 28, 2007.

Dillard, D. et al., Evaluation of a novel intra-bronchial valve to produce lung volume reduction, World Congress of Bronchology, Jun. 2002 (figs. 1-4 available upon request).

Hakel et al.; Nasal obturator for velopharyngeal dysfunction in dysarthria: technical report on a one-way valve; Journal of Medical Speech—Language Pathology; vol. 12; No. 4; pp. 155-159; 2004.

Doshi et al.; U.S. Appl. No. 12/884,140 entitled "Sealing nasal devices for use while sleeping," filed Sep. 16, 2010.

Doshi et al.; U.S. Appl. No. 12/884,146 entitled "Nasal devices for use while sleeping," filed Sep. 16, 2010.

Doshi et al.; U.S. Appl. No. 12/884,151 entitled "Nasal devices with respiratory gas source," filed Sep. 16, 2010.

Doshi et al.; U.S. Appl. No. 12/885,359 entitled "Methods of treating a sleeping subject," filed Sep. 17, 2010.

Doshi et al.; U.S. Appl. No. 12/885,366 entitled "Methods of treating a disorder by inhibiting expiration," filed Sep. 17, 2010.

Doshi et al.; U.S. Appl. No. 12/885,370 entitled "Quiet nasal respiratory devices," filed Sep. 17, 2010.

Sather et al.; U.S. Appl. No. 12/941,734 entitled "Nasal devices having a safe failure mode and remotely activatable," filed Nov. 8, 2010.

Favet et al.; U.S. Appl. No. 13/035,524 entitled "Nasal devices including layered nasal devices and delayed resistance adapters for use with nasal devices," filed Feb. 25, 2011.

Lai et al.; U.S. Appl. No. 13/062,888 entitled "Nasal devices, systems and methods," filed Mar. 8, 2011.

Doshi et al.; U.S. Appl. No. 13/212,948 entitled "Packaging and dispensing nasal devices," filed Aug. 18, 2011.

Sather et al.; U.S. Appl. No. 13/117,933 entitled "Layered nasal respiratory devices," filed May 27, 2011.

Doshi et al., U.S. Appl. No. 13/545,865 entitled "Nasal Devices," filed Jul. 10, 2012.

Witt et al.; U.S. Appl. No. 61/141,251 entitled "System, Method, and Respiration Appliance for Supporting the Airway of a Subject," filed Dec. 30, 2008.

Cline et al. U.S. Appl. No. 14/071,582 entitled "Passive Nasal Peep Devices," filed Nov. 4, 2013.

\* cited by examiner

INSPIRATORY        EXPIRATORY
                   WITH PRELOADED
                   PEEP SPRING $(P_1 - P_2) > P_T$

= NOSE TISSUE

= FOAM

= CHASSIS STRUCTURE

FLOPS DOWN DURING INHALATION 3901
3903
3905

NASAL RESPIRATORY DEVICES FOR POSITIVE END-EXPIRATORY PRESSURE

CROSS-REFERENCE TO RELATED APPLICATIONS

This application claims priority as a continuation of U.S. patent application Ser. No. 11/811,401, filed on Jun. 7, 2007, entitled "NASAL RESPIRATORY DEVICES FOR POSITIVE END-EXPIRATORY PRESSURE", now U.S. Pat. No. 7,806,120, which is a continuation-in-part of U.S. patent application Ser. No. 11/298,640, filed on Dec. 8, 2005, entitled "NASAL RESPIRATORY DEVICES", now U.S. Pat. No. 7,735,492, which claims priority to U.S. Provisional Patent Application No. 60/634,715, filed on Dec. 8, 2004, which are herein incorporated by reference. U.S. patent application Ser. No. 11/811,401 also claims priority to U.S. Provisional Patent Application 60/811,814, filed Jun. 7, 2006, entitled "RESPIRATORY DEVICES") and is herein incorporated by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Positive end-expiratory pressure (PEEP) refers to pressure in the airway at the end of expiration that exceeds atmospheric pressure. Positive end-expiratory pressure has been used clinically mainly as a way to recruit or stabilize lung units and improve oxygenation in patients with hypoxemic respiratory failure. Traditionally, PEEP has been achieved using devices that apply continuous positive airway pressure (referred to as ventilators or CPAP devices), wherein both the inspiratory and expiratory portions of the circuit are pressurized above atmospheric pressure. However, CPAP devices (including modified devices such as "C-FLEX" devices manufactured by Respironics) are expensive, uncomfortable and cumbersome, leading to limited application and patient compliance.

Numerous disease states may benefit from the modification of patient respiration to induce PEEP, including heart failure, sleep apnea and other sleep disorders, hypertension, snoring, chronic obstructive pulmonary disease (COPD), bronchitis, asthma, and many others.

Heart failure, or congestive heart failure (CHF), is a common clinical syndrome that represents the end-stage of a number of pulmonary and cardiac disease states. Heart failure is a degenerative condition that occurs when the heart muscle weakens and the ventricle no longer contracts normally. The heart can then no longer adequately pump blood to the body including the lungs. This may lead to exercise intolerance, or may cause fluid retention with subsequent shortness of breath or swelling of the feet. Over four million people are diagnosed with heart failure in the United States alone. Morbidity and mortality in patients with heart failure is high.

Sleep apnea is defined as the temporary absence or cessation of breathing during sleep. Airflow must be absent for some period of time longer than the usual inter-breath interval, typically defined as ten seconds for adults and eight seconds (or more than two times the normal respiratory cycle time) for infants. There are different varieties of sleep apnea, including central, obstructive, complex, and mixed. In central sleep apnea, the patient makes no effort to breathe. In obstructive apnea, ventilatory effort is present, but no airflow results, because of upper airway closure. In mixed apnea, there is initially no ventilatory effort (suggestive of central sleep apnea), but an obstructive sleep apnea pattern becomes evident when ventilatory effort resumes. Finally, hypopnea is a temporary decrease in inspiratory airflow relative to the previous several inspirations. The terms sleep apnea and/or sleep disordered breathing may refer to hypopnea.

Hypertension refers to elevated blood pressure, and is a very common disease. Hypertension is characterized by elevated systolic and/or diastolic blood pressures. Despite the prevalence of hypertension and its associated complications, control of the disease is far from adequate. Only a third of people with hypertension control their blood pressure adequately. This failure reflects the inherent problem of maintaining long-term therapy for a usually asymptomatic condition, particularly when the therapy may interfere with the patient's quality of life, and when the immediate benefits of the therapy are not obvious to the patient.

Chronic obstructive pulmonary disease (COPD) includes chronic bronchitis, emphysema and asthma. In both chronic bronchitis and emphysema, airflow obstruction limits the patient's airflow during exhalation. COPD is a progressive disease characterized by a worsening baseline respiratory status over a period of many years with sporadic exacerbations often requiring hospitalization. Early symptoms include increased sputum production and sporadic acute exacerbations characterized by increased cough, purulent sputum, wheezing, dyspnea, and fever. As the disease progresses, the acute exacerbations become more frequent. Late in the course of the disease, the patient may develop hypercapnia, hypoxemia, erythrocytosis, cor pulmonale with right-sided heart failure, and edema.

Chronic bronchitis is characterized by a chronic cough with sputum production leading to obstructed expiration. Pathologically, there may be mucosal and submucosal edema and inflammation and an increase in the number and size of mucus glands. Emphysema is characterized by destruction of the lung parenchyma leading to loss of elastic recoil, reduced tethering of airways, and obstruction to expiration. Pathologically, the distal airspaces are enlarged.

Asthma is another chronic lung condition, characterized by difficulty in breathing. People with asthma have extra-sensitive or hyper-responsive airways. The airways react by obstructing or narrowing when they become inflamed or irritated. This makes it difficult for the air to move in and out of the airways, leading to respiratory distress. This narrowing or obstruction can lead to coughing, wheezing, shortness of breath, and/or chest tightness. In some cases, asthma may be life threatening.

In all of these diseases, current medical and surgical therapies are not completely effective, and there is considerable room for improvement. Two therapies that are used to treat these diseases are pulmonary rehabilitation (including pursed-lip breathing) and non-invasive mechanical ventilation.

Pulmonary rehabilitation is frequently used to treat patients suffering from a variety of medical ailments such as those mentioned. For example, COPD patients are taught new breathing techniques that reduce hyperinflation of the lungs and relieve expiratory airflow obstruction. One of the goals of this training is to reduce the level of dyspnea. Typically, these new breathing techniques include diaphragmatic and pursed-lip breathing. Pursed-lip breathing involves inhaling slowly through the nose and exhaling through pursed-lips (as if one were whistling), taking two or three times as long to exhale as to inhale. Most COPD patients instinctively learn how to perform pursed-lip breathing in order to relieve their dyspnea. Moreover, patients with asthma and other respiratory ailments, and even normal people during exercise, have been shown to use pursed-lip breathing, especially during times of exertion.

It is widely believed that producing a proximal obstruction (e.g., pursing the lips) splints open the distal airways that have lost their tethering in certain disease states. In other words, airways that would normally collapse during respiration remain open when the patient breathes through pursed-lips. Moreover, by increasing exhalation time, respiratory rate can be reduced and, in some cases, made more regular.

The medical literature has confirmed the utility of pursed-lip breathing in COPD patients. Specifically, it has been found that pursed-lip breathing by COPD patients results in a reduction in respiratory rate, an increase in tidal volumes, and an improvement of oxygen saturation. All of these effects contribute to a reduction in patient dyspnea. However, pursed-lip breathing requires conscious effort. Thus, the patient cannot breathe through pursed-lips while sleeping. As a result, the patient can still become hypoxic at night and may develop pulmonary hypertension and other sequelae as a result. Furthermore, the patient has to constantly regulate his own breathing. This interferes with his performing of other activities because the patient must pay attention to maintaining pursed-lip breathing.

Non-invasive positive pressure ventilation (NPPV) is another method of treating diseases that benefit from regulation of the patient's respiration. NPPV refers to ventilation delivered by a nasal mask, nasal prongs/pillows or face mask. NPPV eliminates the need for intubation or tracheostomy. Outpatient methods of delivering NPPV include bilevel positive airway pressure (BIPAP or bilevel) ventilator devices, or continuous positive airway pressure (CPAP) devices.

NPPV can deliver a set pressure during each respiratory cycle, with the possibility of additional inspiratory pressure support in the case of bi-level devices. NPPV has been shown to be very efficacious in such diseases as sleep apnea, heart failure, and COPD, and has become increasingly used in recent years. Many patients use CPAP or BIPAP at night while they are sleeping.

However, most patients experience difficulty adapting to nocturnal NPPV, leading to poor compliance. Mask discomfort is a very common problem for patients new to NPPV, because of the high pressures on the nose, mouth, and face, and because of uncomfortably tight straps. Nasal congestion and dryness are also common complaints that may vary by season. The nasal bridge can become red or ulcerated due to excessive mask tension. Eye irritation and acne can also result. Still other patients experience abdominal distention and flatulence. Finally, air leakage through the mouth is also very common in nasal NPPV patients, potentially leading to sleep arousals.

Both pursed-lip breathing and the use of NPPV have been shown to offer significant clinical benefits to patients with a variety of medical illnesses, including but not limited to COPD, heart failure, pulmonary edema, sleep apnea (both central and obstructive) and other sleep disordered breathing, cystic fibrosis, asthma, cardiac valve disease, arrhythmias, anxiety, and snoring. Expiratory resistance is believed to provide the bulk of clinical improvements when using pursed-lip breathing and NPPV, through a variety of physiologic mechanisms. In contrast, inspiratory support is not believed to offer clinical benefits in many patients. For example, in COPD, expiratory resistance facilitates expiration, increases tidal volume, decreases respiratory rate, and improves gas exchange. In the case of heart failure, it is felt that positive pressure in the airways (due to expiratory resistance) reduces pulmonary edema and improves lung compliance, decreases preload and afterload, increases $pO_2$, and decreases $pCO_2$. In many disease states, expiratory resistance helps maintain a more stable respiratory rate that can have profound clinical effects to the patient.

It would therefore be desirable to have a medical device and/or procedure that mimics the effect of pursed-lip breathing and/or the benefits of non-invasive ventilation without suffering from the drawbacks described above.

SUMMARY OF THE INVENTION

Described herein are nasal respiratory devices and methods for treating a variety of medical diseases through the use of such devices.

For example, described herein are nasal respiratory devices for inducing positive end-expiratory pressure adapted to be secured (e.g., removably secured) in communication with a nasal cavity. These devices may include a passageway, and an airflow resistor in communication with the passageway, wherein the airflow resistor is configured to have a non-zero threshold pressure for opening during expiration so that the airflow resistor is closed during expiration when the pressure across the airflow resistor is below the threshold pressure for opening, but the airflow resistor opens during expiration when the airflow resistor exceeds the threshold pressure for opening during expiration. These devices may also include a holdfast configured to secure the airflow resistor in communication with the nasal cavity without covering the subject's mouth.

As described in more detail herein, any appropriate threshold pressure for opening during expiration may be used. For example, the threshold pressure for opening (which may also be referred to as the threshold for opening) of the airflow resistor may be less than about 20 cm $H_2O$, less than about 15 cm $H_2O$, less than about 10 cm $H_2O$, less than about 8 cm $H_2O$, more than about 4 cm $H_2O$, or between a range of pressures. For example, the threshold pressure for opening may be between about 0.5 cm $H_2O$ and about 20 cm $H_2O$, or between about 0.5 cm $H_2O$ and about 15 cm $H_2O$, or between about 4 cm $H_2O$ and about 20 cm $H_2O$. The threshold for opening is typically much less than the pressure resulting from coughing, sneezing, or the like.

In some variations, the airflow resistor may further comprise a non-zero threshold pressure for closing during expiration, such that the airflow resistor closes during expiration when the pressure across the airflow resistor falls below the threshold pressure for closing. Any appropriate threshold pressure for closing during expiration may be used. For example, the threshold pressure for closing during expiration may be greater than about 1 cm $H_2O$, greater than about 2 cm $H_2O$, greater than about 3 cm $H_2O$, greater than about 4 cm $H_2O$, greater than about 10 cm $H_2O$, etc. In some variations, the threshold pressure for closing during expiration is between a range of values, such as between about 0.5 cm $H_2O$ and about 20 cm $H_2O$, between about 0.5 cm $H_2O$ and about 15 cm $H_2O$, between about 0.5 cm $H_2O$ and about 10 cm $H_2O$, between about 0.5 cm $H_2O$ and about 5 cm $H_2O$. The threshold pressure for closing during expiration may be approximately the same as the threshold pressure for opening during expiration, or it may be different.

In some variations the airflow resistor of the device has a threshold pressure for opening that is less than the threshold pressure for closing. In this variation, the device opens when the pressure exceeds the threshold for opening (e.g., at 4 cm $H_2O$), and then closes at a predetermined time after opening after which the pressure must reach a second threshold for opening (e.g., at 10 cm $H_2O$). This may allow a user to breathe out easily at first (possibly improving tolerance for the device) and then have a larger PEEP pressure at the end of expiration.

Also described herein are nasal respiratory devices for inducing positive end-expiratory pressure adapted to be secured in communication with a nasal cavity including a passageway and an airflow resistor in communication with the passageway, wherein the airflow resistor comprises a biased valve having a non-zero threshold pressure for opening during expiration, so that the airflow resistor is closed during expiration when the pressure across the valve is below the threshold pressure for opening, but the valve opens during expiration when the pressure across the valve exceeds the threshold pressure for opening during expiration. These devices may also include a holdfast configured to secure the airflow resistor only in communication with a nasal cavity, or with both nasal cavities (e.g., but not the mouth).

In some variations, the airflow resistor of this device includes a second valve. Any appropriate valves may be used as part of the airflow resistor. These devices are described in greater detail below, but include biased valves configured as a nested valve, bistable valves, and the like.

Also described herein are nasal respiratory devices for inducing positive end-expiratory pressure adapted to be secured in communication with a nasal cavity that include a passageway and an airflow resistor in communication with the passageway, where the airflow resistor has a first valve configured to open during inspiration and close during expiration and a second valve configured to open during exhalation and close during inspiration, and the second valve is configured so that it does not open until the pressure across the second valve exceeds a non-zero threshold pressure for opening. These devices may also include a holdfast configured to secure the airflow resistor in communication with the nasal cavity.

In some variations, the second valve is nested with the first valve. The first valve or the second valve (or both) may be a may be a flap valve. The second valve may be a biased valve (including but not limited to a biased flap valve). The second valve may be a bistable valve.

Also described herein are nasal respiratory devices for inducing positive end-expiratory pressure adapted to be secured in communication with a nasal cavity. These devices may include a first passageway and a second passageway, and an airflow resistor comprising a first valve in communication with the first passageway and a second valve in communication with the second passageway, wherein the first valve is configured to open during inspiration and close during expiration and the second valve is configured to close during inspiration and open during expiration when the pressure across the second valve exceeds a non-zero threshold pressure for opening. These devices may also include a holdfast configured to secure the first and second passageways in communication with the nasal cavity. As mentioned above, the first valve or the second valve (or both) may be a may be a flap valve. The second valve may be a biased valve (including but not limited to a biased flap valve). The second valve may be a bistable valve.

Also described herein are methods of treating a disorder. These methods may include the steps of securing a nasal respiratory device in communication with a subject's nasal cavity without covering the subject's mouth, wherein the respiratory device comprises an airflow resistor configured to have a non-zero threshold pressure for opening during expiration so that the airflow resistor is closed during expiration when the pressure across the valve is below the threshold pressure for opening, but the airflow resistor opens during expiration when the pressure across the airflow resistor exceeds the threshold pressure for opening during expiration, and allowing the subject to breathe at least partly through the nasal respiratory device. The disorder treated may be selected from the group consisting of: respiratory disorders, sleep disorders, gastroenterologic disorders, and cardiovascular disorders.

As described herein, the nasal respiratory device may be secured at least partially within the subject's nasal cavity (e.g., by a compressible holdfast). In some variations, a nasal respiratory device may be secured at least partially over the subject's nasal cavity (e.g., by an adhesive holdfast).

INCORPORATION BY REFERENCE

All publications and patent applications mentioned in this specification are herein incorporated by reference in their entirety to the same extent as if each individual publication or patent application was specifically and individually indicated to be incorporated by reference.

DETAILED DESCRIPTION

Figure 1:
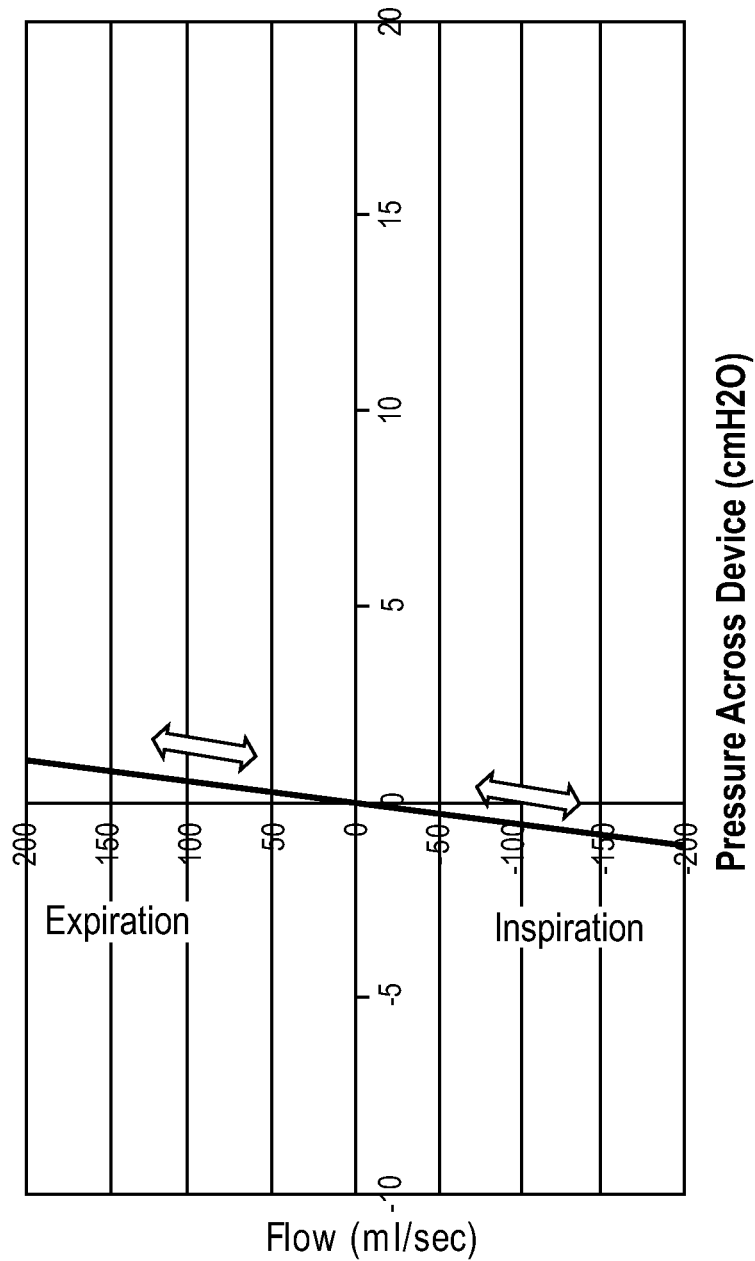
FIG. 1 shows a representative resistive profile through a hollow tubular body.

Described here are respiratory devices, kits, and methods for their use in improving respiratory and cardiovascular function. In particular, respiratory devices for creating positive end expiratory pressure during respiration (PEEP) effect in a subject wearing the device are described. These respiratory devices are referred to as respiratory devices or simply as "devices." The devices and methods described herein may be useful to treat a variety of medical disease states, and may also be useful for non-therapeutic purposes. The devices and methods described herein are not limited to the particular embodiments described. Variations of the particular embodiments described may be made and still fall within the scope of the appended claims. It is also to be understood that the examples and particular embodiments described are not intended to be limiting.

As used in this specification, the singular forms "a," "an," and "the" include plural reference unless the context clearly dictates otherwise. Unless defined otherwise, all technical and scientific terms used herein have the same meaning as commonly understood by one of ordinary skill in the art.

The following descriptions including various design parameters or goals, and methods and devices which fit the design parameters or goals. The devices and methods described herein (and recited by any claims) are not limited to any particular theory of operation.

The devices for achieving PEEP described herein typically include: one or more passageways through which air may pass to enter or exit a respiratory orifice; a holdfast for securing the device to, at least partially over, and/or at least partially within a subject's respiratory orifice; and an airflow resistor, or airflow resistors, for regulating the passage of air through the passageway(s) to achieve PEEP. Furthermore, these devices (and methods for using them to achieve PEEP) typically do not require the application of an external pressure (e.g., from a continuous pressure source such as a pump), but operate only upon pressure generated by the subject wearing the device. Further, these devices and methods for using them may be easy to use, and may be removable and insertable by user without special tools. The devices are typically reliable, and may be small and inexpensive to manufacture.

In operation, a device configured as a PEEP device (or PEEP valve) offers only minimal resistance to inhalation, but has a very high resistance during low pressure exhalation up to a threshold pressure, and a lower resistance to exhalation above that threshold pressure. As described in greater detail below, the devices for achieving PEEP described herein may have a characteristic resistance profile.

Resistance Profiles of PEEP Devices

As used herein, the resistance profile of a device refers to the relationship between pressure across the device, and flow of air through the device. The resistance profile of a device is influenced by the shape and size of the passage(s) through the device, but it may be primarily influenced by the operation of the airflow resistor (or airflow resistors). As described in more detail below, an airflow resistor may include one or more valve or valves. Thus, in the descriptions that follow, an airflow resistor may be referred to as a valve for simplicity. However, the airflow resistors may include additional components in addition to the valve, and may also include multiple valves as part of a single airflow resistor. Thus, an airflow resistor may be referred to as a valve.

In general, a nasal respiratory device including an airflow resistor has a resistance profile to expiration and inspiration. For example, FIG. 1 shows a typical resistance profile for a tubular body (e.g., a passageway) without a valve present. By convention, the x-axis of a resistance profile shows the pressure across the device (in cm of $H_2O$). Pressure may also be represented as the pressure difference between the subject's respiratory system (e.g., oral cavity, nasal cavity, upper respiratory tract, etc.) and the external atmosphere (atmosphere). The y-axis shows the flow through the device (ml/sec). For the sake of simplicity, the devices described by these resistance profiles are assumed to be oriented so that inspiration results in negative flow (e.g., from the proximal to the distal end of the device) and expiration results in flow in the positive direction (e.g., from the distal to the proximal end of the device). Thus, in all of the resistance profiles shown, inspiration (or inhalation) is represented by negative flow through the device, and expiration (or exhalation) is represented by positive flow through the device. As would be apparent to one of skill in the art, the orientation of the device may be switched so that the relative inspiratory and expiratory resistances may be reversed.

The resistance of the device is a function of flow/pressure, as indicated by FIGS. 1-7. For simplicity, this resistance is often referred to as the resistance of the valve.

In all of the resistance profiles described below, the pressure is expressed as pressure in cm of $H_2O$ (or "cm $H_2O$"). A positive pressure occurs when the pressure on the side of the device fluidly connected with the inside of a subject's respiratory tract (e.g., within the nasal or oral cavity) is greater than the atmospheric pressure. A negative pressure occurs when the subject's respiratory tract pressure (e.g., intranasal or intraoral pressure) is below atmospheric pressure. For ease of explanation, the resistance profiles illustrate pressure-flow characteristics showing linear behaviors (e.g., constant slopes).

In the resistance profile shown in FIG. 1 for a device without an airflow resistor, the resistance through the passageway of the device is constant, shown as a straight line passing through the origin. Thus, for this low resistance device, as pressure increases, flow increases precipitously. The pressure-flow profile for a tubular member without a valve (or other airflow resistor) has a steep slope across both inhalation and exhalation. The slope would be infinite (e.g., vertical) showing zero resistance to flow, but because there is a finite passage size for air passage, there will always be some discernable resistance.

Figure 2:
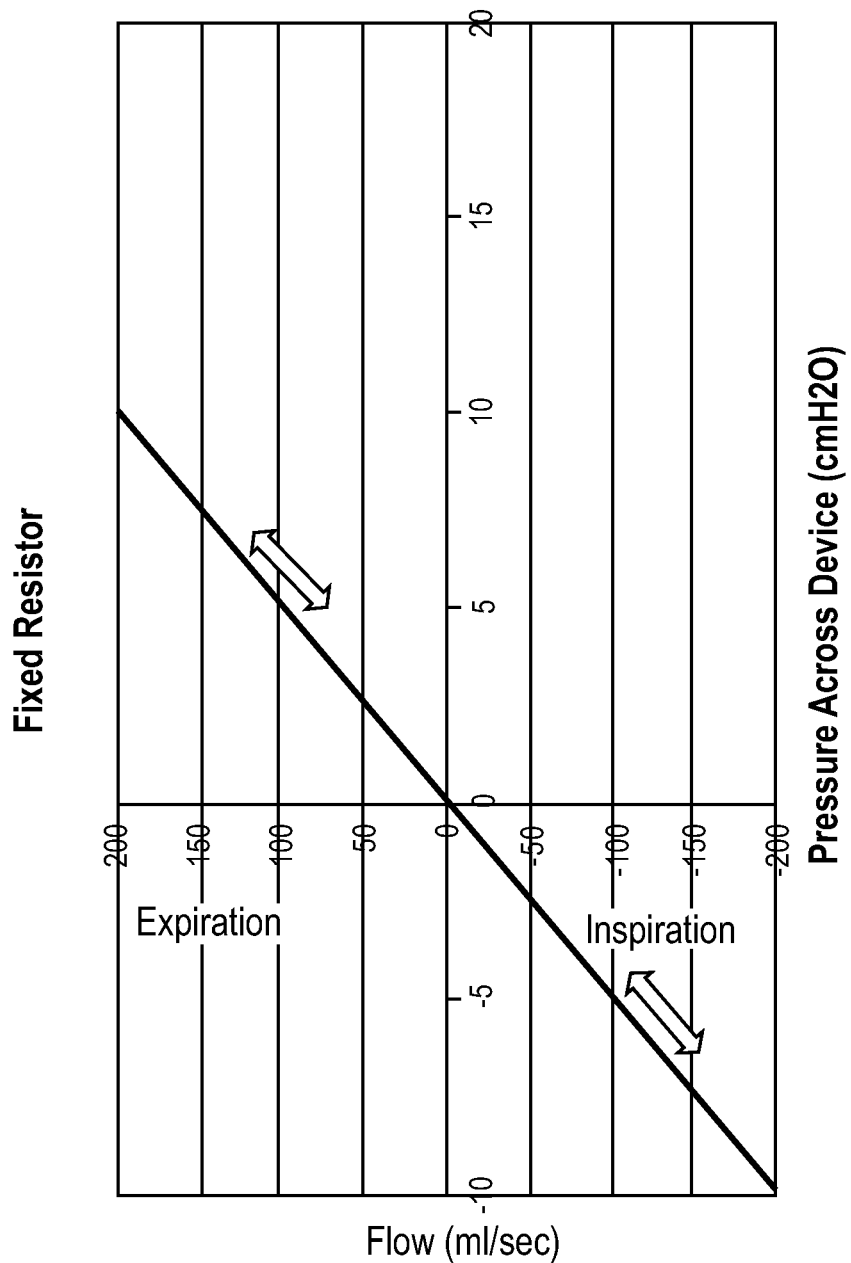
FIG. 2 shows a representative resistive profile through a hollow tubular body having a fixed resistor.

FIG. 2 shows the effect of a simple airflow resistor within the passageway. A fixed resistor such a hole that limits the size of the passageway changes the resistance, which is reflected by a decrease in the slope from the unblocked condition shown in FIG. 1. In FIG. 2, the slope has decreased (reflecting an increase in resistance) over both inhalation and exhalation, since airflow is equally impeded in either direction. The resistance is constant over the range of pressures shown for inhalation and exhalation. Thus, increasing or decreasing pressure across the device (shown by the open arrows) results in a constant rate of change (slope).

A. Simple Differential Resistance

Figure 3:
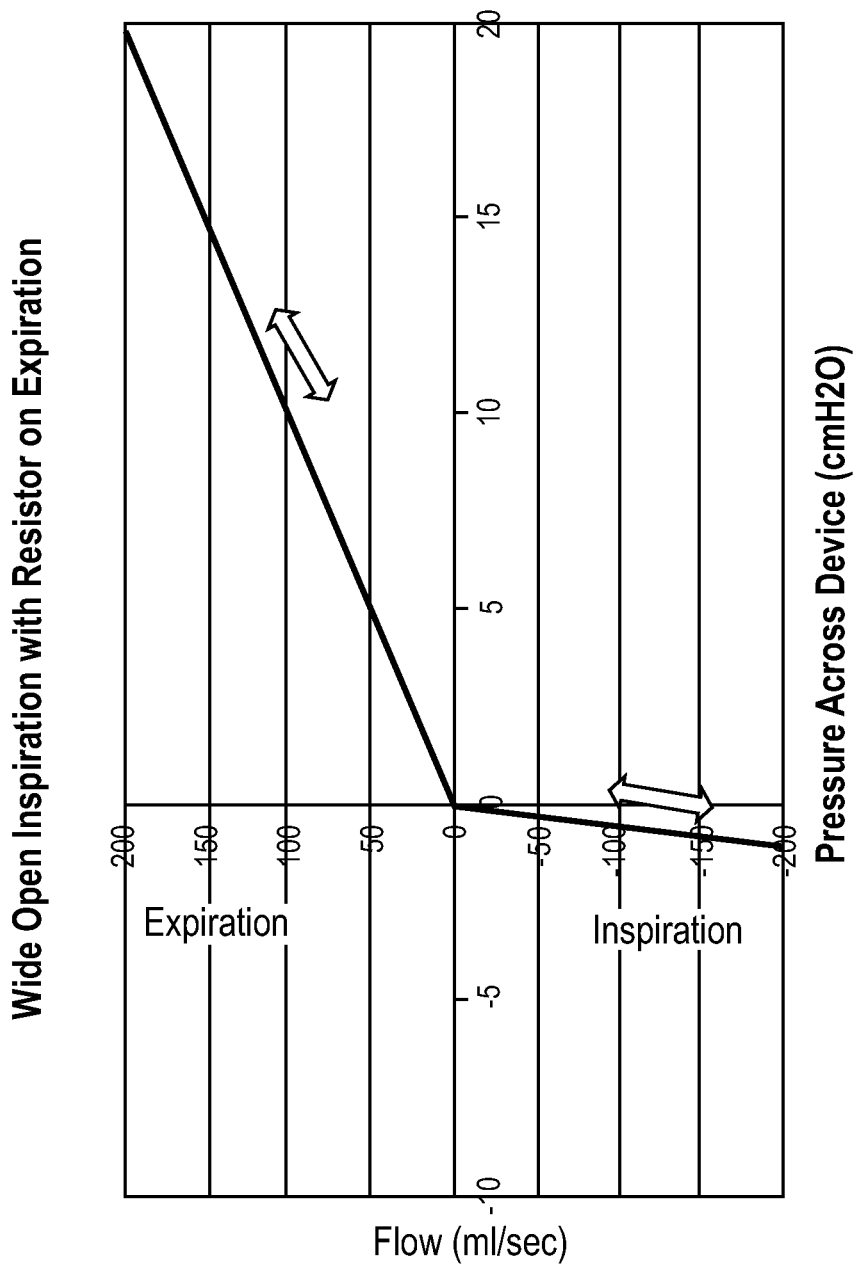
FIG. 3 shows a representative resistive profile for a simple differential resistor device.

An airflow resistor may restrict the airflow within the passageway more in one direction than another. FIG. 3 shows a resistance profile for a device having a simple "differential resistance" airflow resistor. A differential resistance device has a different resistance to airflow through the device at different parts of the respiratory cycle. As used herein, a simple differential resistance device is a particular type of differential resistive device. In general, a simple differential resistive device has a substantially constant, low resistance to airflow during inhalation, and a substantially constant but higher resistance to airflow during expiration.

Thus, a simple differential resistance device has a different resistance for inhalation than for exhalation. FIG. 3 shows a resistance profile for one example of a simple differential resistance device. This device has a low (but constant) resistance for inhalation, as shown by the steep linear slope during negative pressures, and a higher (but constant) resistance during exhalation, as shown by the flatter linear slope during positive pressures. Respiration through this device switches from inhalation to exhalation at the zero pressure point.

Simple differential resistance valves are described in detail in U.S. patent application Ser. No. 11/298,640, filed Dec. 8, 2005, herein incorporated by reference in its entirety. Exemplary respiratory devices include simple flap valves (having one or more flaps); hingeless valves; stopper-type valves; membrane-type valves; ball valves; balloon-type valves; duck-bill valves, umbrella valves, and the like, in which the valve is open during inhalation, but closed (or at least partially closed) during exhalation, and may include one or more leak passageways through which air may pass.

Other types of differential resistance devices may have different resistance profiles. In particular, a respiratory device may have different resistances at different pressures during expiration.

B. Differential Resistance Devices with Threshold for Opening During Expiration

Figure 4:
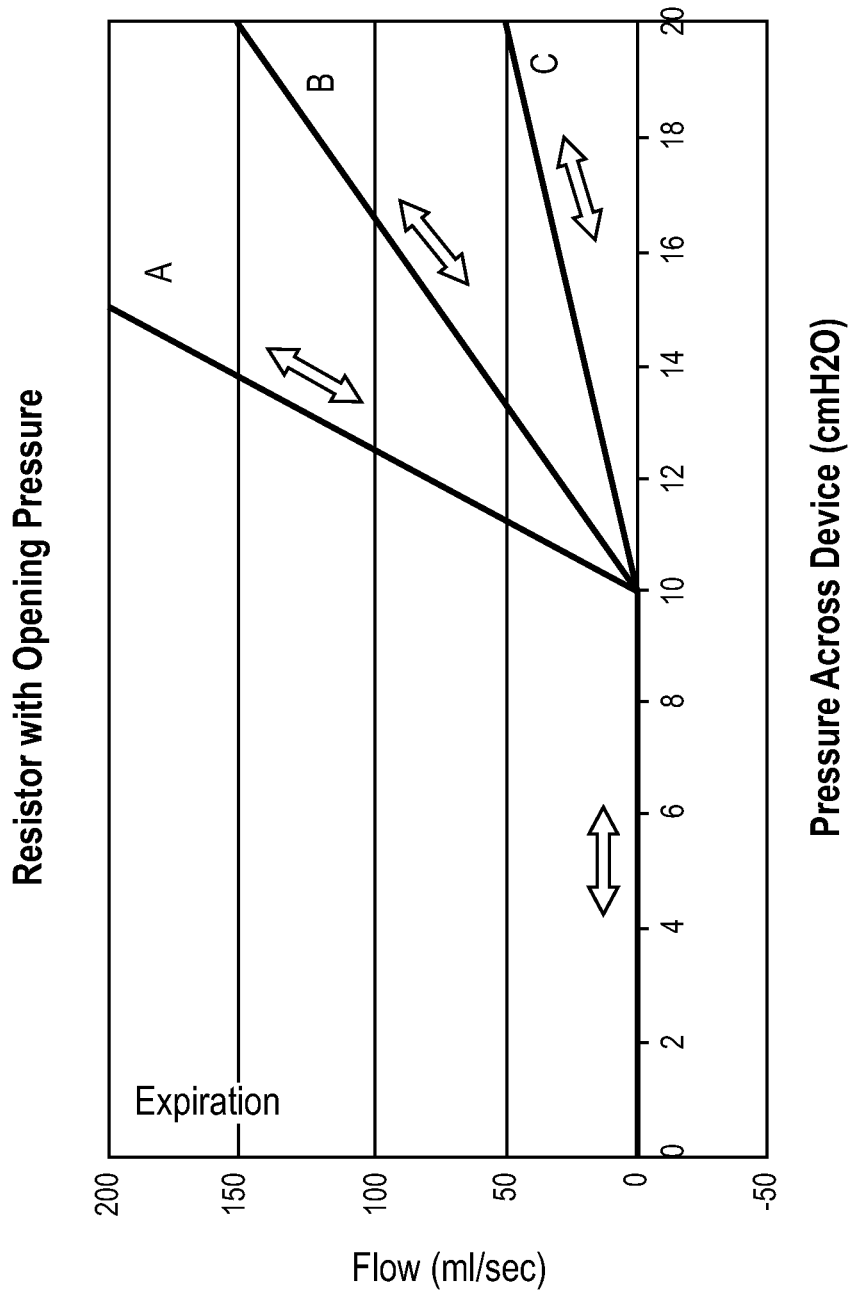
FIG. 4 shows representative resistive profiles for differential resistors with a threshold for opening.
Figure 5:
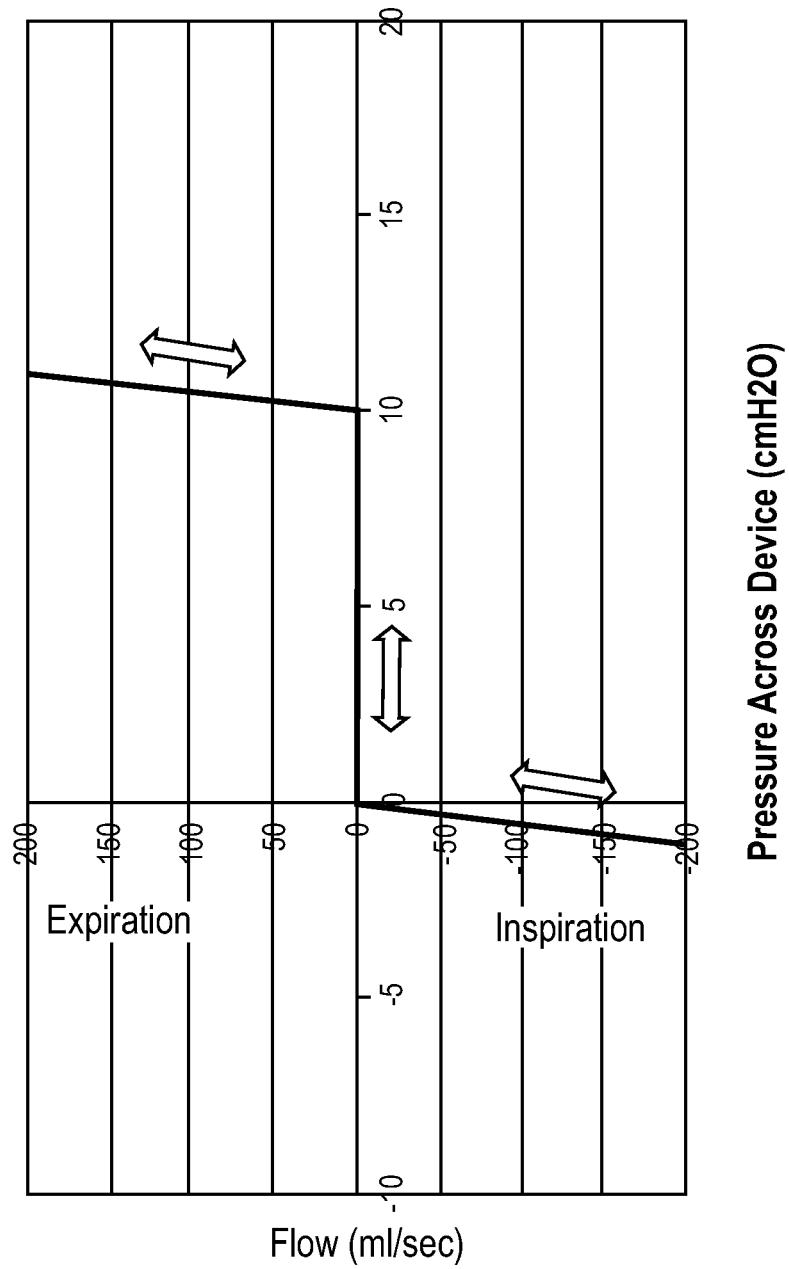
FIG. 5 shows another representative resistive profile for a differential resistor with a threshold for opening.

FIG. 4 shows a device having a resistance profile in which there is a threshold pressure for opening during expiration. In FIG. 4, for convenience, only the flow over the positive (expiration) pressures is shown. The inhalational pressure (negative pressures) can be assumed to be a constant low pressure, as shown in FIG. 5. In FIG. 4, the resistance of the device at low expiratory pressures across the device (e.g., between 0 cm of $H_2O$ and 10 cm of $H_2O$) is infinite, shown by the flat slope. At 10 cm of $H_2O$, the resistance decreases to a constant level. Three different cases (shown by the three different lines, A, B and C) are shown for devices having three different constant resistances. Thus, in this example, the threshold pressure for opening is 10 cm of $H_2O$.

Thus, in some variations, it may be desirable to block all (or substantially all) flow at low pressures during expiration until a predetermined pressure threshold for opening is reached. After this threshold is reached, the device (e.g., a valve within the device) opens, allowing air to flow through it. Depending upon the resistance to flow when the device opens, you can have many different pressure-flow relationships above this threshold value, as seen by lines A, B and C. For example, line A represents a lower resistance device, line B represents a moderate resistance device, and line C represents a higher resistance device. In any of these devices, it does not matter whether the pressure is increasing or decreasing, as the flow will match the pressure differential for any pressure across the device.

FIG. 5 shows another example of a differential resistance device having a threshold for opening during expiration. A device having the resistance profile shown in FIG. 5 may be ideal for PEEP. During inhalation (at negative pressure across the device), the device has a very low resistance (e.g., the airflow resistor may be substantially open during inhalation). During exhalation at low pressures (e.g., between zero and the threshold for opening of 10 cm of $H_2O$) there is no flow. For example, the airflow resistor is closed. Above the threshold for opening, the resistance again drops, because air may flow through the airflow resistor.

In an actual differential resistance device having a threshold for opening during expiration, there may be some flow at low pressure, although this may be very high resistance flow (e.g., around the edge of the valve), which would be seen on a resistance profile as a relatively flat (though not completely flat) slope. In addition, although the resistance profiles shown herein have abrupt transitions between high and low (or low and high) resistance regions, in practice the slopes may transition gradually (e.g., as the valve opens or closes).

Differential resistance devices having resistance profiles such as those shown in FIG. 5 may be useful as PEEP devices because they may help maintain positive end expiratory pressure within the subject's respiratory tract. For example, near the end of the expiratory portion of a respiratory cycle the pressure by which air is expelled may decrease as expiration ends. Thus, a subject expiring through a differential resistance device having a threshold for opening such as the one shown in FIG. 5 may be prevented from completely expelling air during expiration, resulting in a positive end expiratory pressure. In some variations, a respiration device configured as a PEEP device has a threshold for opening of less than about 15 cm $H_2O$, less than about 12 cm $H_2O$, less than about 10 cm $H_2O$, less than about 8 cm $H_2O$, less than about 4 cm $H_2O$, etc. For example, the threshold for opening may be between about 1 cm $H_2O$ and about 15 cm $H_2O$, or between about 1 cm $H_2O$ and about 10 cm $H_2O$.

Exemplary devices having resistance profiles similar to those shown in FIG. 5 are described more fully below, in the section titled "Exemplary Devices." In general, these devices may include an airflow resistor that is configured to be open during inhalation, and is closed at low pressure during exhalation, but at some threshold for opening, the airflow resistor opens to allow flow. For example, the airflow resistor may be biased in the direction of expiratory flow so that the pressure across the airflow resistor must exceed some threshold amount before it opens. In some variations, the airflow resistor is a bistable valve, which changes from a first stable configuration (e.g., closed during low-pressure expiration) to a second stable configuration (e.g., open during high-pressure expiration) when the pressure across the device reaches the threshold pressure.

In some variations (particularly bistable valve variations), the transition from open during high-pressure operation to closed during low-pressure operation does not occur at the same threshold pressure. These devices may have a resistance profile similar to that shown in FIG. 6.

C. Differential Resistance Devices with Threshold Release During Expiration

Figure 6:
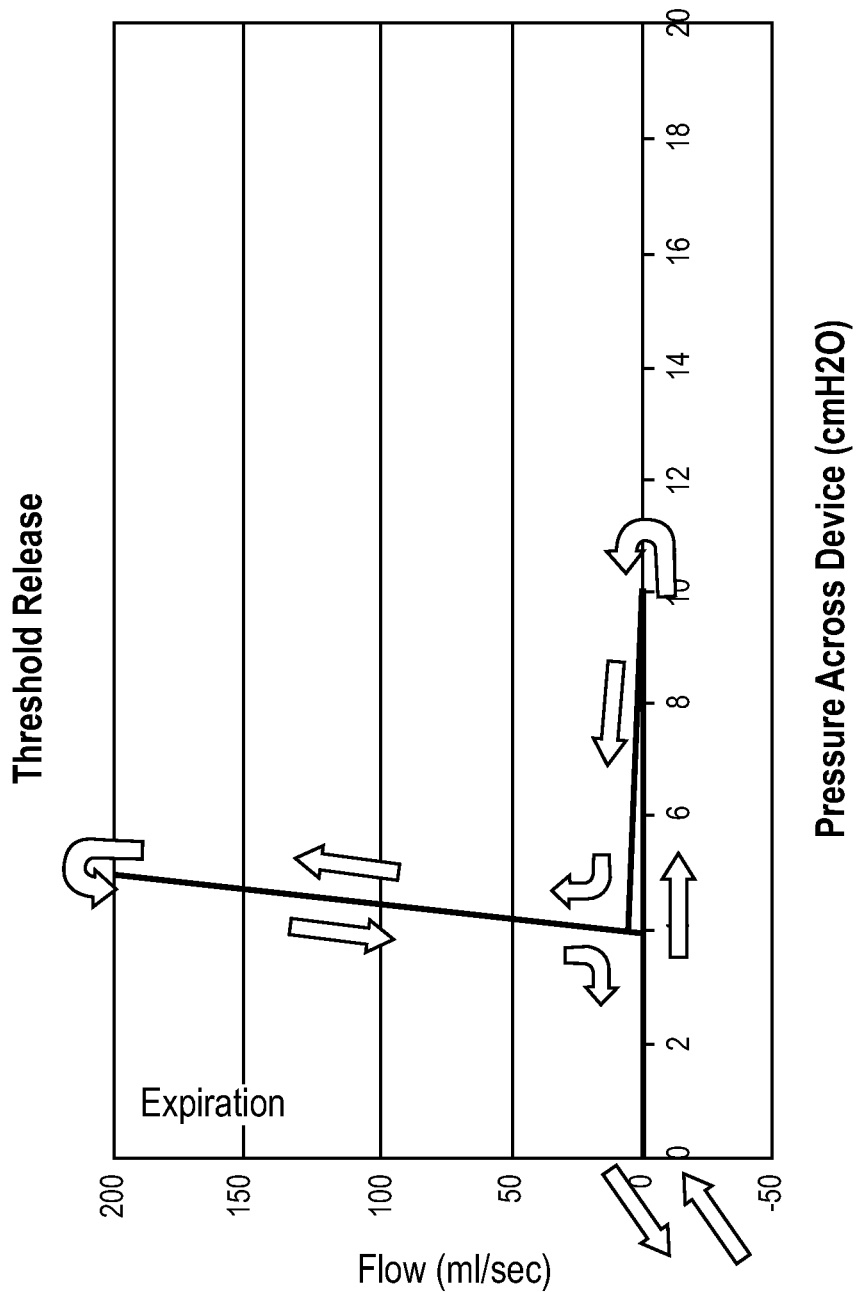
FIG. 6 shows a representative resistive profile for a differential resistor with a threshold for opening and a threshold for closing.

FIG. 6 shows a differential resistance device with a threshold for opening and a threshold release during expiration. This means that during expiration, at low pressure the device is closed, but when the pressure across the device reaches a first threshold (the threshold for opening) the valve in the device opens to allow airflow. However, this open valve does not close until the pressure across the device reaches a second threshold (a threshold pressure for closing).

For simplicity sake, only the expiratory portion of the resistance profile is shown in FIG. 6. At low expiratory pressures across the device (e.g., between zero and the threshold for opening shown here as 10 cm of $H_2O$) the device is effectively closed, preventing any airflow across the device (e.g., having an infinite resistance). When the airflow resistor is closed, but the pressure across the device exceeds the threshold for opening, the airflow resistor will open, allowing airflow with a low resistance. In this embodiment, however, the airflow resistor does not re-close (e.g., reset) when the pressure across the device falls below the threshold for opening. Instead, the pressure must fall below a threshold for closing during expiration. In FIG. 6, this threshold for closing is approximately 4 cm of $H_2O$.

The threshold for closing is the pressure at which the device is 'reset' back into the closed during expiration mode from the open during expiration mode. Once the device has closed, and flow has substantially stopped, the device will remain closed during expiration until the threshold for opening (e.g., 10 cm of $H_2O$) is again exceeded.

The resistance profile shown in FIG. 5 may be thought of as a special case of the situation described above for FIG. 6, in which the threshold pressure to return the airflow resistor closed during expiration is the same as the threshold pressure required to open the airflow resistor during expiration.

As mentioned above, resistance profiles similar to the one shown in FIG. 6 may be demonstrated by devices having bistable valves which change from a first stable configuration (e.g., closed during low-pressure expiration) to a second stable configuration (e.g., open during high-pressure expiration) when the pressure across the device reaches the threshold pressure. Example of differential resistance devices with a threshold for opening and a threshold release during expiration are also given below.

Figure 7:
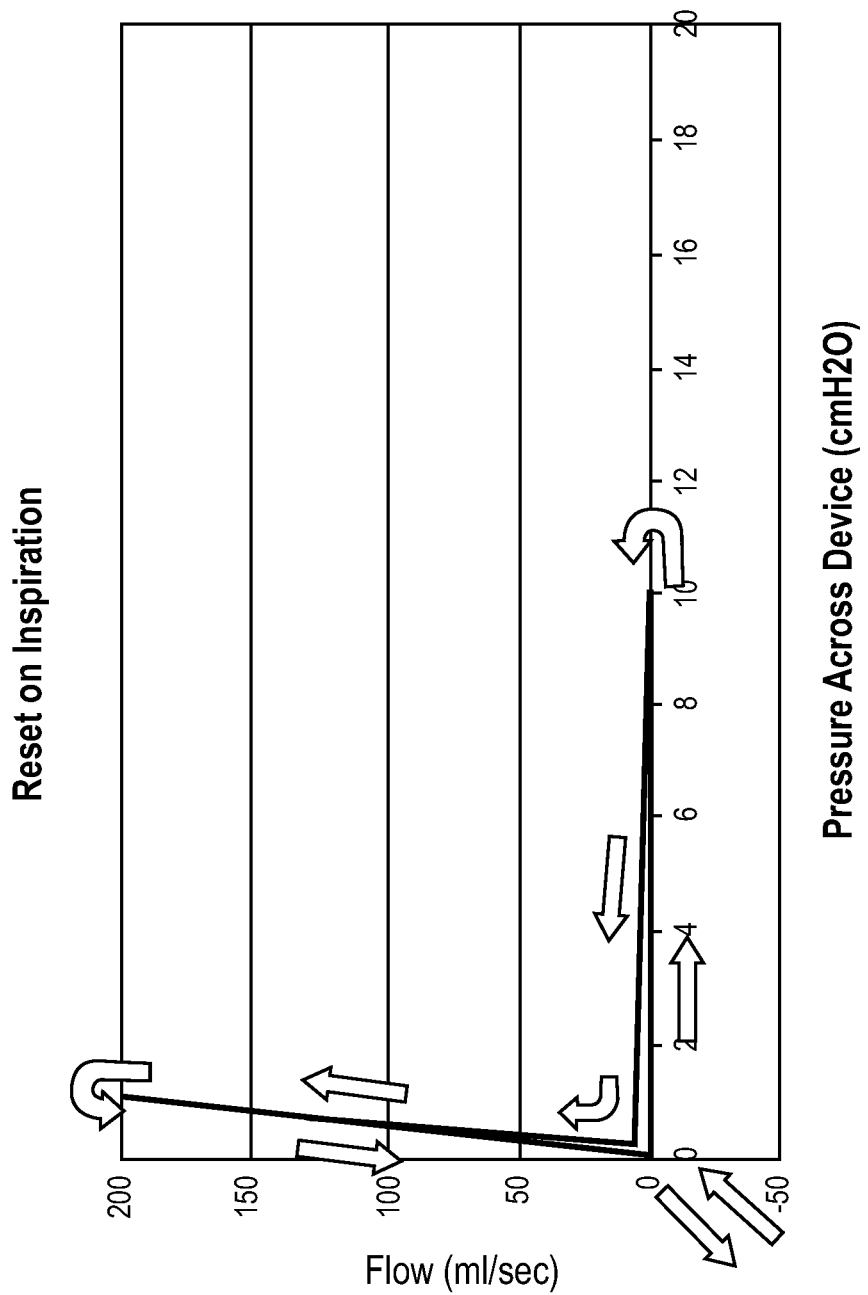
FIG. 7 shows another example of a representative resistive profile for a differential resistor with a threshold for opening and a threshold for closing.

FIG. 7 shows another variation of a differential resistance device with a threshold for opening and a threshold for release during expiration. In FIG. 7, the threshold for release (e.g., closing the airflow resistor) during expiration is approximately zero cm of $H_2O$. Thus, the device doesn't "reset" closed during expiration until after the inspiration occurs.

Devices having resistance profiles similar to those shown in FIG. 6 may also be useful as PEEP devices. In particular, devices in which the threshold pressure to return the airflow resistor to a closed state during expiration is greater than some minimum level (e.g., greater than 1 cm $H_2O$, greater than 2 cm $H_2O$, greater than 3 cm $H_2O$, greater than 4 cm $H_2O$, greater than 5 cm $H_2O$, etc.) may make effective PEEP devices. As described above, these valves may help maintain a positive end-expiratory pressure within the subject's respiratory tract at the end of an expiratory cycle of respiration. The threshold pressure for closing may be any appropriate pressure values, particularly pressures in the range of: between about 0.5 cm $H_2O$ and about 15 cm $H_2O$, between about 1 cm $H_2O$ and about 10 cm $H_2O$, etc.

It should be apparent that the resistance profiles described above are idealized profiles. In practice, the pressure-flow characteristics may be non-linear, and may be curved or have other non-straight lines. The profiles shown here illustrate general characteristics of resistance profiles. As described above, although figures such as FIGS. 5 to 7 show resistance profiles having flat regions (of infinite or very high resistance) when a valve is 'closed' during expiration, the valve may include one or more leak pathways through which air may pass. Thus, devices corresponding to the resistance profiles shown in the figures (e.g., FIGS. 5 and 6) may have a non-zero slope even when the valve is closed during expiration.

Furthermore, the profiles described above are time-independent, and thus do not accurately reflect the time dependence of any of the devices described herein. As will be apparent, the time response of the respiratory device may also affect the operation of the device. For example, it may be desirable to delay the response of the change in resistance based on the time point of the respiratory cycle. For example, it may be beneficial for a PEEP device to delay closing the valve after switching from inhalation to exhalation, even though the respiratory pressure is relatively low across the valve.

General PEEP Devices

The respiratory devices described herein alter airflow into and out of the lungs through a respiratory cavity such as the mouth and/or the nostrils of the nose in order to achieve positive end-expiratory pressure (PEEP). These respiratory devices typically include one or more passages, a holdfast for securing the device in communication with a subject's respiratory cavity, and an airflow resistor (e.g., valve) capable of obstructing airflow with high resistance during low-pressure expiration, and opening to allow substantial airflow during high-pressure expiration. In particular, the respiratory devices may include an airflow resistor having a threshold pressure during expiration for opening the airflow resistor to allow airflow when the threshold pressure is exceeded. In some variations, the airflow resistor also has a threshold for closing during expiration, below which the airflow resistor inhibits expiratory airflow until the threshold pressure for opening is again exceeded. Specific examples of devices having appropriate airflow resistors are described below.

Any of the devices described herein may be specifically adapted for nasal use. Thus, these devices may be considered nasal respiratory devices. For example, the devices may include a holdfast for securing the passageway(s) in communication with the nasal cavity to regulate airflow through the nasal cavity. The holdfast may secure the device at least partially over and/or at least partially across the nose (particularly in contact with the area around the nasal opening). In some variations, the holdfast secures the device at least partly within the nasal cavity. Nasal devices described herein may be configured so that they do not cover the subject's mouth, and therefore the subject may be free to breathe through the oral cavity without additional resistance.

The respiratory devices described herein generally comprise an airflow passageway and an airflow resistor. The airflow passageway (or "passageway") generally defines a channel allowing the passage of air. The passageway may be of any suitable size or shape; however it is configured so that when the respiratory device is worn by a patient, the passageway comprises an opening leading toward the patient's lungs in fluid connection with an opening that leads away from the patient's lungs. The terms "patient" and "subject" are used to describe any user of the respiratory device, including users who are not using the respiratory device for therapeutic purposes. The airflow passageway may be any suitable length. For example, the passageway may be as short as the airflow resistor will allow (e.g., extending only far enough to communicate with the airflow resistor). Similarly, the airflow passageway may be longer than the space required to support the airflow resistor. For example, in versions of the respiratory device adapted for at least partial insertion into a nasal cavity, the airflow passageway may be approximately as long as the length of an average nare. In some versions, the passageway extends the length of an average nasal chamber.

The neutral cross-sectional area of the passageway may be of any appropriate size. Neutral cross-sectional area may refer to the cross-sectional area of the passageway when the device allows air to flow through the passageway without additional resistance (e.g., from the airflow resistor). In particular, the size (e.g., diameter) or shape of the passageway may depend upon configuration of the respiratory device. For example, respiratory devices configured to be inserted within the nasal cavity (e.g., a nasal chamber) may have an area that is approximately the area of a narrow portion of the nasal cavity, or slightly narrower. Respiratory devices configured to be secured over an oral cavity or a nasal cavity may have passageways of larger diameters. Furthermore, the cross-sectional area of a passageway may vary along the length of the device.

The airflow passageway may comprise a dedicated structure defining the inner wall of the airflow passageway, or it may be a structural component of the device. For example, the passageway may comprise a passage wall defined by a rim. A rim may be a tube (or tunnel) of material of any appropriate thickness. The rim may also be a frame, rather than a complete tube. The rim may comprise a sufficiently rigid material so that it can support the passageway, and prevent the passageway from collapsing during use and during respiration. In some versions, at least a portion of the rim is made of a compressible material that may be compressed to facilitate insertion and removal, while maintaining the ability to support the passageway and prevent complete collapse of the passageway during respiration. The rim may also be somewhat compressible during respiratory flow. The airflow passageway (including a rim portion) may also serve as an attachment site for other components such as airflow resistors, filters, anchors, etc.

The rim may be any suitable shape or size. For example, the rim may comprise a ring shape or an oval shape. As mentioned above, the rim may define the inner diameter of the passageway. In some versions, the rim comprises a material having strength sufficient to prevent the collapse of a respiratory device that has been inserted into a nasal cavity. For example, the rim may comprise a metal, a polymer (particularly stiff polymers), etc. In some versions, the rim may comprise softer or "weaker" materials which are formed or arranged so that the final shape of the rim has sufficient strength to prevent the collapse of the respiratory device during use.

As mentioned above, a respiratory device may include a rim that is a tube or tubular body having a distal end and a proximal end, through which the airflow passageway extends. In variations of the device that are adapted to be secured in a subject's nasal cavity, the distal end of the respiratory device is inserted first into the subject's nose, so that the device is worn so that during inhalation air flows from the proximal to the distal end of the passageway, and during expiration air flows from the distal to proximal end of the passageway. In some variations, the proximal end of the tubular body has different properties from the distal end. For example, the thickness of the tubular body from distal end to proximal end may vary.

In some variations, the respiratory device has a tubular body in which the distal end is more compliant than the proximal end. Thus, the distal end may be more readily compressed for insertion into the nasal cavity, while the proximal end is somewhat more rigid, allowing for easier removal/insertion of the device. A more compliant distal end may also help the device better fit a subject wearing the device, and may enhance comfort. As described more fully below, the distal region of the device may conform to fit the nasal cavity.

In some variations, the distal end is more compliant than the proximal end because different regions of the tubular body are made from different materials or have different structures. For example, a distal portion of the tubular body may have a wall thickness that is less than the wall thickness of the more proximal portion of the tubular body. The rim (e.g., tubular body) may have two or more regions of different wall thickness, or it may have regions of continuously varying thickness. The wall thickness may be uniform for a given distal-to-proximal position (e.g., along the length of a respiratory device's tubular body). As mentioned above, the wall thickness of the tubular body (rim) may be zero in some regions, meaning that the tubular body includes holes or windows, or comprises a frame.

Regions of different wall thickness may result in different regions of the airflow passageway having different diameters or cross-sectional shapes. For example, in variations where the respiratory device has a tubular body having a proximal wall thickness that is greater than the distal wall thickness, the region where the thicker proximal wall thickness meets the thinner distal wall thickness may form a step or ledge along the wall of the passageway. In this example, the outer diameter (OD) of the tubular body is uniform while the inner diameter (ID) has at least two different measures. As described in more detail below, this ledge or step within the passageway may form a valve seal surface by providing a surface on which a valve (e.g., a flap valve) may abut or lie against when in the closed position.

The tubular body may have any appropriate cross-sectional area. For example, a rim configured as a tubular body may have an elliptical cross-section through its length that is shaped similarly to that of most patients' nares. This shape may help maximize the cross-sectional size of the passage while maintaining comfort. The passageway may also comprise other cross-sectional shapes, such as circular, polygonal, teardrop, or other asymmetric shapes.

In some versions, the respiratory device does not include a separate rim forming the passageway. For example, the airflow passageway of the respiratory device may be a passageway through a holdfast.

The devices described herein may include more than one passageway. Furthermore, although many of the illustrations of devices provided herein are for nasal devices (e.g., devices for use in a nasal cavity), it is to be understood that these devices may be adapted for use with any respiratory orifice (e.g., mouth, nose, etc.).

Airflow resistors for use with the PEEP devices described herein are typically positioned in communication with an airflow passageway, so that at least some (if not all) of the air flowing through the passageway passes the airflow resistor. Thus, an airflow resistor modulates, alters, varies, or keeps constant the amount of resistance, the degree of airflow, or the pressure differential across the device or through a passageway in the device. As described above, a typical PEEP airflow resistor has very little resistance to inhalation, has a high resistance to expiratory airflow at low expiratory pressures, and has a threshold pressure for opening, above which the airflow resistor has a relatively low resistance to expiration. In some variations, the airflow resistor (e.g., a valve) has a threshold pressure for closing during exhalation, so that if the pressure across the valve during expiration falls below the threshold for closing, the airflow resistor will close, resulting in a high resistance to flow.

Examples of different types of airflow resistors are described below and illustrated in many of the figures. Any airflow resistance device having a resistance profile similar to the resistance profiles shown in FIG. 4, FIG. 5 and FIG. 6 may be used.

Some variations of the airflow resistors described are modified flap valves. The flap region may include a stiff or flexible material, or some combination thereof. In some variations, the flap valve includes a stiff region of the valve, which may help give the flap support. In some variations, the flap comprises a polymeric material, as described below. The flap valve may be biased (e.g., in an open or a closed position) or it may be unbiased. A bias element such as a spring may be used, or the flap may be made of a material that has elastomeric properties that bias the valve in a particular position. A biased valve is a valve that tends to remain in a particular position (e.g., flat, bent, open, closed, etc.) when at rest, and changes position (e.g., from closed to open) after an appropriate force is applied to the device to overcome the bias. As described herein, the bias may be provided by a biasing element (e.g., spring, tether, weight, or the like), or a material property of the valve (e.g., the stiffness). The airflow resistor may also be used with additional components. For example, respiratory devices may include an airflow resistor seal surface (valve seal surface), an airflow resistor support (valve support), and/or an airflow resistor aligner (valve aligner). Examples of these features are provided in more detail in U.S. Patent Application titled "NASAL RESPIRATORY DEVICE," filed May 22, 2007 by inventors Rajiv Doshi, Bryan Loomas, and Ryan Kendall Pierce, the entirety of which is herein incorporated by reference in its entirety.

The airflow resistor or valve may be any appropriate shape, particularly shapes in which the passageway may be blocked or at least partly occluded.

The respiratory device may also include one or more leak paths. A leak path allows air to flow through or past the respiratory device even when the airflow resistor is closed. A leak path may be included as part of any portion of the device, including the holdfast, the rim (e.g., the tubular body), or the airflow resistor. The sizes, locations and distributions of the leak path(s) may be chosen to permit a desired amount of airflow through the device at a known pressure and/or flow rate. In particular, the leak path may be incorporated as part of an airflow resistor. For example, the leak path may be one or more holes or channels through the valve, even when the valve is closed. In some variations, the leak path is not included as part of the valve.

The PEEP respiratory device may further comprise a holdfast for releasably securing the device in communication with a nasal cavity. The holdfast may facilitate the positioning and securing of the device in a desired location, such as over or within (e.g., substantially within) a nasal orifice. In particular, the holdfast may allow the device to be anchored, positioned, and/or stabilized in any location that is subject to respiratory airflow such as a nasal cavity.

Nasal cavities may include the following anatomical structures, or conduits defined by the following anatomical structures: the nostrils, nares or nasal chambers, limen, vestibule, greater alar cartilage, alar fibrofatty tissue, lateral nasal cartilage, agger nasi, floor of the nasal cavity, turbinates, sinuses (frontal, ethmoid, sphenoid, and maxillary), and nasal septum. The term "nasal cavity" may refer to any sub-region of the Nasal Fossa (e.g., a single nostril, nare, or nasal chamber).

In some versions, the holdfast may also secure a seal between the respiratory device and the respiratory airway, so that at least some of the air exchanged between the outside of the patient and the respiratory airway must pass through the respiratory device. In some versions, the holdfast seals the device in communication with a respiratory cavity completely, so that all air must be exchanged through the device. In some versions, the holdfast seal is incomplete, so that only some of the air exchanged between the patient and the external environment passes through the device. As used herein, "air" may be air from the environment external to the patient, or it may be any respiratory gas (e.g., pure or mixed oxygen, $CO_2$, heliox, or other gas mixtures provided to the user). In some versions, the holdfast may comprise an anchor or anchor region.

In some variations, the device is to be placed by the patient or the healthcare provider in or around the nasal cavity. Holdfasts appropriate for nasal cavities may secure the device in position within a nasal cavity (e.g., through one or both nostrils) or against surrounding structures. The holdfast may comprise a shape, surface or material that secures the device in communication with a nasal cavity. For example, the holdfast may comprise a cylindrical shape that allows the device to fit securely or snugly within a nostril. The outer surface of the device may comprise a holdfast including an adhesive material. In addition to holding the device in place, the holdfast may also partially or completely seal the device in communication with the nasal cavity. The holdfast may comprise insertive and/or non-insertive mechanisms. In some versions, the holdfast comprises a mechanical connection between the device and the user, such as clips, straps, and the like.

The holdfast may be formed from a soft or compliant material that provides a seal, and may enhance patient comfort. Furthermore, compliant materials may reduce the likelihood that the device cuts off blood flow to the part of the respiratory cavity and surrounding regions to which the device is anchored. This compliant material may be one of a variety of materials including, but not limited to, plastic, polymers, cloth, foamed, spongy, viscoelastic, and/or shape memory materials. Shape materials include any that have a preferred conformation, and after being deformed or otherwise deflected or altered in shape, have tendency to return to a preferred conformation. Soft shape memory materials may include, but are not limited to, urethane, polyurethane, sponge, and others (including "foamed" versions of these materials). Alternatively, the holdfast may not be soft or compliant and may instead be a rigid structure that interfaces directly with the respiratory orifice. For example, in versions of the respiratory device configured to be used at least partly within a nasal cavity, it is understood that the device may fit completely within a nostril (or both nostrils), or may project out of the nostril, depending on the particular embodiment. In some cases, the device may be placed high enough within the nasal cavity so that it cannot be seen within the nostril. In some embodiments the device may be located completely outside of the nose, for example, in some versions the holdfast has a shape that conforms to the outside surface of the nose. Thus, the holdfast may comprise one or more straps, bands, or the like to ensure an adequate fit and/or seal maintaining the device in communication with the nasal cavity. In another embodiment the holdfast may comprise one or more projections that are inserted within the nostrils. In some versions, a device may be placed at least partly in both nostrils, and may comprise a bifurcated passageway or two passageways that the holdfast places in communication with the nasal cavity through each nostril. In this case, the inspiratory and/or expiratory airflow to and from the lungs may be regulated through each nostril separately or together. In some versions, separate devices may be placed at least partly in each nostril, and may be connected to each other and/or to the patient using a clip, tether, strap, band, chain, string, or the like. In these versions, the connection means may connect one rim from one device to a rim from a second device or a holdfast from one device to a holdfast from a second device, or some combination thereof. Any portion of one device may be connected by said connection means to any portion of the second device. The connection means may comprise a shape memory material. Such a system would facilitate subsequent removal of the device and make migration of the devices deeper into the nasal cavity less likely. Finally, in some devices, an adhesive region may be present to help attach the device to the inside or outside of the nose (including the nostrils), to the oral cavity, to the neck, or to the face. The use of an adhesive or any other means may prevent the inadvertent or otherwise undesired removal of the subject devices during sleep.

The holdfast portion of a respiratory device may also be shaped to fit within the subject's anatomy to secure the device in place and/or to prevent leakage of airflow around the device. For example, the holdfast may be shaped to fit within the widening of the nasal cavity immediately inside the nares (opening of the nostril). As mentioned above, the holdfast may conform to the walls of a portion of the nasal cavity both to hold the device within the nose, and also to prevent substantial leak of air around the device when worn in the nose. Materials such as foams (e.g., foamed polyurethane) may be particularly useful for this purpose, since these materials may be readily compressed for insertion and rapidly expand within the nasal cavity to secure the device in place.

A holdfast may be attached to a respiratory device. For example, a holdfast may be attached to a rim. In one variation, the holdfast is connected to the outer surface of the tubular body. A holdfast may be glued, taped, stitched, welded, or otherwise connected to the rim of a respiration device. In some variations the holdfast circumferentially surrounds at least a portion of a rim. For example, in one variation the distal end of the tubular body (e.g., rim) of the device is ensheathed by a holdfast of foamed material. In some variations, the holdfast thickness is substantially uniform along most or all of the periphery of the device. In some variations, it may have variable thickness, for example it may be thicker or thinner at the long ends of the device. In other cases, the holdfast thickness may be either symmetrically or asymmetrically distributed. Similarly, the height and length of the foam forming a holdfast may also be uniform or non-uniform, symmetrically or asymmetrically distributed.

A holdfast may be thicker in some regions than in other regions. For example, the cross-sectional profile of the holdfast (e.g., the profile though the long axis of a respiratory device including a holdfast) may be thicker in some places than in others. In some variations, e.g., when the tubular body or passageway of the device has an elliptical profile (cross-sectional profile), the holdfast in communication with the tubular body is thicker near the long axis of the elliptical profile of the tubular body than at the short axis of the tubular body. In some variations, the thickness of the holdfast around the profile of the tubular body cross-section is related to the diameter of the passageway through the device. For example, the thickness of the holdfast at any point outside of the passageway may be between about 0.2 times and about 2 times the distance from the center of the passageway to the outer edge of the tubular body around the radius of the passageway. On an exemplary device having a tubular body with an elliptical profile, the holdfast may be between about 0.8 mm and about 8 mm thick at the long axis of the elliptical cross-section of the tubular body, and between about 0.4 mm and about 4 mm thick at the short axis of the elliptical cross-section of the tubular body.

The device may be removably secured by a holdfast, meaning that the device may be inserted into the subject's nasal cavity for some amount of time, and then removed. For example, a removable holdfast exerts sufficient pressure on the nostril walls (e.g., within the nasal cavity) to hold the device in position without harming the subject, or producing too much discomfort. The device may be used continuously for an appropriate time period (e.g., overnight, such as 6-8 hours). Thus, the holdfast does not generally need to be secured more permanently. The holdfast material properties and shape typically lend themselves to easy, fast, and pain-free insertion and removal. Thus, as described herein, the holdfast may be a compressible/expandable foam material. The shape and size of the holdfast may also be chosen to appropriately secure the device within a subject's nasal cavity comfortably. For example, the foam may have compression properties that allow it to be readily compressed (for insertion into the nasal cavity), but expand to fit the cavity quickly once inserted. The holdfast may also have a thickness and width sufficient to fit snugly but comfortably within the subject's (including an 'average' subject or range of different subject sizes) nasal cavity. In some variations, the foam thickness is not uniform. For example, in some variations, the ends of the holdfast region comprise a foam that is thicker than in the middle, which may allow the device to fit noses which are longer and narrower.

Respiratory devices may be made from any appropriate material or materials. In certain embodiments, the devices include a shape memory element or elements, as part of the holdfast, in the airflow resistor, or in giving form to the passageway. Any convenient shape memory material that provides for flexibility and resumption of configuration following removal of applied force may be employed in these embodiments. For example, shape memory alloys may be used. A variety of shape memory alloys are known, including those described in U.S. Pat. Nos. 5,876,434; 5,797,920; 5,782,896; 5,763,979; 5,562,641; 5,459,544; 5,415,660; 5,092,781; 4,984,581; the disclosures of which are herein incorporated by reference in their entirety. The shape memory alloy that is employed should generally be a biocompatible alloy. Biocompatible alloys may include nickel-titanium (NiTi) shape memory alloys sold under the Nitinol™ name by Memry Corporation (Brookfield, Conn.). Also of interest are spring steel and shape memory polymeric or plastic materials, such as polypropylene, polyethylene, etc.

Rubber and polymeric materials may also be used, particularly for the holdfast, rim, or airflow resistor. Injection moldable materials such as polyether block amide (e.g., PEBAX®), and the like may be used. Materials which may be used include: latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins).

Biocompatible materials may be used, particularly for those portions of the device (e.g., the holdfast) which may contact a user. In addition to some of the materials described above, the biocompatible materials may also include a biocompatible polymer and/or elastomer. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art.

Exemplary Devices

The following exemplary devices contain valve mechanisms that may be used to achieve PEEP, and therefore may be referred to as PEEP devices or PEEP valves. Many of these examples describe only airflow resistors or the valve components of an airflow resistor, however it should be understood that these airflow resistors or valves may be used as part of a respiratory device. It should also be understood that a single device may include more than one of these valves.

The valves described herein may be used as part of a PEEP device having a resistance profile similar to that of FIG. 5 (exemplifying a differential resistance devices with a threshold for opening during expiration), and FIG. 6 (exemplifying a differential resistance devices with a threshold for closing during expiration).

A. Differential Resistance Devices with a Threshold for Opening During Expiration In general, differential resistance devices having a threshold for opening during expiration comprise one or more valves that open (or open more fully) to reduce the resistance through the valve only after the pressure across the valve exceeds the threshold for opening. In some variations of these devices, the threshold for opening is determined by a bias which must be overcome before the valve (or valves) can be opened. In particular, a bias may be preloaded, so that the valve cannot be opened until the preloaded force is overcome. Thus, the threshold pressure for opening a valve may be the preloaded force.

Figure 18A:
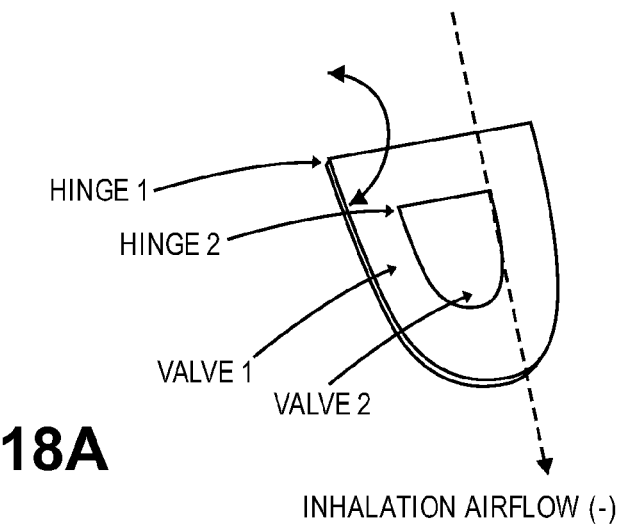
FIGS. 18A to 18C illustrate the operation of nested flap valve.
Figure 18B:
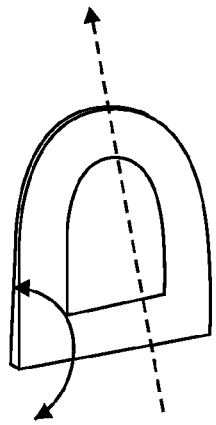
Figure 18C:
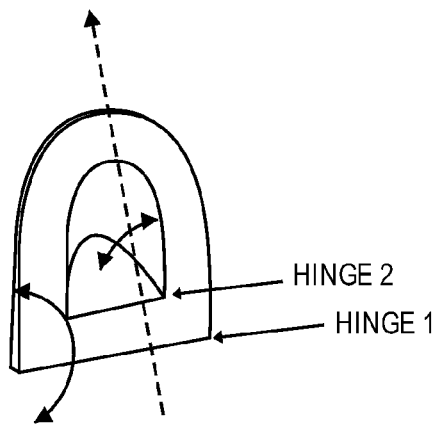

One class of resistance devices having a threshold for opening during expiration are valves having nested flaps, where the flaps open in opposite directions, as shown schematically in FIG. 18A-18C. In particular, nested flap valves may be used for PEEP devices when one of the flaps is biased so that it opens only after the pressure across the valve exceeds a threshold for opening. Thus, a nested flap valve may be configured so that the resistance profile resembles the profile seen in FIG. 5, for example.

The generic nested flap valve shown in FIG. 18A has two flaps, a first flap and a second flap, that are each hinged. In FIG. 18A (during inhalation), the first flap is opened during inhalation, so that air may flow from the top of the valve to the bottom of the valve. Relating this to the resistance curve shown in FIG. 5, during inhalation (negative pressure), the first flap of the valve is easily opened, and has a very low resistance. FIG. 18B shows the valve flap during exhalation. The positive pressure moves the first flap to close off the passageway (the passageway is not shown). At positive pressures (exhalation) below the threshold for opening the second flap, the first flap closes the passageway but the pressure across the valve is not sufficient to open the second valve. Thus, the second flap is biased so that it only opens when the pressure exceeds the threshold pressure for opening. Any appropriate bias may be used. A bias applies force to oppose the opening of the flap. For example, the second flap may be biased by a structural bias (e.g., a spring), an elastomeric material (or region of the valve), or a combination of these. The second flap may be biased because of the material property of the hinge region or the flap itself. Once the pressure across the valve during expiration exceeds the threshold for opening, the second flap opens, allowing airflow through the device during exhalation. This is illustrated in FIG. 18C.

The flaps of a nested flap valve may be oriented in any appropriate orientation. For example, in FIG. 18A-18C, the flap valve is oriented so that both flaps are hinged in parallel. In some variations, it may be desirable to orient the flaps so that they open in different directions. Thus, the hinges of the nested flaps may be perpendicular, or parallel, or any appropriate angle.

Figure 19A:
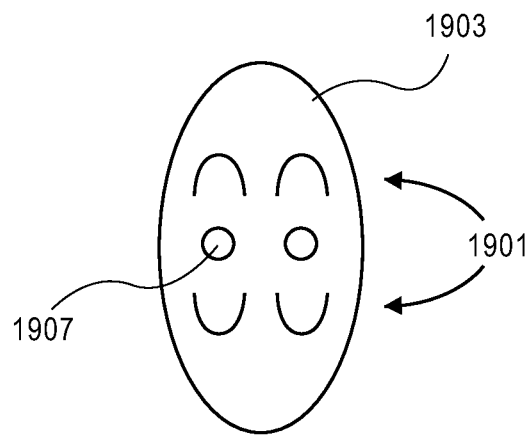
FIGS. 19A and 19B illustrate different variations of a flap valve having additional cutout valves.
Figure 19B:
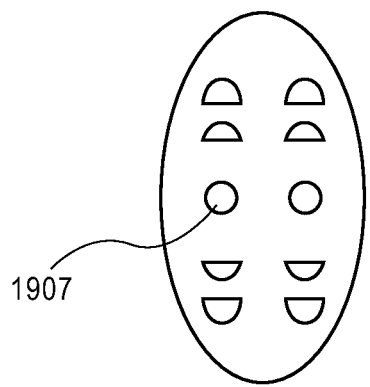

A living hinge may be used with any of the appropriate valves described herein, including flap valves. Thus, in FIG. 18A-18C, either the first or second flap may be formed (e.g., cut, molded, etc.) from the same material. Thus, the valve may include a living hinge and a region that deflects under pressure, allowing airflow. The size and shape of the opening formed by the deflectable material (as well as the shape and size of the living hinge) may determine the resistance to airflow through the valve. FIG. 19A illustrates an examples of living hinges for a valve similar to the nested valve in FIGS. 18A-18C. FIG. 19A shows four nested flaps 1901 cut into the body of the first flap 1903. The flap also includes holes 1907 (e.g., post holes) for mounting to one or more valve aligners. The nested flaps are shown as semi-circular cutout regions of the flap having a living hinge between the ends of the cutout region. These hinged flaps may allow airflow, and will open when pressure is applied. The amount of pressure required to open these flaps may be effected (or controlled) by the length of the hinge, the size (e.g., area) of the cutout region, the thickness and/or stiffness of the material, the effective moment arm (e.g., the distance from the flap hinge to the effective position of rotational force from the pressure), etc. The living hinge region (the region that is not cut out) may also be shaped by partially shaping or cutting the material forming the hinge region. For example, the hinge region may be undercut or thinned to make opening easier.

Figure 8A:
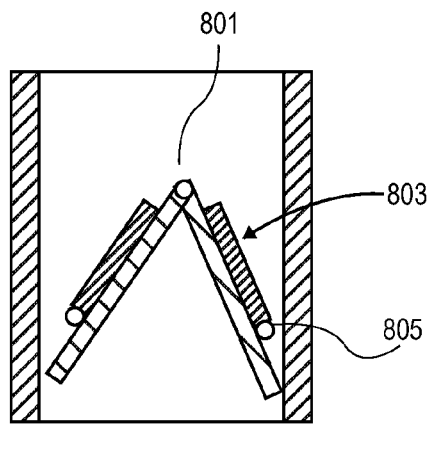
FIGS. 8A and 8B show side views through a portion of one variation of a respiratory device having nested flap valves.
Figure 8B:
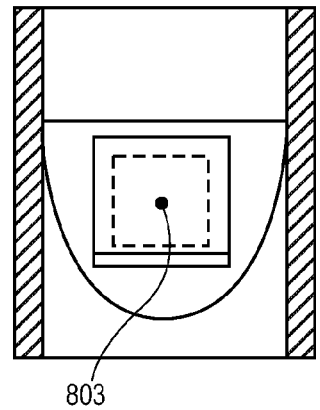
Figure 8C:
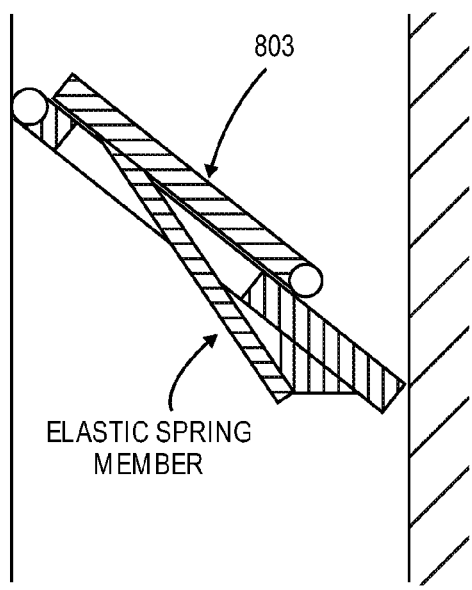
FIG. 8C shows a cross-section view through the valve show in FIG. 8A.
Figure 8D:
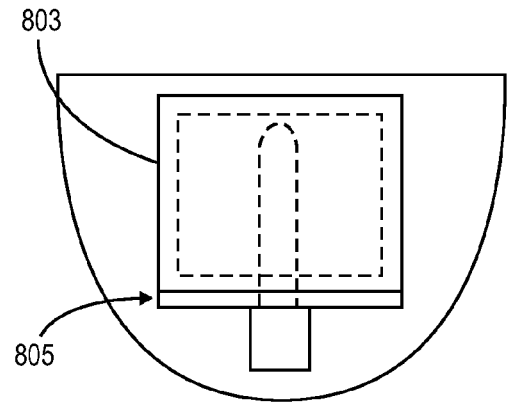
FIG. 8D shows a detailed view of the flap valve shown in FIGS. 8A-8C.

FIG. 8A shows another example of a device having nested flap valves. A first ("inspiratory") pair of flap valves (hinged 801 together in the center of the passageway) open easily during inspiration, when pressure is greater from proximal region of the device, shown here towards the top of the device. A second ("expiratory") pair of flap valves 803 is located on each of the inspiratory flap, and hinged 805 to open during expiration, when pressure is greater from distal region of the device, shown here towards the bottom. The flap door of the second pair of flap valves is biased using an elastic spring member, as shown in FIG. 8C in a cross-section though one of the pairs of nested valves. Thus, when pressure across the valve during expiration exceeds the threshold for opening which is set by the elastic spring member, the valve will open. FIG. 8D shows a side view of the surface of the inspiratory valve, showing the embedded expiratory valve thereon.

Figure 9A:
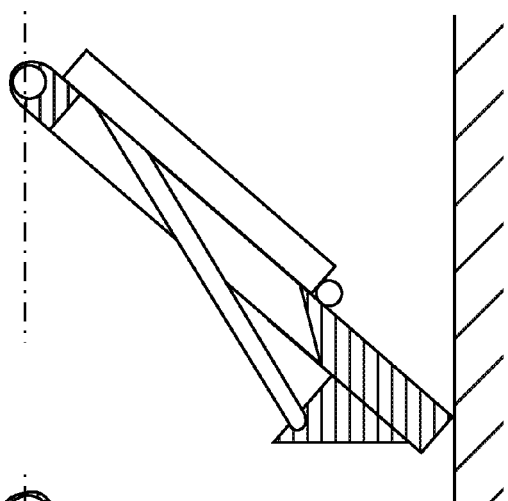
FIGS. 9A to 9C illustrate the operation of a door-within-a-door valve as described herein.
Figure 9B:
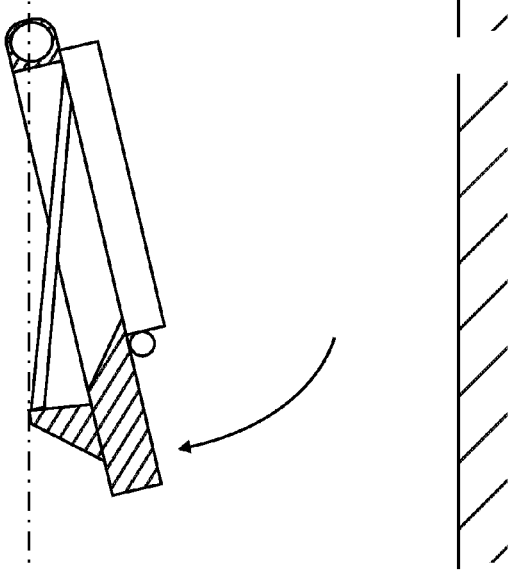
Figure 9C:
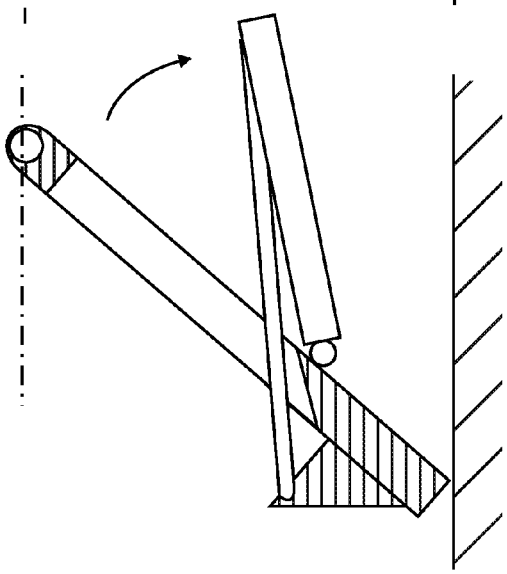

In operation, the valve shown in FIG. 8A to 8D operates as shown in FIG. 9A to 9C. At rest, the valve (or pairs of valves) is closed, cutting off flow through the passageway. As shown in FIG. 9B, during inspiration, when air is flowing from the proximal to the distal (e.g., shown as top to bottom) ends of the device, the inspiratory flap valve(s) opens to allow airflow through the passageway relatively unobstructed. The valves in FIGS. 8 and 9 are relatively stiff flap valves, so that the valves do not collapse during normal operation. During expiration, the inspiratory flap valve closes, and the force applied by the subject during expiration acts across the expiratory valve, which is biased by the elastic spring member (or any appropriate bias). If the pressure across the valve is greater then the force applied by the elastic spring member, then the expiratory valve opens, as shown in FIG. 9C.

As mentioned briefly above, the force applied by the spring member in FIGS. 8A to 9C corresponds to the threshold pressure for opening. Thus, the threshold pressure for opening can be adjusted or predetermined based on the bias element characteristics, including the attachment of the bias element (here, the spring member) to the valve.

Figure 10A:
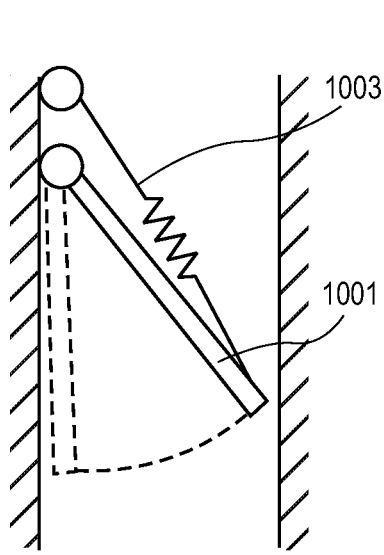
FIGS. 10A to 10C schematically illustrate different bias placement in a flap valve for use with the PEEP configured devices described herein.
Figure 10B:
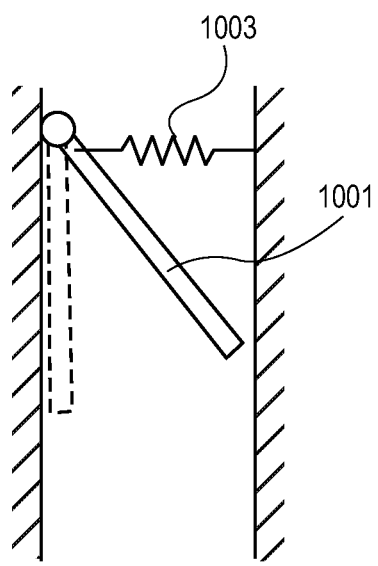
Figure 10C:
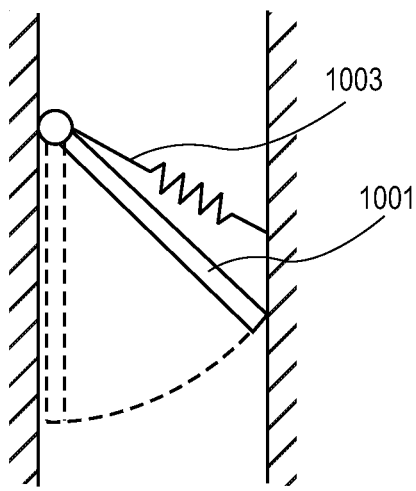

FIGS. 10A to 10C illustrates the effect of bias position on the threshold pressure for opening. In FIG. 10A, the valve stays closed until a predetermined pressure is reached across the valve (a threshold pressure for opening), and then the valve opens, allowing maximum outflow until the pressure decrease below the threshold. This variation comprises a single flap valve that is in communication with the walls of the passageway, and is hinged or otherwise flexibly (movably) connected at one end. This valve may be incorporated into a device such as the device shown in FIGS. 8A to 9D.

In FIG. 10A, the valve is shown in cross section as a stiff valve 1001, connected to a bias 1003 (e.g., a spring, elastomeric material, etc.). In FIG. 10A, the biasing force applied by the spring as the valve is opened is likely to decrease slightly as the valve leaf (flap) is deflected open by pressure across the valve. Thus, the placement of the bias may affect the amount of force required to open the valve completely or partially. FIGS. 10B and 10C show arrangements of the bias element 1003 which may result in an almost constant force, adding little additional resistance to completely open the valve once initial pressure is exceeded. Thus, the placement of a biasing element may be chosen so that the threshold pressure required to fully open the valve remains constant, or increases as resistance through the device decreases (as the valve opens).

Figure 11A:
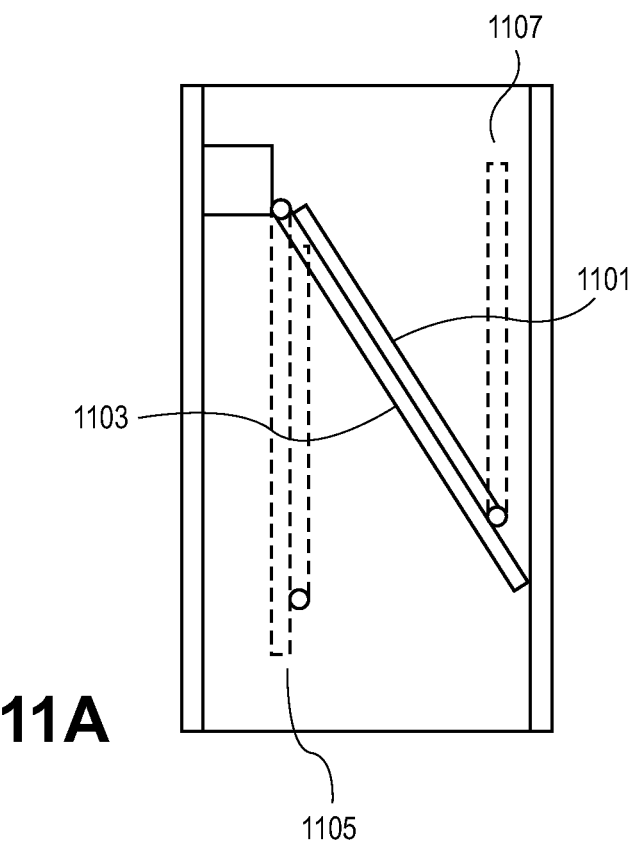
FIG. 11A shows a cross-sectional view of a door-within-a-door valve.
Figure 11B:
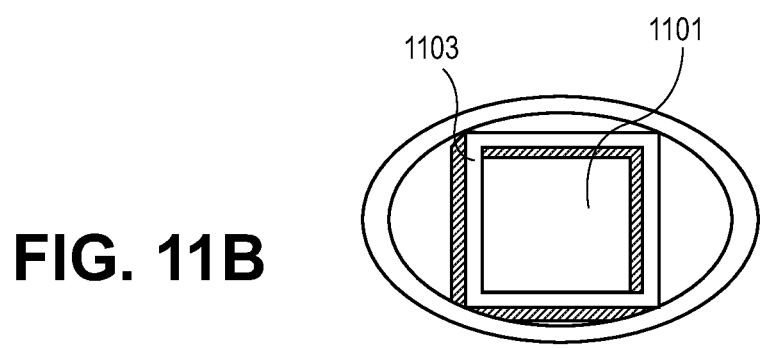
FIG. 11B shows a top view of the valve of FIG. 11A.
Figure 12A:
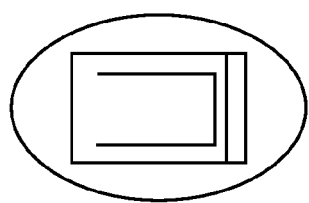
FIGS. 12A-12C show top, side cross-section and bottom views of a valve having a living hinge as described herein.
Figure 12D:
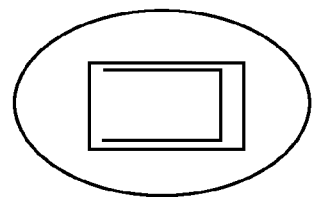
FIGS. 12D-12F show top, side cross-section and bottom views of another airflow resistor having a living hinge, similar to the valve shown in FIGS. 12A-12C.
Figure 12B:
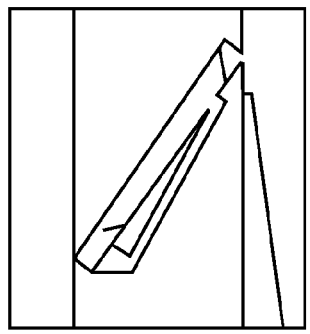
Figure 12E:
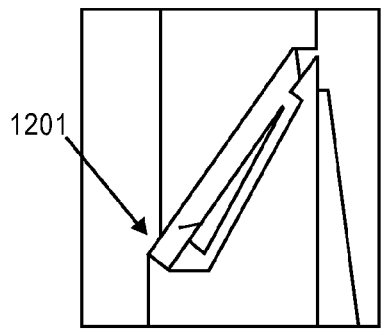
Figure 12C:
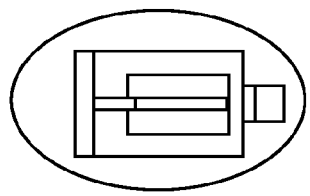
Figure 12F:
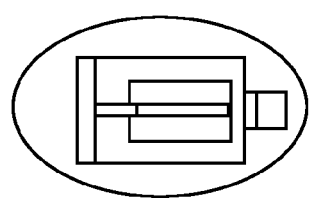

Another variation of a nested flap valve is shown in FIGS. 11A and B. In FIG. 11A the valve includes an inspiratory door 1103 (flap) portion that opens during inspiration, and an expiratory door 1101 portion built into the inspiratory door, that may open during expiration. Both the inspiratory door and the expiratory door are stiff members, and both are rectangular when viewed perpendicular to their faces, as shown in the top view of FIG. 11B. The passageway may be adapted to have a rectangular cross-section so that the valve can seat within the passageway and obstruct airflow through the passageway unless the doors are open. The dashed lines indicated by 1105 show the open position of the valve during inspiration. During inspiration, when the valves open, both the upper and lower flap valves open and move together. During expiration, only the nested expiratory door opens when the expiratory pressure across the door is greater than the threshold for opening, as indicated by the dashed lines 1107.

FIG. 12. shows another variation of the door-within-a-door type (e.g., nested) valve described in FIG. 11. This variation may be fabricated from an elastomeric material. In some variations, the doors of the valve are hinged using a living hinge as described, where the hinge regions are cut into the hinge shape to allow flexion. FIG. 12A shows a top view of the airflow resistor including this valve through the passageway. FIG. 12B shows a cross-section through the side of the airflow resistor, and FIG. 12C shows a bottom view from within the airflow resistor. An alternative top view is shown in FIG. 12D, in which a sealing face or ledge 1201 is included for the door to seal or rest against. FIG. 12E shows a cross-sectional view of the airflow resistor shown in FIG. 12D, and FIG. 12F shows a bottom view of the same airflow resistor.

Figure 20A:
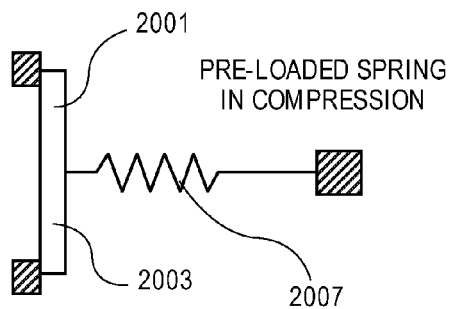
FIGS. 20A and 20B illustrate the operation of a rigid plate valve.
Figure 20B:
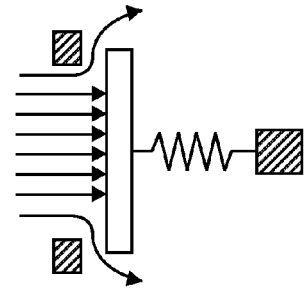
Figure 20C:
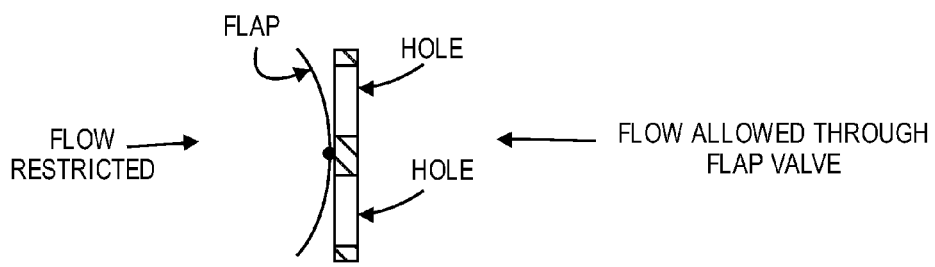
FIG. 20C shows a flap valve compatible for use with a plate valve.
Figure 20D:
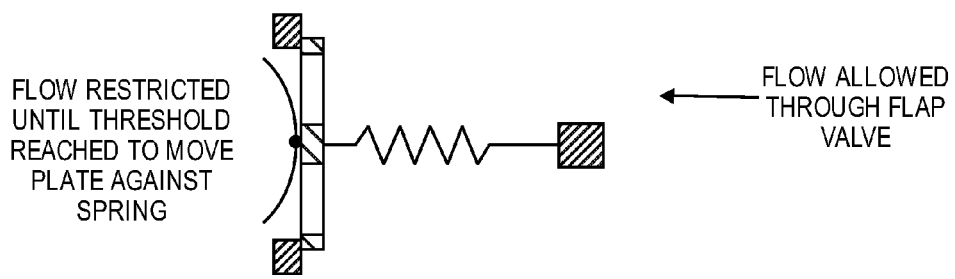
FIG. 20D shows a hybrid rigid plate and flap valve configured for use with a PEEP device, as described herein.

FIGS. 20A to 20D show an example of a valve appropriate for an airflow resistor of a PEEP device in which a flap valve is combined with a rigid valve. In FIG. 20A a rigid valve 2001 is biased against a valve seal region 2003. The bias 2005 is preloaded in compression so that it tends to hold the rigid valve against the valve seal. When the pressure acting on the rigid valve exceeds the force applied by the bias (e.g., the preloaded compressive force), the rigid valve is pushed away from the seal, opening to allow the passage of air around the rigid valve, as shown in FIG. 20B. Thus, in this example, the preloaded compressive force establishes the threshold pressure for opening. FIG. 20C shows a dual flap valve having two flaps covering two openings (holes). This flap valve is combined with the rigid and biased valve shown in FIGS. 20A and 20C to form a valve that may be configured to create PEEP, as shown in FIG. 20D.

Figure 20E:
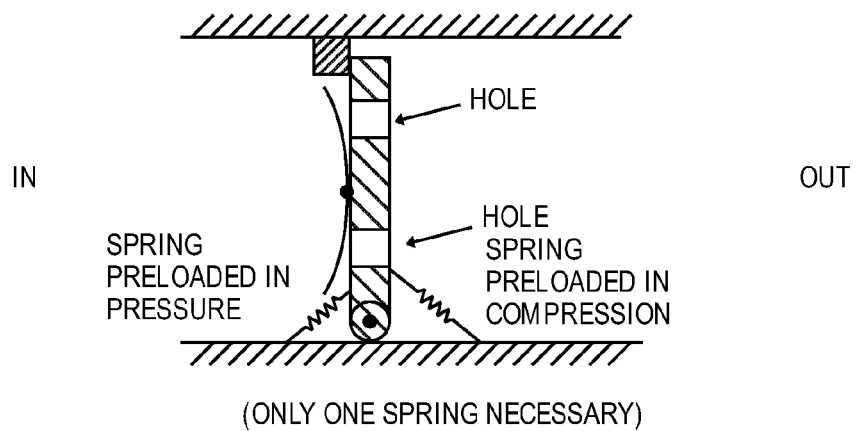
FIGS. 20E to 20G illustrate different variations of a hybrid rigid and flap valve similar to the valve shown in FIG. 20D.
Figure 20F:
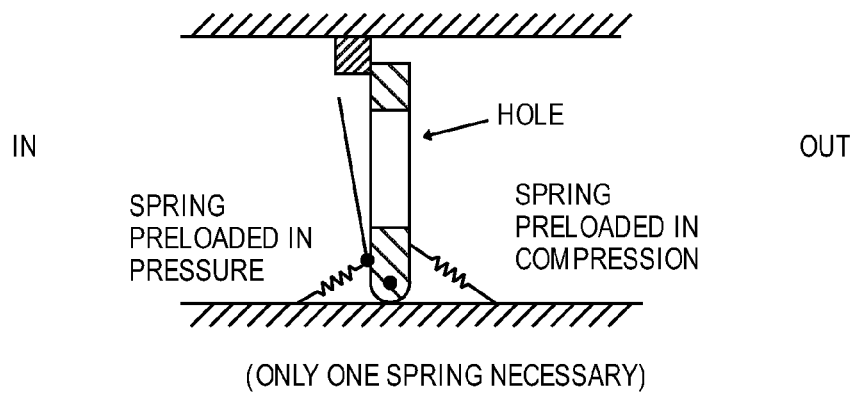
Figure 20G:
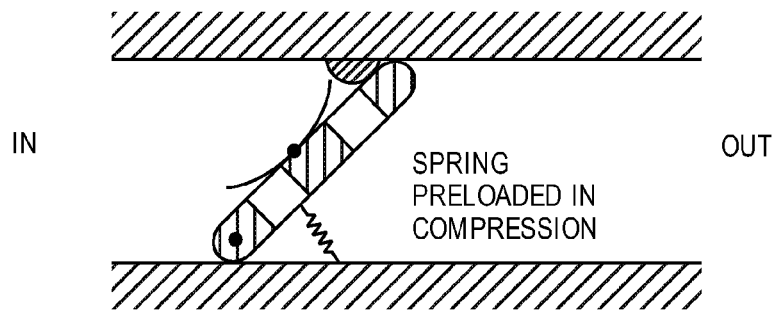

FIGS. 20E-20G show different variations of airflow resistors comprising valves that may be used as part of a PEEP device, similar to the biased flap valve shown in FIG. 20D. For example, in FIG. 20E, the rigid region of the valve is not biased at its center, but is instead biased so that it opens like a door (on one side). The rigid region of the valve also includes two biases, a bias for compression as well as tension. The combination of different biases may be used to more accurately control the resistance profile of the valve, and in particular, may be used to set the threshold for opening during expiration (e.g., flow 'out' of the device, as indicated by the 'in' and 'out' directions).

In FIG. 20F, the flap valve is also shown as a side-hinged valve. In general, a flap valve rotates around a fixed point when force is applied at some distance from that point, causing deflection of the flap relative to the point and/or mechanical deformation of the flap. Thus, a flap may be more easily opened by increasing the distance between the force applied to the flap and the flap attachment point (e.g., the moment arm). The moment arm may be increased (as shown in FIG. 20B) by increasing the movable area of the flap. In some variations the length of the moment arm may also be increased by increasing the distance between the hinge and the opening through which the force is applied. This may be achieved, for example, by building the flap valve so that it sits at an angle with respect to the passageway.

Figure 13A:
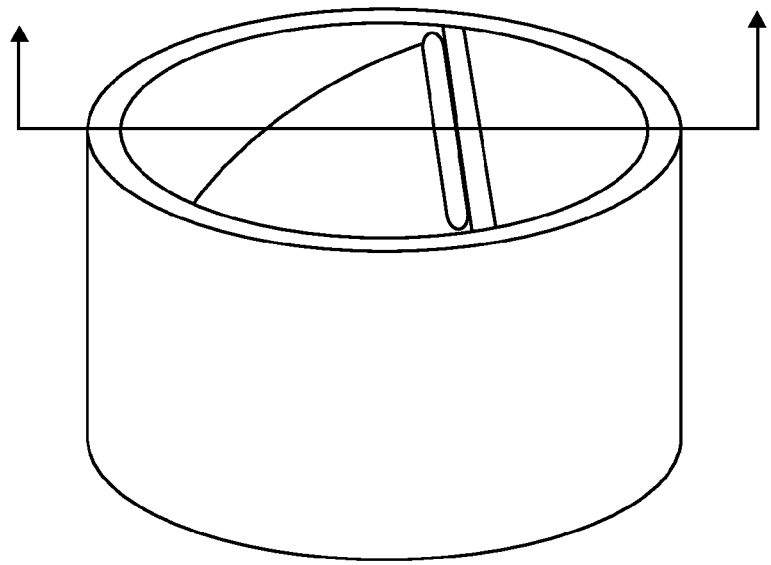
FIGS. 13A and 13B show perspective and cross-sectional views of a region of a respiratory device having two passageways.
Figure 13B:
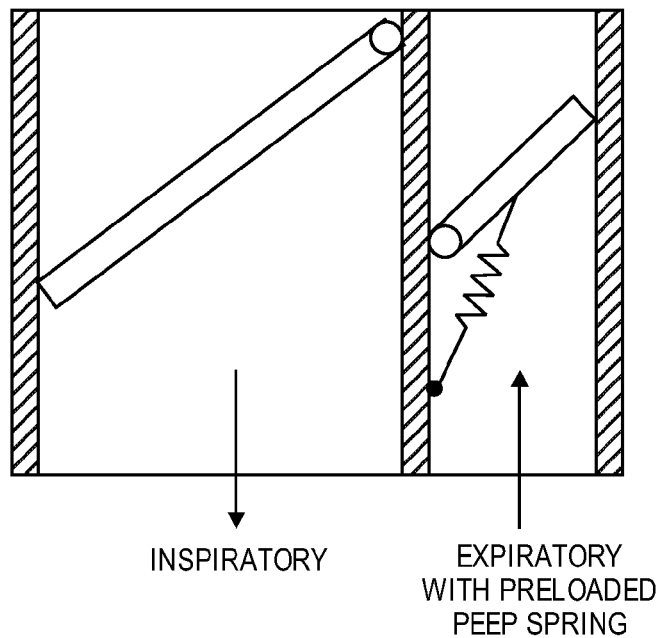

In some variations, the PEEP device may comprise more than one passageway, in which each passageway includes a valve. In this example, one passageway is used for inspiration, and one is used for expiration. For example, FIG. 13A shows a perspective view of a PEEP device having two passageways. A cross-sectional view is shown in FIG. 13B. The inspiratory side of the device includes a flap valve that readily opens during inspiration, but remains closed during expiration. The cross-sectional area of either passageway may be equal, or one of them may be bigger than the other (e.g., the expiratory passageway may be smaller than the inspiratory passageway). The expiratory side includes a biased valve (similar to the valves described above), which is set to open when the pressure across the device exceeds the threshold for opening. The bias 1301 shown in FIG. 13B is schematically indicated. One embodiment of this bias includes an elastomeric band (e.g., spring), as shown in FIGS. 14A-14D.

Figure 14A:
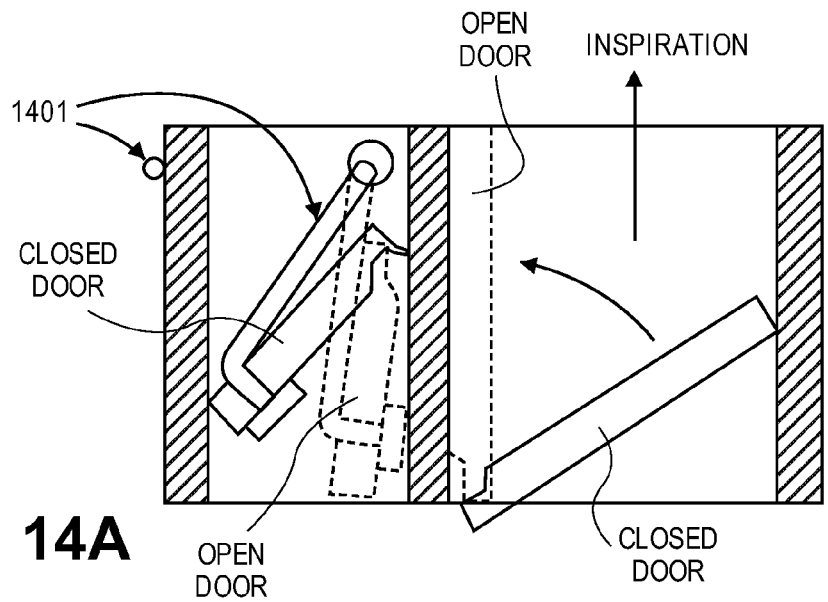
FIG. 14A shows a cross-sectional view of a region of a respiratory device having two passageways, as described.
Figure 14B:
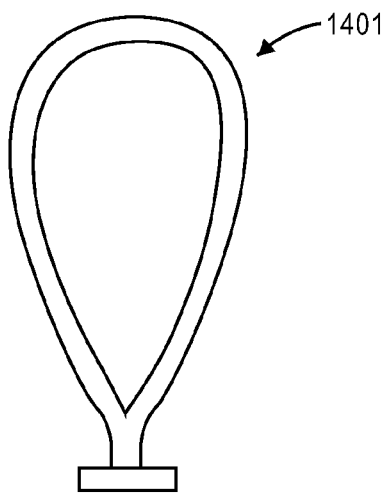
FIG. 14B shows an elastomeric component of the respiratory device shown in FIG. 14A.
Figure 14C:
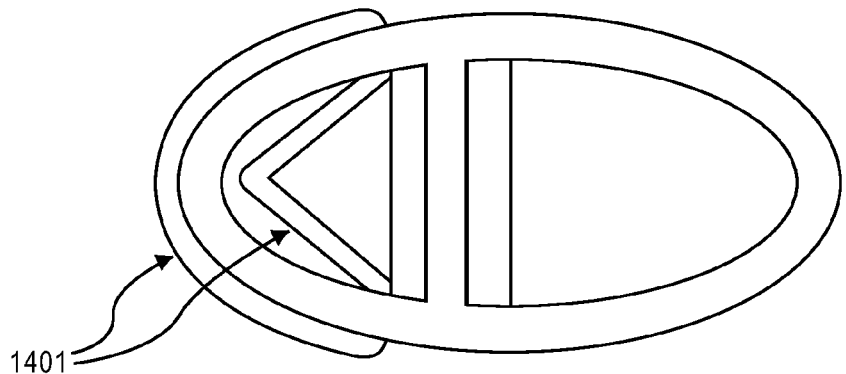
FIG. 14C shows a top view of the respiratory device shown in FIG. 14A

In FIG. 14, the PEEP device includes two chambers, as shown in the cross section shown in FIG. 14A. The elastomeric element 1401 (shown in FIG. 14B) is wrapped around the outside of the passageway after passing thorough holes on either side of the passageway to connect to the flap and bias it within the expiratory passageway. This is shown in FIG. 14C, in a top view of the closed expiratory valve. In this variation, the elastomeric element is attached by passing through a hole in the flap, where it anchors on the opposite side of the flap.

Figure 15A:
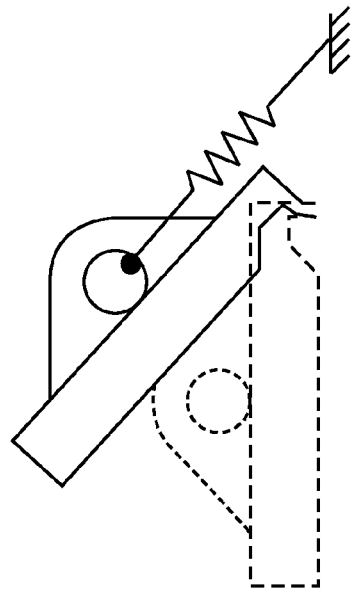
FIGS. 15A to 15C show different variations of an anchored bias that may be used with an expiratory flap valve as shown in FIGS. 14A-14C.
Figure 15B:
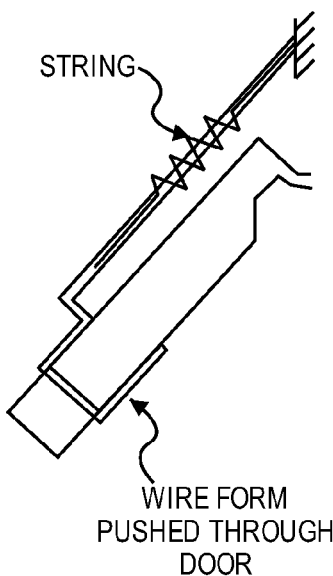
Figure 15C:
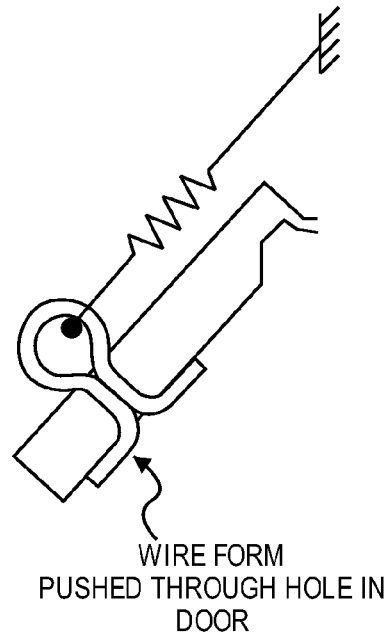

FIGS. 15A, 15B and 15C show alternative ways to anchor the bias (e.g., a spring or elastomeric element) to the expiratory flap valve shown in FIG. 14A-14C. In FIG. 15A a spring is anchored (e.g., via a hook) thorough a hole fabricated on the flap. In FIG. 15B, the bias is a wire that passes through the flap and anchors beneath it. In FIG. 15C, the bias connects to a loop of wire that is pushed through a hole in the door (flap).

Figure 24A:
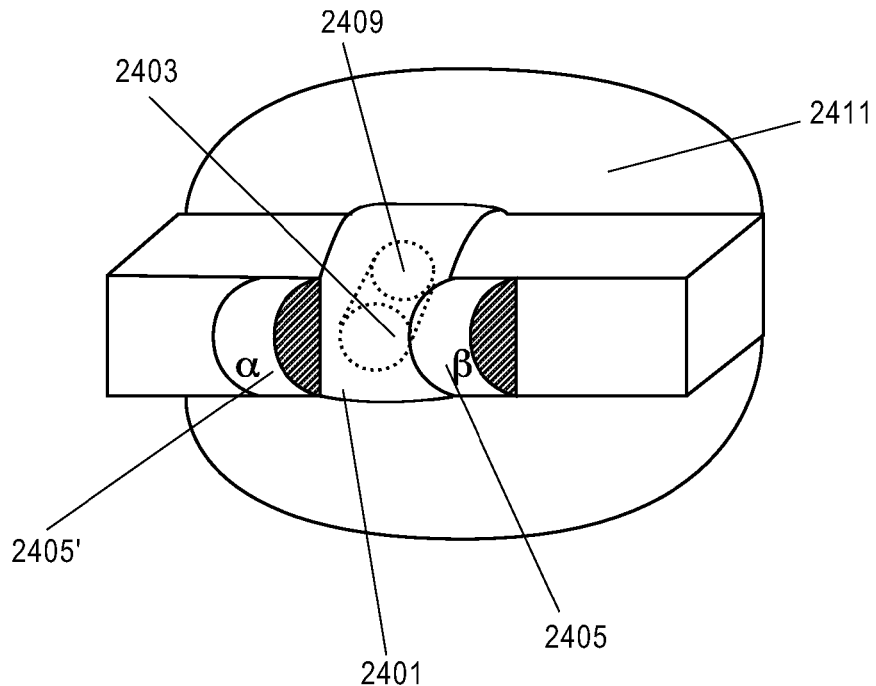
FIG. 24 illustrates another variation of a valve that may be included as part of a two or more passageway PEEP device.
FIG. 24B illustrates another variation of the valve shown in FIGS. 24A and 24B.
Figure 24B:
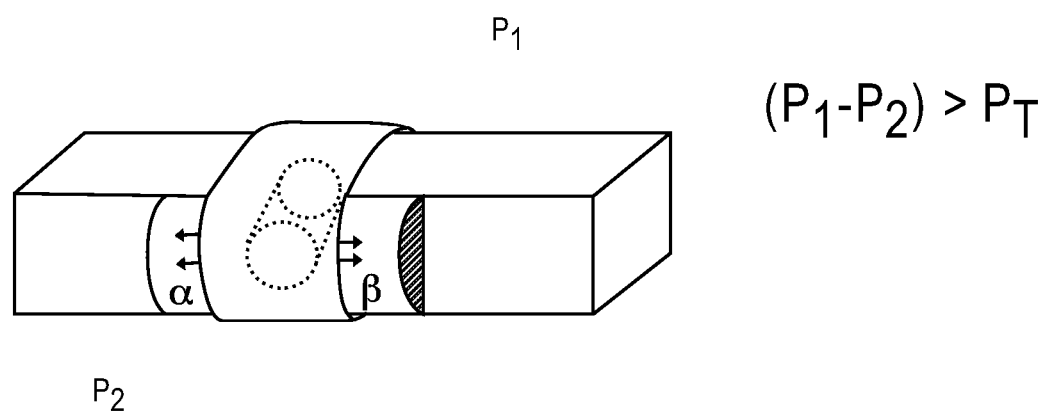

Anther variation of a valve that may be included as part of a two or more passageway PEEP device is shown in FIGS. 24A and B. In FIG. 24A, an elastomeric membrane 2401 is positioned over only one end of a passageway 2409, and other passageways may be substantially blocked off by an occlusive wall 2411 (for convenience, not shown in the additional FIGS. 24B to 24D). The membrane 2401 is positioned so that a threshold pressure ($P_T$) is required to displace the membrane from over an opening 2403. Airflow is therefore blocked until the elastomeric membrane is deflected, as shown in FIG. 24B. Thus, when the pressure differential ($P_1-P_2$) is reached in this variation, the membrane stretches beyond the reach of the structures 2405, 2405' conforming to the expansion path of the elastomeric membrane (e.g., the accommodating path surface). The threshold pressure may be determined by the membranes stiffness and the geometry of the airflow pathway, including the accommodating path surface, as described in more detail below. FIGS. 24C and 24D illustrate another variation of the valve shown in FIGS. 24A and 24B.

Figure 21A:
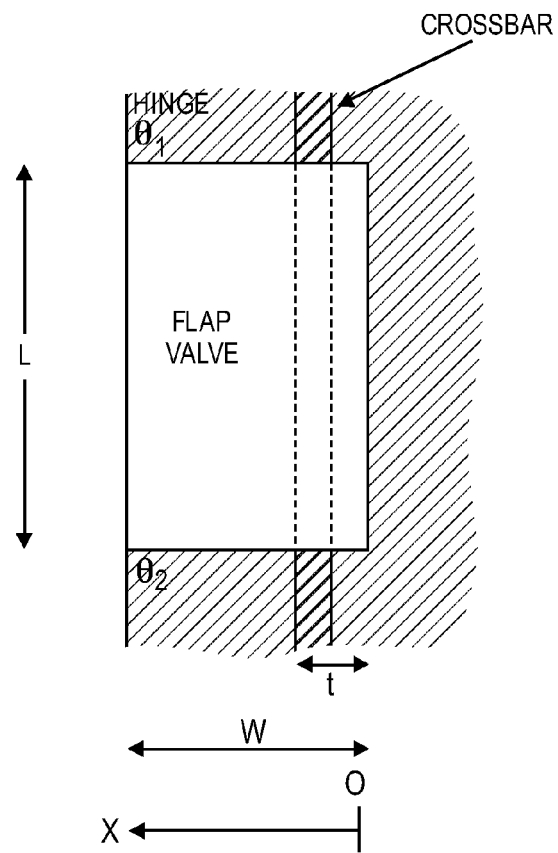
FIG. 21A shows a flap valve configured to have a pressure profile as shown in FIG. 3.

FIG. 21A shows one example of a valve that is not typically configured for PEEP, but that may be used in combination with a bias or with another valve to achieve PEEP. FIG. 21A shows a flap valve that is hinged on one side, and is constrained from opening during expiration (e.g., into the page), by a crossbar. During inspiration, the valve bends (out of the page), permitting airflow. In some variations, the flap valve bends everywhere along the length of the valve (e.g., $0 \leq x \leq w$). In other variations, bending during inspiration is focused on the area near the hinge (e.g., x approximately equal to w), and the flap may be reinforced elsewhere, or may comprise a more rigid material or greater thickness. The valve may be relatively easily opened during inhalation because of the relatively large surface area of the flap, and the large moment arm. During exhalation, the valve is constrained for easily opening by the crossbar, however, since there is no "preload" (e.g., bias) on the distal region of the flap, it will simply open a little with a little pressure, and more with greater pressure, resulting in a pressure profile similar to the profile shown in FIG. 3. In one variation, the flap is stiff, and the crossbar is an elastomeric material. Thus, the crossbar yields during exhalation to open the valve.

Figure 21B:
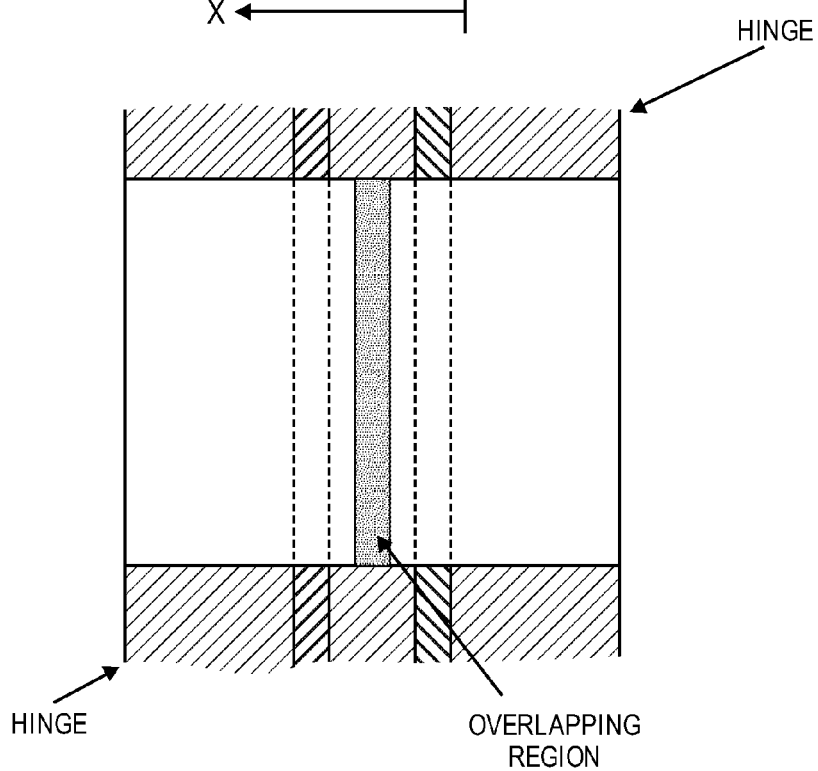
FIG. 21B shows another flap valve configured to have a pressure profile as shown in FIG. 3.

FIG. 21B illustrates another variation of a valve which may be used as part of a PEEP configured device. Two or more flaps (e.g., such as the flap shown above in FIG. 21A) may be arranged to overlap to provide a resistance profile having a threshold for opening. For example, in FIG. 21B two flaps are hinged, and each valve is constrained from opening during exhalation by a crossbar, similar to FIG. 2A. The flaps are arranged in an overlapping saloon-door configuration, so that there is an overlapping region between the crossbars. The flaps may open easily during inspiration, as described above for the variation shown in FIG. 21A. During expiration, the distal region of each flap (furthest from the hinge region) is constrained from opening at the region past the crossbar by overlapping region. The flaps may be continuously flexible (so that they can bend everywhere along their length) or relatively stiff. Thus, a PEEP resistance profile may result, since the two doors need to move a certain distance (providing a preload) before air can get by them.

Figure 22:
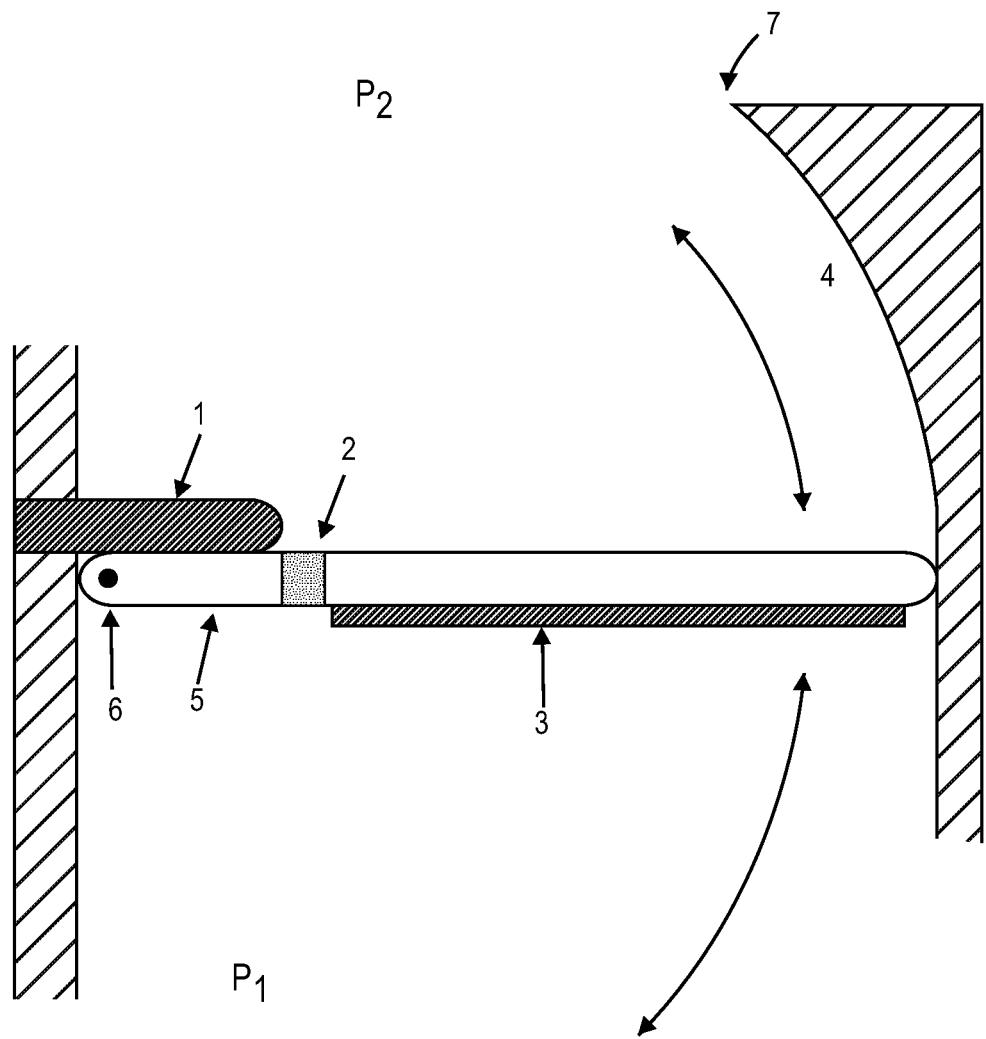
FIG. 22 shows another variation of a PEEP device having a resistance profile similar to that in FIG. 5.

FIG. 22 shows another variation of an airflow resistor including a valve that is configured to operate as part of a PEEP device having a resistance profile similar to that in FIG. 5. The valve includes a door 5 that is hinged 6 so that during inhalation, the door opens without much resistance (inhalation is airflow towards the distal direction, e.g., P2>P1). During exhalation, stopper 1 prevents the door 5 from rotating open beyond the set position. Further rotation of the door 5 in the direction of the exhalation (e.g., the proximal direction), requires bending around a hinge region 2 that is part of the door. This second hinge region 2 may resist bending because of material stiffness of the door, and/or contact between the door and the surface of the passageway region opposite of the door 4. The surface of the passageway opposite the door 4 in the proximal direction of the passageway (e.g., in the proximal direction) may be configured to prevent opening of the valve during exhalation as the door bends in the distal direction. Thus, in FIG. 22, the surface of the passage 4 is curved to prevent airflow during exhalation until the pressure across the valve (the pressure differential P1–P2) is large enough to push the end of the door 5 past the curvature of the wall 7 at the end of the curved surface 4. In the variation shown in FIG. 22, the door is augmented with a support 3 that stiffens it so that the door does not readily bend in this region. The support 3 may therefore help localize bending to the hinge regions, which may help prevent flow thorough the device until the door has passed the end of the shaped region of the passageway 4. The threshold for opening during expiration for this device may therefore be controlled by the flexibility of the second hinge region 2, the surface area of the door 5, and the geometry of the shaped region of the passageway 4. The shaped region is a path-accommodating surface that may interact with the flap or door of the valve. Thus, in this example, the valve is biased in the exhalation direction (P1>P2) by the stiffness of the second hinge region 2, which must bend a preset amount (along the curved passageway 4) before the valve can open.

The device shown in FIG. 22 is also adjustable. In particular, the threshold for opening during exhalation is adjustable. For example, the stopper 1 maybe adjusted by moving it further into or out of the passageway. In one variation, the stopper is threaded so that it may be screwed further into or out of the passageway. Adjusting the length of the stopper within the passageway may affect the ability of the door 5 to deflect during exhalation. For example, adjusting the length of the stopper may reduce or increase the curvature of that the door bends with, which may increase or decrease interference around the shaped region of the passageway 4. The stopper length may also determine how much of the second hinge region 2 is available to bend.

Figure 23A:
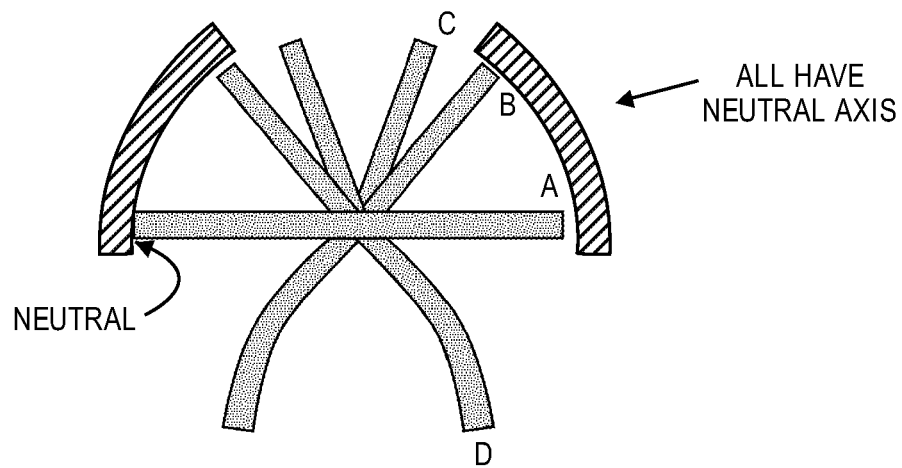
FIG. 23A and 23B illustrate a portion of a valve having a path accommodating surface that helps to regulate the resistance profile of the valve similar to that in FIG. 5.

FIG. 23A illustrates the general use of a path accommodating surface to regulate the resistance profile of a valve. In FIG. 23A, a cross-section though a flap and path accommodating surface shows that the flap in four positions. In the first (neutral position), indicated by position A, the flap blocks off both inhalation (by convention, in the downward or distal direction of the figure as drawn), and exhalation (by convention, upward or proximal in the figure as drawn). During inhalation the valve readily moves out of the way, forming a space between the wall of the passage in the distal direction, and the valve through which air may flow, as shown in position D. However, during exhalation, the walls of the pathway conform to the movement path of the valve in the proximal direction. Thus, the space between the flap(s) and the wall is limited, as shown in position B, until the flaps pass the conforming region, shown in position C. When the flaps are in position C, air may pass through the device during exhalation. Thus, a valve having an accommodating path surface may have resistance profile similar to that shown in FIG. 5.

Figure 23B:
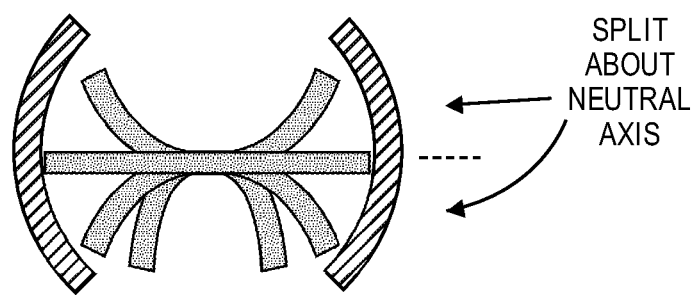

An accommodating path surface may also be adjusted by adjusting the distance between the path (e.g., wall) surface and the flap, as well as the extent to which the wall is an accommodating path surface. FIG. 23B shows a variation in which the accommodating path wall surface has been split around the neutral position, as shown.

Figure 17A:
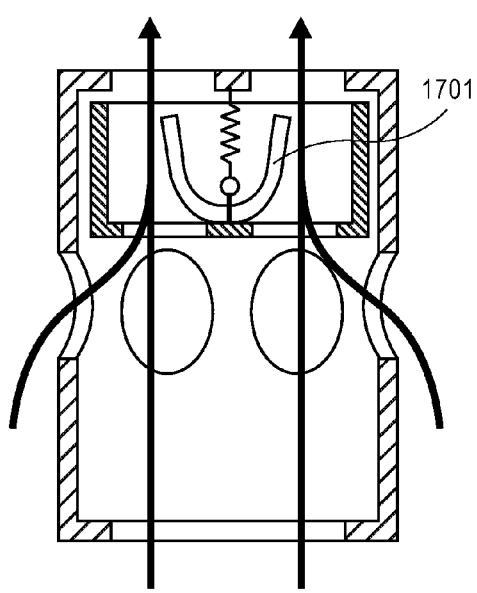
FIGS. 17A to 17D illustrate the operation of a respiratory device configured for PEEP.
Figure 17B:
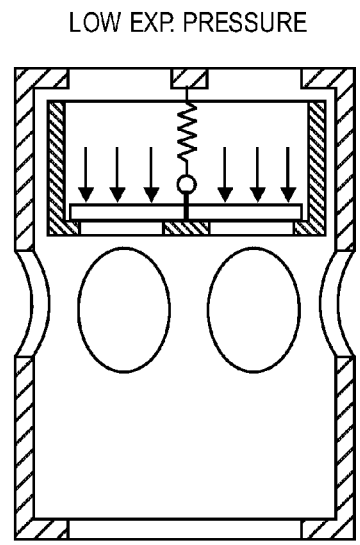
Figure 17C:
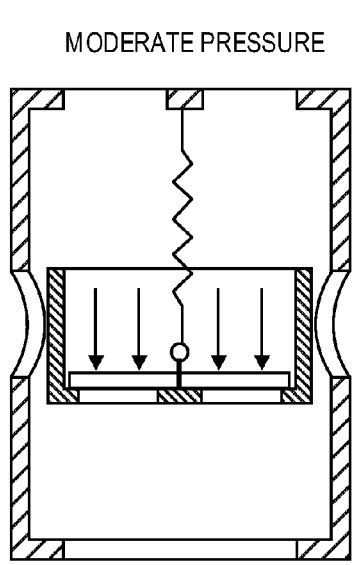
Figure 17D:
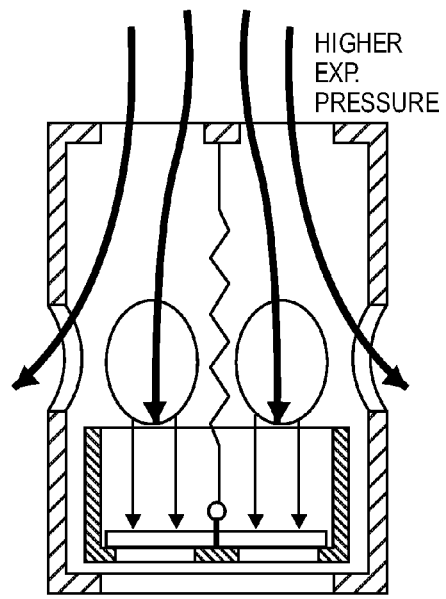
Figure 17E:
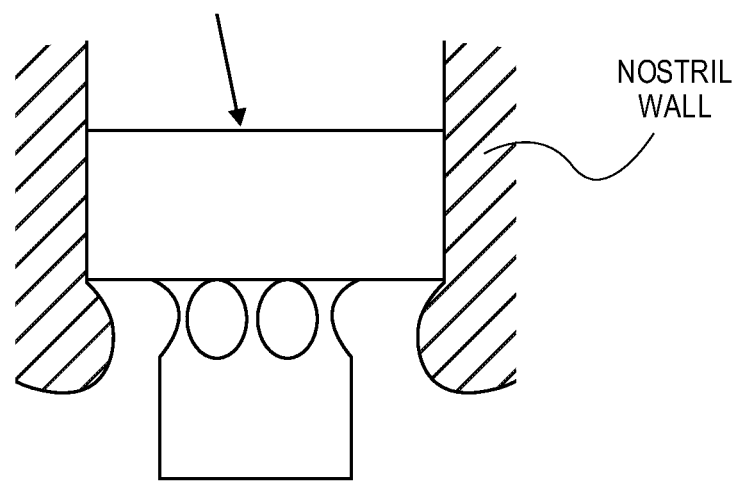
FIG. 17E shows a profile of the device illustrated in FIG. 17A-17D within a nasal cavity.

FIGS. 17A-17D show another variation of a PEEP device. This PEEP device includes an airflow resistor that comprises a platform that moves based on expiratory pressure against a bias. The bottom of the platform comprises a flap valve that is open during inspiration, but closed during exhalation. For example, FIG. 17A show the valve during inhalation, in which the flap valve 1701 (e.g., a silicone flap valve) is open as air is drawn up the valve. In the neutral position, or during very low pressure exhalation, the flap valve 1701 is closed, and the platform is biased (e.g., by the spring or elastomeric material) so that expiratory flow does not pass (e.g., from the top of the figure down). At moderate expiratory pressure the platform moves against the bias as shown in FIG. 17C, however the platform walls block the exit holes through the passageway, so airflow is still not possible. Once the expiratory pressure across the device is greater than the threshold for opening the valve (determined in part by the bias and the geometry of the platform), the valve opens, allowing respiratory airflow, as shown in FIG. 17D. FIG. 17E shows a side view of what this device might look from while in a subject's nostril.

Any of the respiratory devices described herein (including the PEEP configured devices) may be dual-nostril devices that cover both nasal cavities, or they may be configured for use in a single nostril. If they are configured for use in a single nostril, each device may include one or more valves to control airflow, as described above. In many variations, it may be beneficial to configure the respiratory device so that both nostrils are combined into a common lumen through which respiratory airflow is regulated. There is a limited cross-sectional area within each nostril with which to provide low resistance during inhalation and higher resistance during exhalation using the valves and vents as described herein. The effective cross-sectional area may be increased by extending the device to the region just outside of the nostril and/or combining the nostril passageway into one effective passageway. This passageway could span the area between the nares of each nostril, above the subject's lip.

Figure 25:
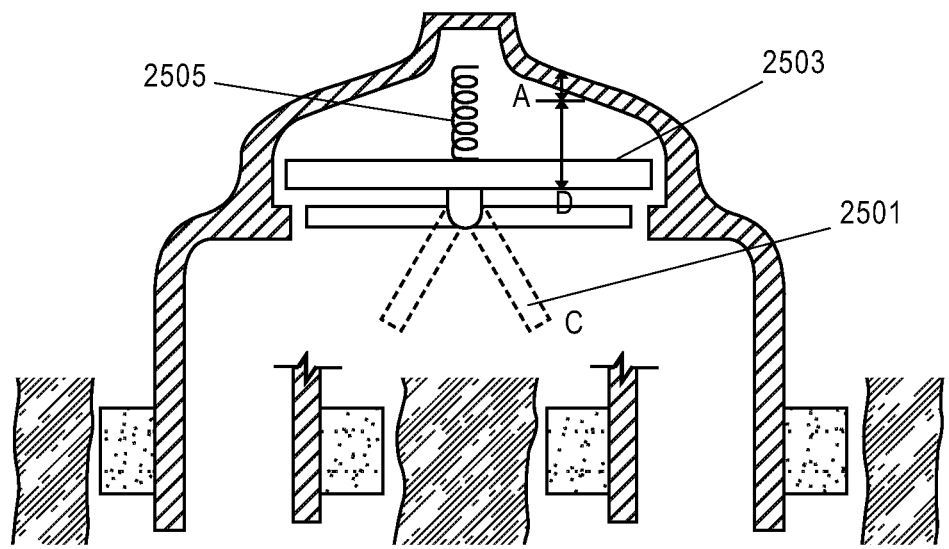
FIG. 25 shows a respiratory device combining airflow through both nostrils, as described herein.
Figure 25:
Figure 25:
Figure 25:

For example, a respiratory device combining airflow through both nostrils is illustrated in FIG. 25. This device is configured for PEEP, and includes a hybrid flap valve 2501 and a biased rigid disc 2503. The device is shown inserted into both nasal passageways. During inhalation, the flaps 2501 of the flap valve move from a neutral position (B) to a flap open position (C) allowing air to flow from the outside environment into the nasal cavity with very low resistance. The rigid valve 2503 (to which the flap valve is shown attached) is biased against a valve seal (or seat) by a biasing element 2505. For example the biasing element may be a spring such as a compression or leaf spring made of metal or plastic. During expiration at low pressure, the device is sealed. At high expiratory pressures, the disc lifts, e.g., moving from the neutral position (B) to an open position (A), allowing airflow through the device. In this example, since the airflow into and out of the valve is centrally located, only one valve (e.g., one hybrid valve) is required, instead of one per nostril.

FIGS. 29 to 32 show additional examples of valves that may be incorporated into a PEEP configured device, because they can have resistance profiles similar to the resistance profile in FIG. 5, which has a low resistance to airflow during inspiration and a threshold for opening during expiration.

Figure 29:
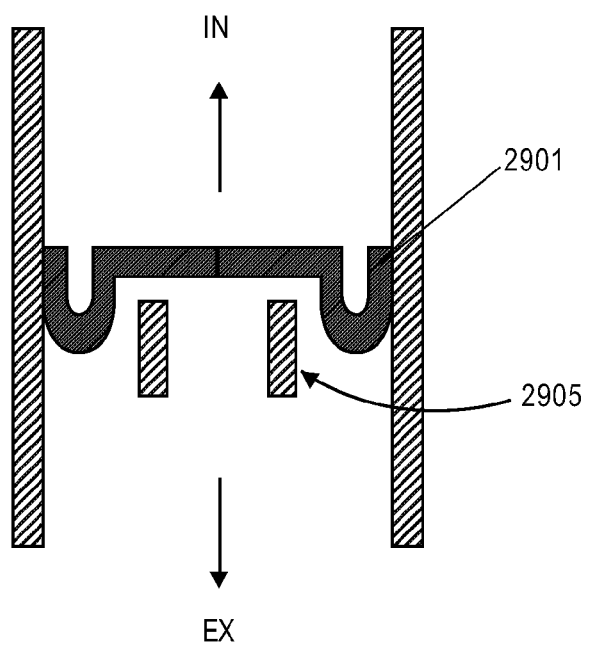
FIG. 29 shows a variation of an airflow resistor having a rolling hinge for use with any of the devices described herein.

FIG. 29 shows a valve having a rolling web or hinge. The valve is shown in the neutral position. During inhalation (indicated by the upward arrow), the pressure across the valve opens the flaps forming the rolling hinge 2901 allowing airflow with relatively low resistance. During exhalation, the flaps are closed, and the rolling hinge and flaps are propelled down (shown by arrow labeled "Ex") until the flaps contact the brace or braces 2905. When the pressure of exhalation exceeds the threshold for opening, the flaps bend to allow airflow across the valve. In some variations, the brace 2905 shown is not needed.

Figure 30:
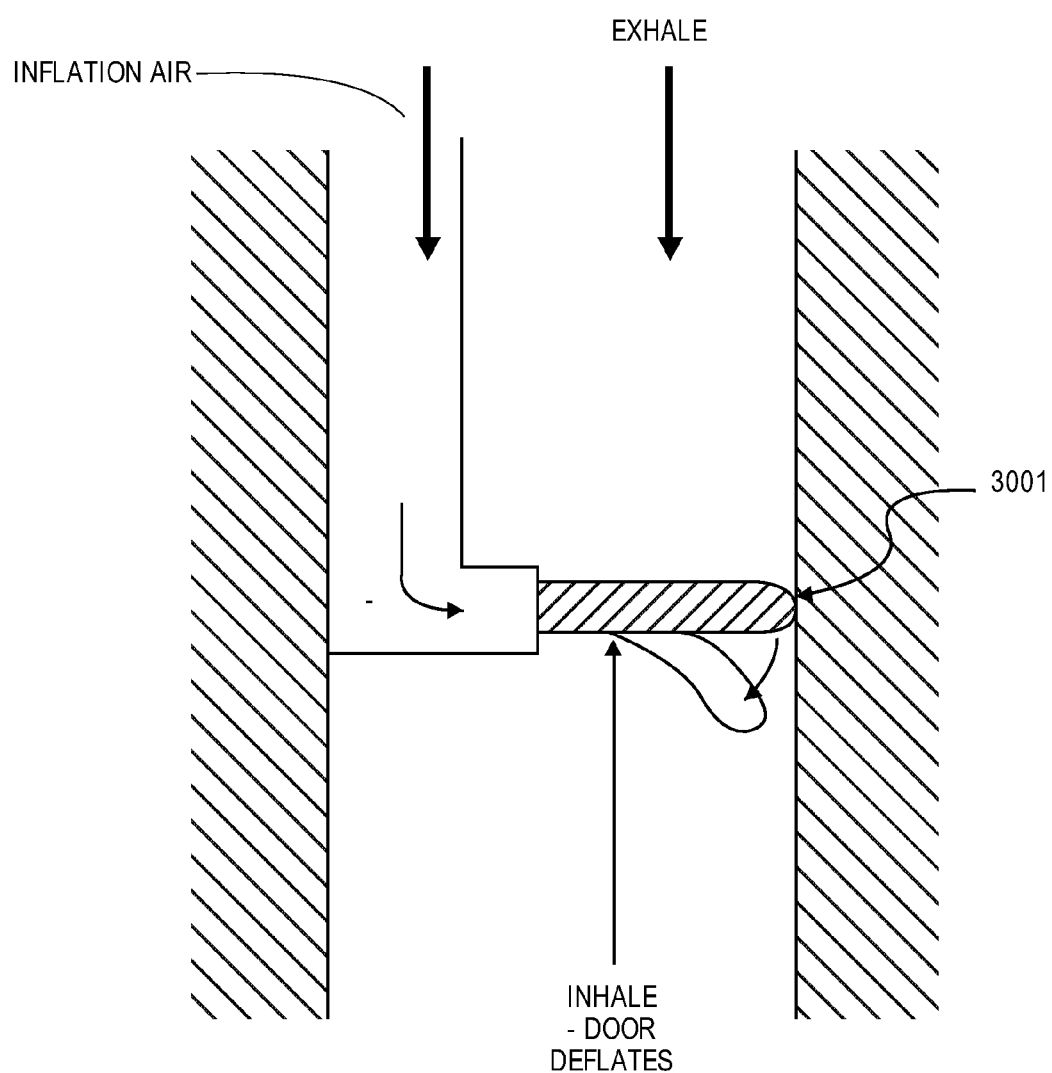
FIG. 30 shows a variation of an airflow resistor having an inflatable flap for use with any of the devices described herein.

The device shown in FIG. 30 includes an inflatable flap 3001 that is inflated during exhalation. During inhalation the flap is substantially un-inflated, and loose, and therefore readily moves to allow airflow. During exhalation, pressure from the distal end of the device (from a subject's lungs) moves down the passageway, and also down the inflation passageway shown on the left side of the passageway. Low pressure exhalation may be sufficient to inflate the bladder-like flap (which may comprise a thin elastomeric material, for example), causing it to extend across the passageway, preventing airflow. Although the flap is extended at higher pressure exhalation as well, at a threshold for opening, the pressure across the valve will cause the inflated flap to bend, allowing airflow with lower resistance. In some variations, the inflatable flap also includes a bias assisting it to inflate across the passageway.

Figure 31:
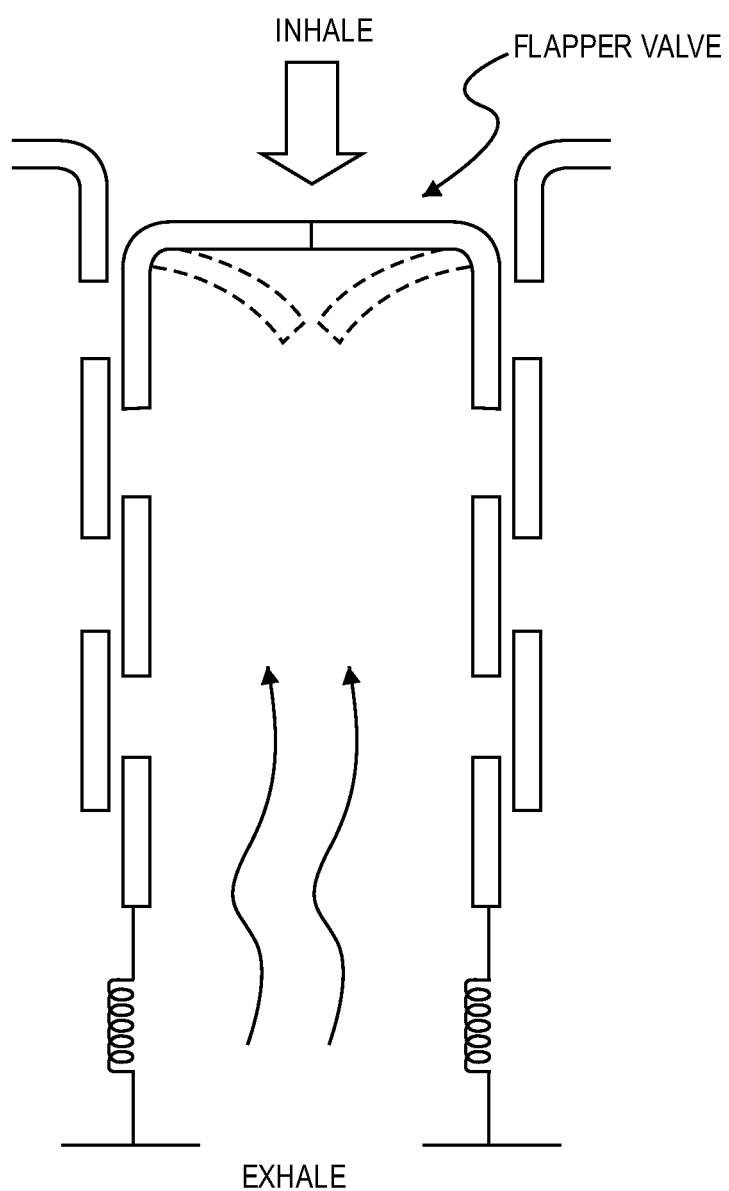
FIG. 31 shows another variation of an airflow resistor for use with any of the devices described herein.

FIG. 31 shows a valve device similar to the device shown in FIG. 17. The valve includes a combination flap valve (which opens during inhalation to permit airflow, but is closed during exhalation), and a sliding member attached to a bias. The sliding member includes holes along the sides. During low-pressure exhalation, the bias prevents the sliding member from sliding within the passageway. Higher pressure exhalation (e.g., pressure exceeding the threshold for opening) moves the sliding member up (as shown in the figure), allowing the holes in the sliding member to overlap with holes through the passage. Air may therefore flow through these holes to exit the device.

Figure 32:
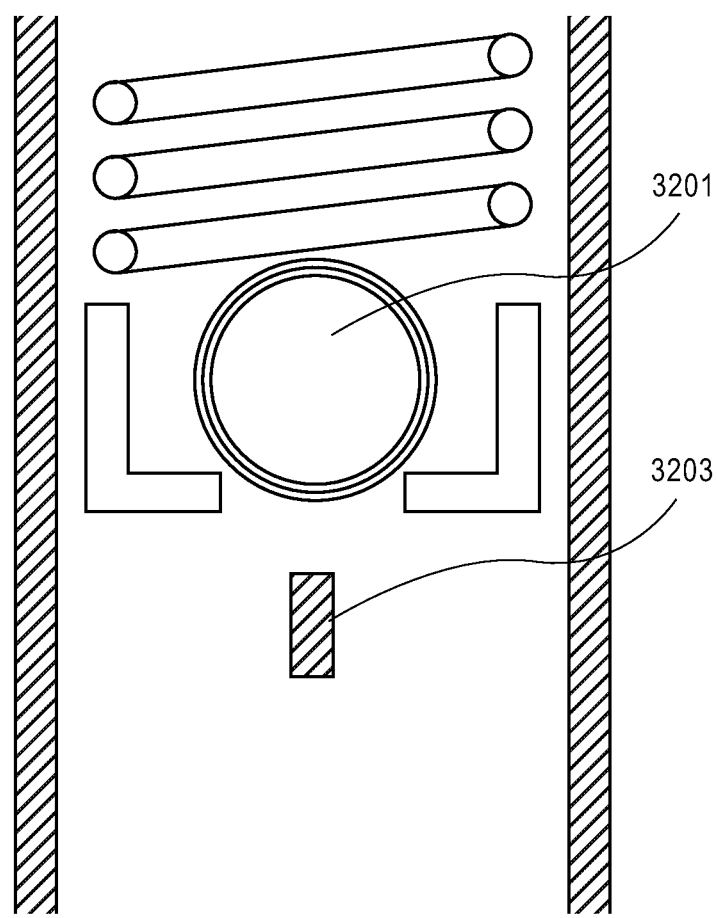
FIG. 32 shows a variation of an airflow resistor having ball valve and a slider, for use with any of the devices described herein.

Another variation of a sliding device is shown in FIG. 32. The PEEP device shown in FIG. 32 includes an airflow resistor that combines a ball valve with a biased slider. During inhalation the ball valve 3201 is displaced out of the way, permitting air to flow with low resistance through the passageway. During exhalation at low pressure, the ball 3201 blocks the opening in the passageway and the slider element is prevented from moving forward by a biasing element (shown as a spring in cross-section), so that there is little substantial airflow. At higher pressure exhalation (again, when the pressure across the valve exceeds the threshold for opening the valve) the slider moves against the bias towards the post 3203 in the central region of the passageway. The ball 3201 is eventually pushed out of the way by the post 3203 as the slider is pushed further forward, opening the passageway so that airflow may pass around the ball during high pressure exhalation.

Although these examples show airflow resistors including valves and devices that may be configured for use as a PEEP device having a resistance profile similar to the profile shown in FIG. 5, additional devices and variations of these devices may also be used. Furthermore, device having both a threshold for opening during exhalation, as well as a threshold for closing during exhalation may also be used. These devices may have a resistance profile similar to that shown in FIG. 6.

B. Differential Resistance Devices with a Threshold for Closing During Expiration Devices having both a threshold for opening during exhalation and a threshold for closing during exhalation may also be used as part of a PEEP device. In particular, these devices may include bistable valves. Bistable valves are valves that have more than one (e.g., two) 'stable' or neutral positions. Force or pressure may convert these devices between neutral positions. Thus, a valve may be configured with a bistable element so that the first stable portion regulates airflow during inhalation, and the bistable element in the second position regulates airflow during expiration. An example of this general concept is shown in FIG. 33A-33D.

Figure 33A:
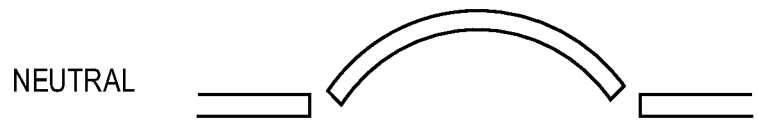
FIGS. 33A to 33D illustrate the operation of a bistable valve.
Figure 33B:
Figure 33C:
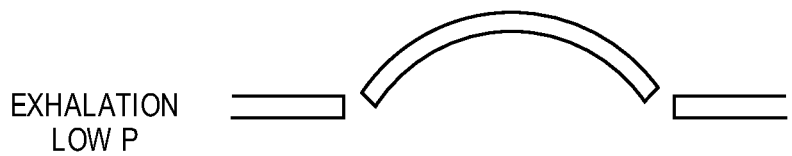
Figure 33D:
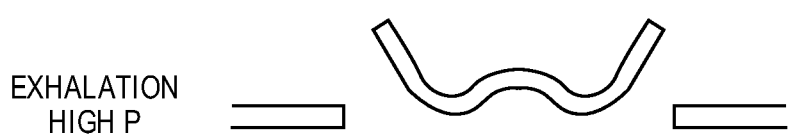

In FIG. 33A, a valve comprising a bistable flap is shown in the neutral position (e.g., between inspiration and expiration). The flap is shown as a curved surface. During inhalation, the curve may be further bent with very low resistance, so that airflow may occur during inhalation with very low resistance, as shown in FIG. 33B. During low pressure exhalation (shown in FIG. 33C), the flap remains in the curved position similar or identical to the position shown in FIG. 33A. Once the pressure increases to a predetermined point (e.g., the threshold for opening, the bistable flap opens, converting to a new stable position, as shown in FIG. 33D, opening to allow airflow therethrough. Once the flap is opened, however, it does not automatically return to the initial stable configuration (e.g., the neutral position shown in FIG. 33A or 33C). If the pressure across the valve falls below the threshold for opening. Instead, the flap may remain in the second stable position (e.g., open) until the pressure falls below a second threshold (e.g., the threshold for closing the valve during exhalation). As describe above, this relationship is described by a pressure profile similar to the on shown in FIG., 6.

Figure 34:
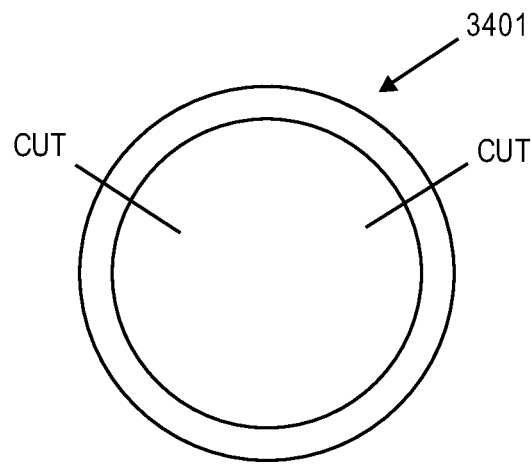
FIG. 34 illustrates one method of making a bistable valve, as described herein.

Typical bistable elements include relatively stiff or pre-biased materials and shapes. For example, a pre-curved stiff metallic or polymeric material may be suitable as a bistable flap. FIG. 34 shows one example of a how a bistable flap may be easily produced. In FIG. 34, a cylindrical material is cut to form a flap for use as part of a bistable valve 3401. Any appropriate material may be used to form these flaps, particularly material having some inherent or structural stiffness.

Figure 16A:
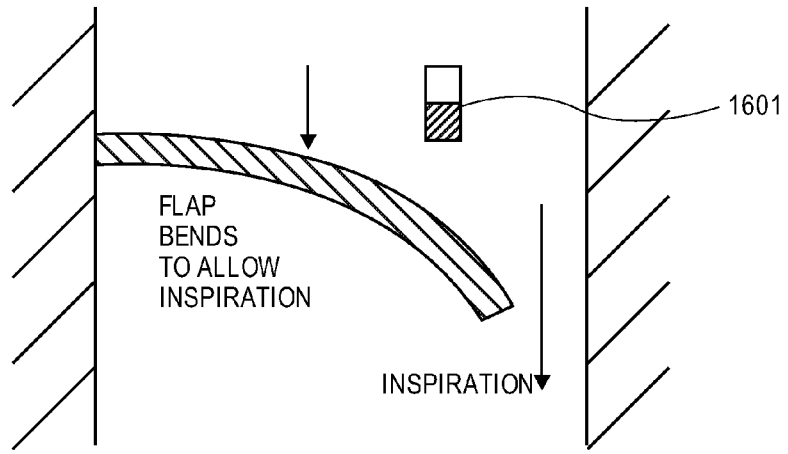
FIGS. 16A to 16C illustrate the operation of one variation of a device configured for PEEP.
Figure 16B:
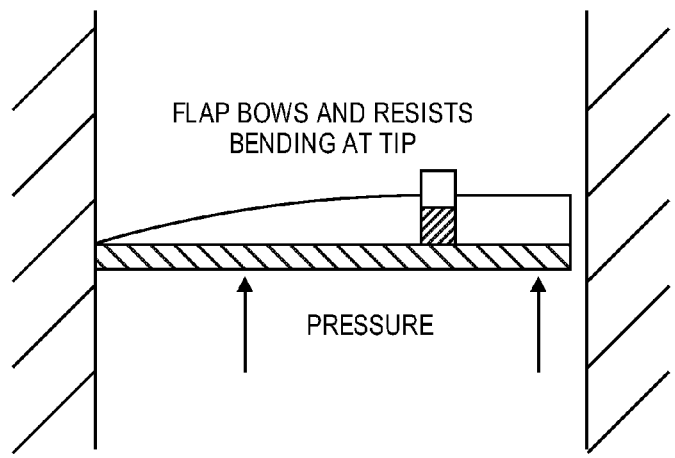
Figure 16C:
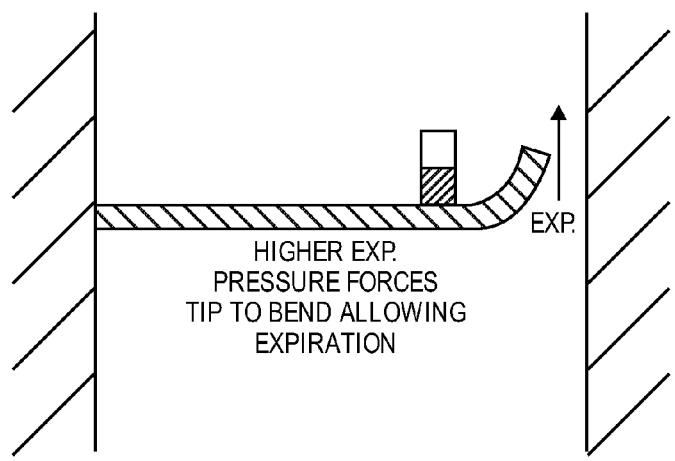

A PEEP device may achieve a resistance profile similar to that shown in FIG. 6, when the valve includes a bistable flap. FIGS. 16A-C show one variation of such a device having a resistive profile similar to that shown in FIG. 6. The valve comprises a bistable flap that is free to open during inhalation (shown here in FIG. 16A as a downward bending). At rest the flap is flat. During exhalation at low pressure (up in FIG. 16B), the flap may have a curvature (somewhat like a fingernail) when it is forced against the crossbeam 1601 (also called a cross strut), as shown in FIG. 16B. During exhalation at low pressure (up in FIG. 16B), the flap valve is prevented from opening by both the crossbeam 1601 and because the flap has a predetermined stiffness. This stiffness may arise because of a combination of the material stiffness for the material from which the flap is formed (e.g., a stiff elastomeric material), as well as the shape into which the material is formed (such as a curved structure). Bistable shapes are described in greater detail below. In FIGS. 16A-16C, it is difficult to bend the region of the flap distal from the hinge region and the crossbeam. In order to open, the valve must bend over the beam as shown in FIG. 16C (shown as upward bending).

Figure 26:
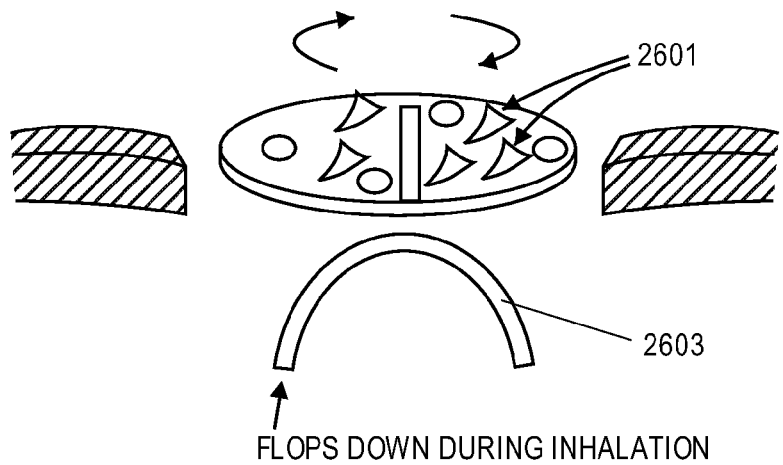
FIG. 26 shows another variation of an airflow resistor for use with any of the devices described herein.

In addition to bistable valves, other valves may also have both a threshold for opening during exhalation and a threshold for closing during exhalation. For example, FIG. 26 illustrates a valve that includes a flap 2603 that opens during inhalation allowing air to pass through holes on the plate 2601, and rotating the plate (configured as a disk) to move it down into a seal or seat. During exhalation, the flaps seal against the disk, and the pressure of the exhalation drives the disk 2601 to rotate in the opposite direction it rotated during inhalation. Rotation is driven by the high-resistance airflow passing along the edge of the disk or through channels on the disk. As the disk rotates it moves up (during exhalation, or down during inhalation). Once the disk reaches a predetermined height, the resistance to airflow during exhalation decreases, since air is allowed to pass around the sides of the disk more easily. Inhalation resets the disk by rotating it back down.

Figure 27:
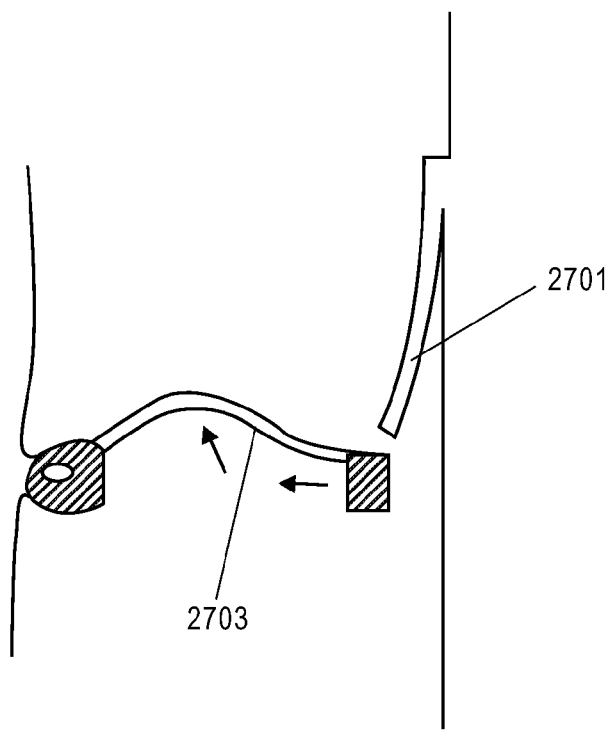
FIG. 27 shows another variation of an airflow resistor for use with any of the devices described herein.

FIG. 27 show a valve with a threshold for opening and a threshold for closing, and a profile similar to the resistance profile shown in FIG. 6. In FIG. 27, the valve is a flap 2703 that moves easily during inhalation to allow airflow at low resistance. The flap may be hinged at one end. In some variations, the flap is flexible (and may therefore bend over its entire length), while in other variations the flap is relatively stiff and bends most easily at the hinge region. During exhalation, the edge region of the flap is constrained from opening (e.g., in the upward direction in FIG. 27) by the rim or edge 2701 (e.g., shown as a projection 2701 in FIG. 27) along one side. When the pressure across the flap is strong enough to move the flap past this edge 2701 (the threshold for opening), the flap bends upwards, allowing flow across the valve.

Figure 36:
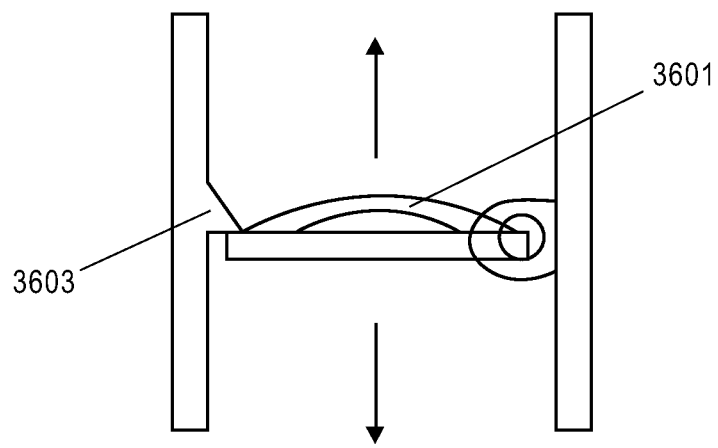
FIG. 36 shows another variation of an airflow resistor for use with any of the devices described herein.

In the variation shown in FIG. 27, as the pressure across the valve during expiration falls, the edge of the flap contacts the rim 2701, again cutting off flow through the valve (at the threshold for closing). The valve is fully reset by inhalation, which may drive the valve flap behind the edge 2701 once again. Another variation of the valve shown in FIG. 27 is shown in FIG. 36.

Figure 28:
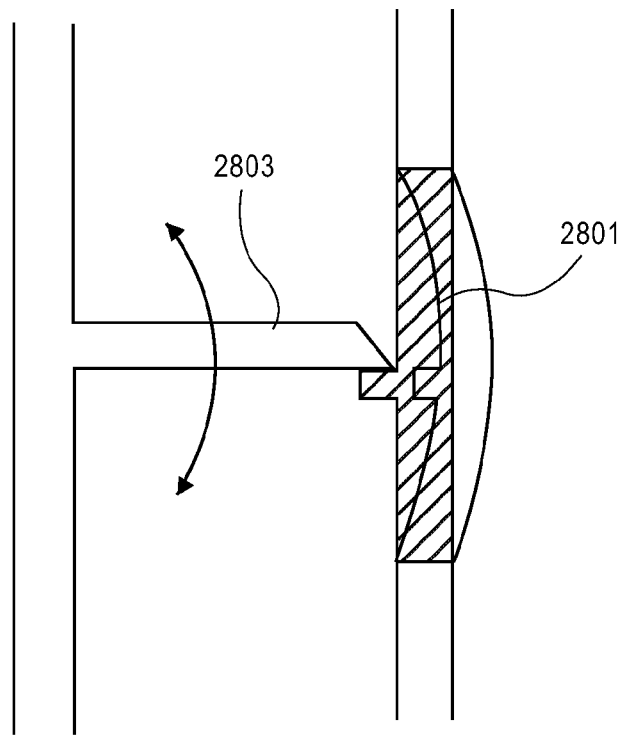
FIG. 28 shows a variation of an airflow resistor having an expandable wall for use with any of the devices described herein.

In FIG. 28, a flap valve 2803 is anchored to one side of the passageway. In this variation, the flap is relatively rigid (or stiff) across the length of the flap. The valve allows the passage of airflow with low-resistance during inhalation, because the flap moves upward, permitting air to pass. During exhalation at low pressure, the flap rest or is seated on a lip or rim on the opposite side of the passageway from where the flap is hinged. The portion of the passageway wall 2801 attached to this lip comprises a flexible or expandable material (e.g., an elastomeric material) and is configured to be unconstrained (e.g., not covered by a holdfast) so that the outside of the elastomeric region of the passageway 2801 is exposed to atmospheric pressure. As the pressure across the portion of the passageway wall 2801 increases during exhalation, the expandable region of the passageway 2801 is forced outwards, moving the lip or rim away from the flap, and permitting the flap to open (at the threshold for opening). Once the flap has opened, the flap will remain open even at relatively low pressures, unless there is an additional bias opposing the opening of the valve during expiration. If this bias is included (not shown), it would set the threshold for closing, as shown in FIG. 6. Otherwise, the valve would not be reset until inhalation drove the flap back past the lip or rim 2801. In this case, the resistance profile may resemble that of FIG. 7.

Figure 35:
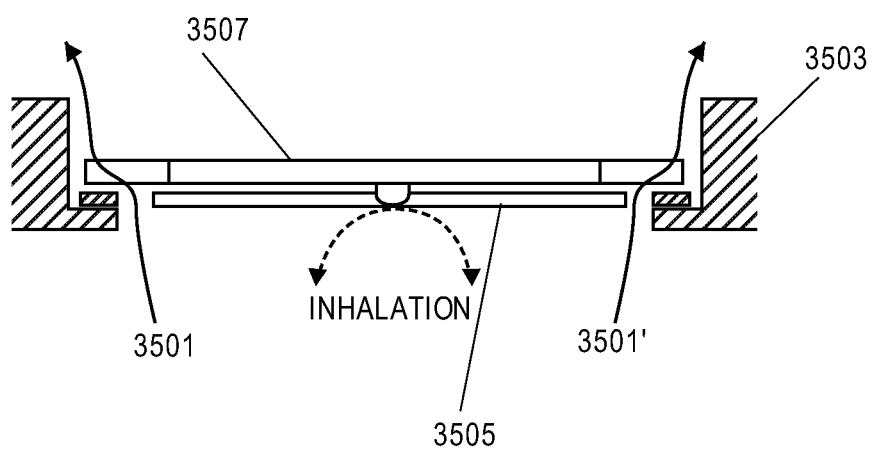
FIG. 35 shows a variation of a valve for use with any of the devices described herein.

FIG. 35 shows another example of a valve having a threshold for opening and a threshold for closing during exhalation. In FIG. 35, the valve comprises a flap 3505 and a plate 3507. As described in many of the devices above, the flap valve opens with low resistance during inhalation so that air may flow through holes on the plate 3507 and thus through the device. During exhalation the flap closes, preventing substantial airflow through the holes. Instead, pressure across the valve pushes the rigid plate 3507 upwards. A similar design was seen for the valve in FIG. 20A-20D, however the rigid plate in that valve was biased to prevent movement at low pressure during exhalation. In FIG. 35, the rigid plate includes an adhesive or magnetic force that must be overcome before the plate can be moved upwards, allow airflow though the device. FIG. 35 shows a magnetic or otherwise adhesive region 3503 between the rigid plate 3507 and the lip or seal region of the device on which the rigid plate 3507 rests. During high-pressure exhalation the adhesion (e.g., magnetic adhesion) between the plate and the rim is ruptured, allowing the plate to move upwards, opening a low-resistance pathway for airflow 3501, 3501'. This device may have a resistance profile similar to the profile shown in FIG. 7, for example.

Time dependency of the Device

As mentioned briefly above, the devices described herein may also be configured to have a time-dependent response. For example, it may be desirable to delay the response of the change in resistance based on the time point of the respiratory cycle. In one variation, a PEEP device may delay closing the valve after switching from inhalation to exhalation, even though the respiratory pressure is relatively low across the valve. Delaying switching to high resistance may allow the user to accommodate to the device more easily, enhancing comfort, and possibly aiding with compliance. In some variations, the devices described herein are configured so that airflow through the device is not substantially inhibited until some set time (e.g., less than 0.1 sec, less than 0.2 sec, less than 0.3 sec., less than 0.5 sec., less than 1 sec., etc.) or some percentage through a portion of the respiratory cycle. For example, the device may not provide a high resistance to low-pressure exhalation until approximately one-third or halfway through the expiration cycle (or 5% through the expiration cycle, 10% through the expiration cycle, 15% through the expiration cycle, 30% through the expiration cycle, 40% through the expiration cycle, 50% through the expiration cycle, 60% through the expiration cycle, 70% through the expiration cycle). The expiration cycle may be determined individually for a particular user, or an average (e.g., population) expiration cycle may be determined.

A respiratory device having a time-delay for the onset of resistance to low-expiratory pressure may include electronic (e.g., timing) components, including counters, clocks, sensors and the like. In some variations, a respiratory device includes a non-electronic timer, such as a mechanical delay which is initiated upon a change in the direction of airflow from inspiration to expiration. For example, a mechanical delay may comprise a dashpot or damper which prevents one or more of the valves within the device from closing after inhalation. The damper may include a pre-set delay before closing completely. In some variations, opening is substantially undampened.

Operation of the Respiratory Device

The airflow resistor may be oriented in any direction. In one variation, a respiratory device may be used in one nostril in an opposite orientation to a respiratory device in the other nostril, which may alternate through which nostril resistive inspiration or expiration occurs.

In some versions, the respiratory device is shaped so that the direction of the airflow resistor is immediately evident. For example, the respiratory device may be of a different shape or size on one end, or may include a visual indication. In one version, the respiratory device may be shaped so that it fits securely into a respiratory orifice only in one orientation (e.g., so that the airflow resistor inhibits the expiration more than it inhibits inhalation). For example, a flange or other mechanical stop may be used to insure proper orientation, while simultaneously preventing migration of the device further into the respiratory orifice.

In many embodiments, the PEEP-configured device provides some level of resistance to expiration, particularly at low pressure. It may be preferable to have little if any effect on resistance to inspiration, though in some cases, some degree of inspiratory restriction may be beneficial. In some versions of the device, both inspiration and expiration may be inhibited by the airflow resistor.

The device may also be adapted for comfort. Any device placed either in or around the oral cavity or in or around the nose should not be painful, and if possible not very noticeable by the patient. Thus, the holdfast may be shaped to conform to the attachment site in or around the respiratory orifice. In some versions, the holdfast comprises a flexible or shapeable material (e.g., a foam or other soft shape-memory material). In some versions, the entire respiratory device comprises a soft material.

When using devices that feature a foam on the portion of the device that fits within or otherwise communicates with the inside of a nostril, the device may be inserted by the patient or healthcare provider foam end first. It may be helpful to insert a corner of the device into the nostril and then rotate the device into place. The device may then be gently pulled outward (without removing the device from the nostril) so that it rests in the correct position and provides a seal between the periphery of the device and the nasal cavity or nostril.

The user may be instructed to breathe through his/her/its mouth or nose, whichever is more comfortable. If the device is going to be worn by a subject during sleep, the user may be instructed to breathe primarily or relatively primarily through his mouth while he is still awake. This may make the sensation of expiratory resistance and pressure easier to tolerate. It is expected that when the patient goes to sleep, he will revert primarily or at least partly to nose breathing, thus promoting the beneficial effects of the device. The subject devices may also be used with any commercially available device that promotes closure of the mouth during sleep, including but not limited to straps, mouthguards, tape and the like.

In some cases, a nasal cannula or other means of monitoring nasal airflow (such as a thermistor) may be attached, fixed, or non-fixably positioned within or near the device to allow various diagnostic parameters to be measured. In some cases, the nasal cannula or other diagnostic device may be held in place with tape (on the face for example, near the chin or cheek). By attaching the diagnostic device to the device, it is less likely that inadvertent or undesired motion will shift or displace the device while sleeping or otherwise during use. In some cases, the subject device may be extended or otherwise altered or changed to allow the placement of the nasal cannula.

In other cases, an intranasal pressure probe or sensor may be placed beyond the device (deeper within the nasal cavity or nostril) to provide a pressure reading for the airways, nose, and other respiratory pathways.

Furthermore, the device may be adapted so that it is more or less visible to others. In some cases, the device may be configured to be placed high enough within the nostrils to make it difficult for others to see. Furthermore, the device may be of any color and/or pattern that help to camouflage it. In other versions, it may be useful to include colors and patterns that stand out, including ones that are fluorescent or otherwise offer increased visibility during the night or other setting where ambient light is reduced.

In some versions, the respiratory device may be "one size fits all", so that it may be used with any patient (or any patient of approximately the same size), despite differences in shapes and sizes of their nose/nostrils, oral cavity, teeth and other relevant anatomic features. In one version, the devices may conform to a range of sizes, for example "small," "medium," and "large" (or any other appropriate range, such as, e.g., a numerical range). Alternatively, the devices may involve a custom fit of the device or devices to the patient.

Custom fitting may improve patient comfort and potentially improve performance by improving the seal between the device and the patient's oral cavity, mouth, nasal cavity and nostrils, for example. In some versions, custom fitting may involve the placement of a device in warm or cold liquid or air with subsequent placement in the patient's nose or mouth. This process is meant to "prime" the materials in the device (e.g., particularly the materials of the holdfast), so that when the holdfast is secured to the patient, the device permanently assumes a shape or configuration corresponding to a portion of the patients anatomy.

In some cases, the device may be over the counter (OTC) and in other cases, it may require a prescription. Some possible indications for the device will include but not be limited to sleep apnea, snoring and upper airway resistance syndrome. In other cases, the device may be used to improve athletic performance, heart or lung function, or improve oxygenation. In some cases, the devices will be reusable. In some cases, the devices will be disposable after one or more uses. The devices may be modular; for example, at least one component or subassembly of the device may be reusable and at least one component or subassembly may be disposable.

In some version of the devices described herein, an airflow resistor may fit within a larger structure (such as the passageway) so that some airflow through or around the airflow resistor is always allowed. For example, there might be a constant opening between the airflow resistor and the anchor that secures the airflow filter in communication with the passageway. This may ensure that expiratory and/or inspiratory airflow is never completely occluded. In some versions, the airflow resistor comprises a "hole" or opening. As described above, the device may include one or more holes or air leak paths even in the closed position, so that some air may pass through the device even if the holdfast forms a relatively tight seal with the nasal cavity. For example, the airflow resistor (e.g., flap valve) may include one or more holes providing an air leak path. The size of the holes may be configured to allow a predetermined rate of airflow through the holes when a certain pressure is applied (e.g., by the user's breathing). For example holes may be small (e.g., having diameters of 0.030 inches±0.010 inches). In some variations, multiple holes are used.

The devices described herein may create a PEEP effect by differentially changing the resistance to airflow in one direction based on the pressure applied against the device, as described above. For example, in some designs, expiratory airflow is subjected to resistance by the airflow resistor (or valve) until a certain threshold pressure differential or level of airflow is achieved; below that threshold, a more complete closure of the airflow resistor occurs (potentially completely occluding airflow through the device). The desired levels of PEEP are on the order of about 0.1 to about 30 cm $H_2O$ and more preferably about 1 to about 15 cm $H_2O$ pressure. Similarly, the differential resistance may also be triggered at very high pressures across the valve. For example, above a typically high threshold of pressure or level of airflow, the airflow resistor (e.g., valve) may open to decrease the resistance due to the airflow resistor, as when a patient coughs, sneezes, or blows his or her nose.

In some cases, the device may offer a variable resistance that is lower during the start of expiration (to promote comfort and tolerance) and that continues to increase (in a stepwise or more gradual fashion) for the remainder of expiration. In many cases, at the end of expiration, PEEP will be maintained. In still other cases, there will not be PEEP at the end of exhalation. In some respiratory devices described herein, when expiratory airflow and/or expiratory airway pressures fall below a threshold (one that is too low to keep an airflow resistor mechanism open), expiration airflow will be stopped, leading to PEEP. As a result, normal inspiration, normal expiration, and PEEP are accommodated while offering potential benefits to the patient, including clinical benefits.

In some cases, the device may feature a fixed orifice during expiration (e.g., a fixed leak path). Thus, the size of the hole(s) within the airflow resistor remains substantially or significantly equal for all, most or substantially most of the expiratory cycle. Such a device may allow the "average" and peak pressures in the airway to be different during supine positioning, lateral (left or right) positioning and prone position during sleep. Preferred peak airway pressures during exhalation, regardless of positioning, may be between 0.1 to 70 cm $H_2O$, more preferably between 0.5 and 25 cm $H_2O$ and most preferably between 1 and 20 cm $H_2O$ pressure during sleep. Supine pressures may on average be greater than pressures while in lateral and prone positions during sleep.

The optimal level of expiratory resistance or PEEP provided by the device may vary from patient to patient. In some versions, adequate expiratory resistance or PEEP is created to offer the desired benefits, but not providing too much expiratory resistance or PEEP so that the patient preferentially begins breathing (e.g., inspiring and/or expiring) through the mouth. In some cases, the user may test the device or devices while being monitored by a healthcare provider, a camera, a polysomnograph, or any other device that will help to assess the optimal level of resistance or therapy provided by the subject devices. As described in more detail below, the devices described herein may be adjustable. In particular, the threshold pressure for opening the valve during exhalation may be adjustable, for example by the subject or a healthcare provider. In some variations, the threshold pressure for closing the valve may also be adjustable, for example by the subject or a healthcare provider.

The use of an airflow resistor may also alter the inspiratory time:expiratory time ratio (I:E ratio), which is defined as the ratio of inspiratory time to expiratory time. The desired I:E ratio will be between about 3:1 and about 1:10 and more preferably about 1:1 to about 1:4 depending on the needs of the individual patient. In some versions, the desired ratio is approximately about 1:2.

In some versions, the device comprises an insertion, adjustment, or removal mechanism. In some cases, this mechanism involves any appropriate rigid or non-rigid positioner that facilitates removal or positioning of the device. Non-rigid positioners include but are not limited to cables, chains, wires, strings, chains, sutures, or the like. Rigid positioners include knobs, handles, projections, tabs, or the like. A user may grasp or otherwise manipulate the positioner to facilitate insertion, re-adjustment, or removal of the device. Furthermore, various applicators or other insertion devices may be used. For example, a tubular applicator holding a respiratory device adapted for insertion into a nasal cavity may be advanced into the nasal respiratory orifice (e.g., nostril) to insert the respiratory device.

In some cases, the device may be oversized, or larger than the cavity it is inserted into, for example to prop open the nasal valve. Oversizing the device may reduce resistance in one or more direction of airflow. In some versions, the passageway through the device is oversized. In some versions, an outer portion of the device that contacts the respiratory orifice is oversized. Thus, the respiratory device may exert pressure against the nasal cavity of a user. In patients with obstructive sleep apnea or snoring, for example, increasing the size of a respiratory device configured to be inserted into one or more nostrils may prevent the more distal tissues of the airway, tongue, and nasopharynx from being sucked in or closed during inspiration. Moreover, airflow through an oversized passageway may assume a less turbulent flow profile, resulting in a decreased propensity for noise production in the case of snoring, for example. Similarly, the respiratory device passageway may be shaped so as to decrease turbulence of airflow. Likewise, the shape and activity of the airflow resistor may be chosen to minimize turbulence and, therefore, sound or vibration.

In operation, the user may be asked to clean his or her nose, trim or clip his or her nose hairs, and remove all or substantially all nasal mucus or boogers. The device, especially if it is at least partly composed of foam or other deformable material, may be squeezed to reduce its size prior to insertion into the nasal cavity or nostril. In some cases, the deformable material may expand or swell over time, providing a comfortable fit and/or seal. In some cases, water or water vapor may facilitate or expedite said swelling or increase in size. In some cases, water or other liquids may fill in holes within open cell foam, therefore improving seal.

In some cases, an active or inactive ingredient may be added into (or onto the surface of) at least one component of the device. For example, an odorant such as menthol, phenol, eucalyptus, or other fragrance may be used. Alternatively, a lubricant or moisturizer (on the surface of the holdfast, for example) or the like may find use to improve patient comfort, seal, etc. Any commonly or uncommonly used substance or ingredient that is used in over-the-counter and/or prescription healthcare products may find use.

The respiratory devices may be manufactured and assembled using any appropriate method. Representative manufacturing methods that may be employed include machining, extruding, stamping, and the like. Assembling methods may include press-fitting, gluing, welding, heat-forming, and the like.

A holdfast may be attached to the outer portion of the tubular body, particularly the distal region of the tubular body. In many of the exemplary devices described herein, the holdfast is polyurethane foam. The foam may be pre-molded into the appropriate shape, or it may be cut (e.g., die cut, water jet cut, laser cut, etc.) into a ring or other appropriate shape and attached to the tubular body. For example, the foam may be attached via an adhesive (e.g., tape, glue, etc.). In one variation, the foam is cut from a strip of foam that is attached around the tubular body. The foam may be any appropriate size so that the device is secured within a subject's nasal cavity. In some variations, the foam is between about ¼ and ⅛ of an inch thick. The thickness of the foam holdfast may vary around the diameter of the device. For example, the foam holdfast may be thicker at the ends of an elliptical cross-section so that it conforms better to the shape of a subject's nasal cavity, particularly in the region immediately within the subject's nose, past the nares.

Figure 37:
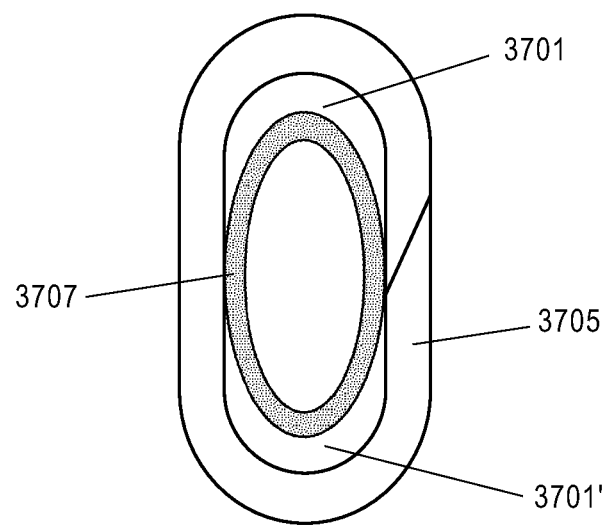
FIG. 37 shows a cross-section through the holdfast of a device as described herein.

FIG. 37 shows one variation of a foam holdfast attached to the outer surface of distal region of the tubular body 3705. The holdfast in FIG. 37 includes two regions that are applied with adhesive. The first region 3701 includes the two narrower ends (e.g., shown as the upper and lower ends) of the tubular body cross-section. In some variations, tapered strips (e.g., cut to be approximately 0.22 inches wide, by approximately 0.6 inches long) are attached at these narrow ends, and then a third strip (approximately 0.22 inches long) is applied on top of them, as shown in FIG. 37. The outer strip 3705 is then trimmed to create a relatively smooth outer surface. This configuration augments the ends of the valve body, which may provide a better nostril fit and seal. In some variations, the outer diameter of the tubular body may also be adjusted (e.g., to make the two end foam pieces 3701, 3701' unnecessary, for example).

As described above, any appropriate foam may be used. For example, Microbaisan 100 foam produced by Lendell Manufacturing is a medical-grade, biocompatible sponge foam that may be used. This foam has a relatively low air permeability.

The holdfast may be adjustable by a practitioner or the user, so that it more comfortably and/or securely fit a particular user. For example, in variations for use within a user's nasal cavity, the holdfast may consist of selectively removable layers of foam that may be removed (e.g., onion-skin like) until a comfortable size is achieved. In some variations, the layers may be coded (e.g., color coded, numbered, etc.) to indicate each "level" of holdfast. Thus, once a user determines a particular configuration for the holdfast that comfortably fits his nose, he may easily set each subsequent device to that configuration.

Figure 38:
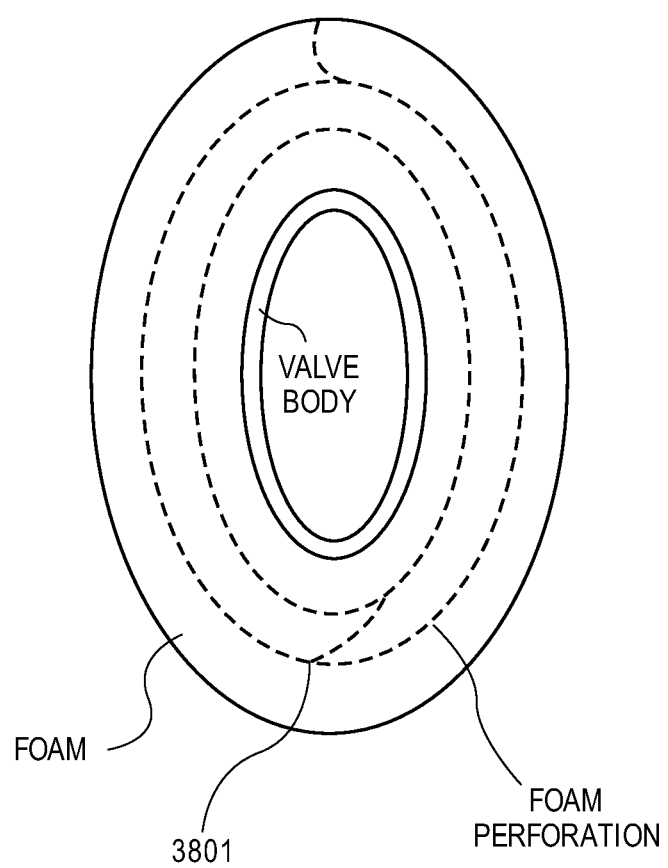
FIG. 38 shows one variation of an adjustable holdfast, as described herein.

FIG. 38 illustrates one variation of an adjustable holdfast, as described herein. In FIG. 38, foam surrounds the outer surface of the tubular body. The foam is divided up into layers, as shown by the dotted lines. Layers may be formed either by applying the foam in layers, or by cutting a relatively thick layer of foam into different layers 3801 (e.g., perforating the foam by laser, etc.). Thus, the shape of the holdfast can be changed by removing one, a portion of one, or multiple layers of foam from the device. For example, in FIG. 38, the outermost layer of foam may be removed by peeling the layer off in a clockwise direction, and the second layer may be removed by peeling the layer off in a counterclockwise direction. Changing the direction of removing each layer may prevent unintentionally removing too much of the holdfast.

Figure 39A:
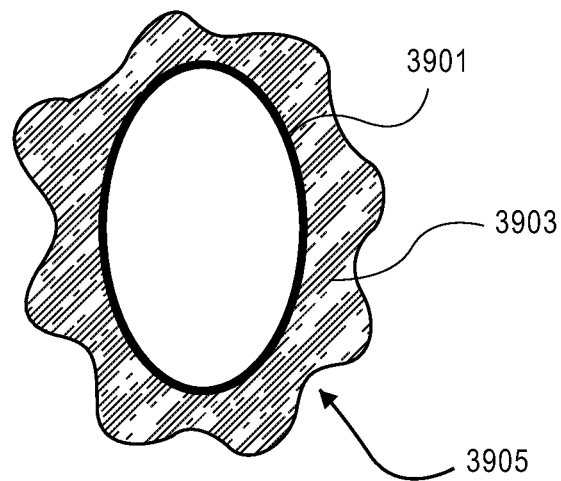
FIGS. 39A and 39B show cross-sections through a holdfast of a device configured for use within a subject's nose.
Figure 39B:
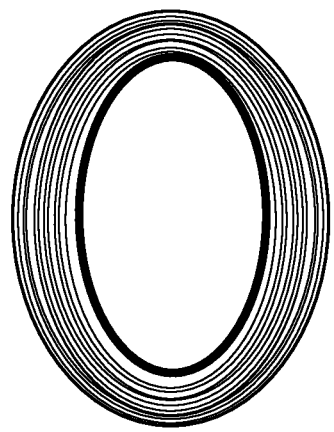

The holdfast may also be configured to expand to fit within the subject's nasal cavity. Nasal tissues may swell during sleep or when a subject is lying prone. This swelling may allow the user to insert a respiratory device that is relatively loose fitting before lying down, permitting easier breathing. Thus, before a subject falls asleep the more loosely fitting device can help the user breath more easily, and any nasal swelling that occurs would gradually help the subject sleep better. FIGS. 39A and 39B illustrate a device configured to take advantage of this swelling.

In FIG. 39A, the holdfast 3903 surrounds the outer surface of the passageway-forming body 3901, and consists of a soft, biocompatible material that has a scalloped shaped profile. When the device is inserted into a subject's nostril, there may initially be gaps 3905 that form between the holdfast and the walls of the subject's nasal cavity. As the walls of the nostril swell (e.g., during sleep, etc.), and the inner diameter of the nostril decreases, these gaps may disappear, so that the device is comfortably sealed within the nasal cavity, as shown in FIG. 39B. Swelling and reduction of the inner diameter of the nostril may also compress the holdfast (e.g., a compliant foam holdfast), advantageously reducing the air permeability of the holdfast.

In some variations, the foam may be configured to expand within the nasal cavity. As mentioned briefly above, the foam may be configured to swell because of the increased moisture (e.g., in exhaled air), thereby enhancing fit or the seal within the nasal cavity. In some variations, the holdfast is configured to expand in the presence of the subject's body heat. Thus, heat transfer from the subject to the device causes the holdfast to swell and thus better fit the nostril.

Although most of the devices described herein are configured for nasal use, devices may also be configured for oral use (e.g., within the oral cavity). For example, an oral device for inducing positive end-expiratory pressure may be secured in communication with a oral cavity (e.g. over, at least partially over, within, or at least partially within the subject's mouth) and may include a passageway, an airflow resistor in communication with the passageway, wherein the airflow resistor is configured to have a non-zero threshold pressure for opening during expiration so that the airflow resistor is closed during expiration when the pressure across the airflow resistor is below the threshold pressure for opening, but the airflow resistor opens during expiration when the pressure across the airflow resistor exceeds the threshold pressure for opening during expiration; and a holdfast configured to secure the airflow resistor in communication with the oral cavity but not the subject's nose in some cases.

In some variations, the holdfast is configured as a mouthpiece that fits at least partially within the subject's mouth. An oral respiratory device may extend the jaw (e.g., mandible) and/or the tongue to further facilitate respiration. These oral respiratory devices may also include one or more valves to help regulate respiration. In general, these devices may fit within or partially within the subject's oral cavity and displace or extend the subject's mandible and/or tongue, as well as provide a pathway for airflow that may be regulated by one or more valves or airflow resistors. Any portion of the device may also extend out from the subject's oral cavity.

Figure 40:
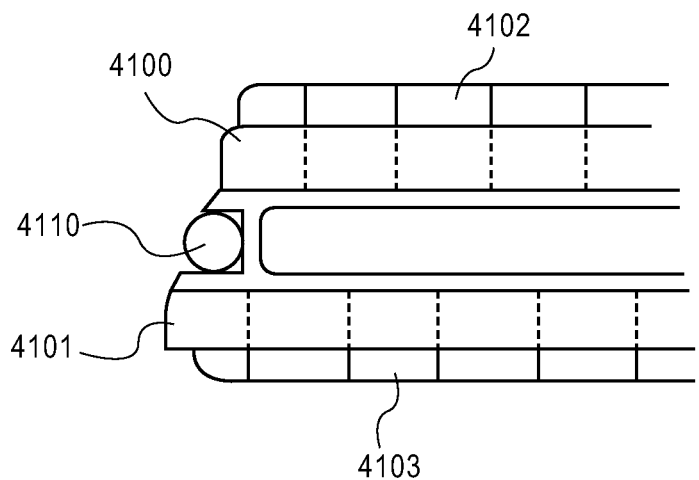
FIG. 40 shows one variation of an oral device including mandible displacement, as described herein.

FIG. 40 shows one variation of an oral device that may allow the benefits of expiratory resistance (with or without PEEP) in addition to the benefit of advancing the mandible (which increases the size of the upper airway). Upper jaw anchor 4100 and lower jaw anchor 4101 serve to secure the device to the upper jaw 4102 and lower jaw 4103 respectively in such a manner that the lower jaw 4103 (mandible) is pushed forward while slightly opening the jaw. The device offers an opening in or around the space between the jaws through which air may flow, and a resistor 4110 may be placed in this location. At least some of the subject's airflow must pass through the resistor in one or more directions. Any resistor, including those described herein, may be used, including resistors that offer preferential expiratory resistance, with or without PEEP. Examples of additional airflow resistors that may be used with this device are included in U.S. patent application Ser. No. 11/298,640, filed Dec. 8, 2005 and U.S. Provisional Patent Application titled "NASAL RESPIRATORY DEVICE," filed May 23, 2006, each of which was previously incorporated by reference in its entirety. The device may be made of any appropriate hard or soft materials, including those described herein. In some variations, the degree of lower jaw advancement may be adjusted.

Figure 41:
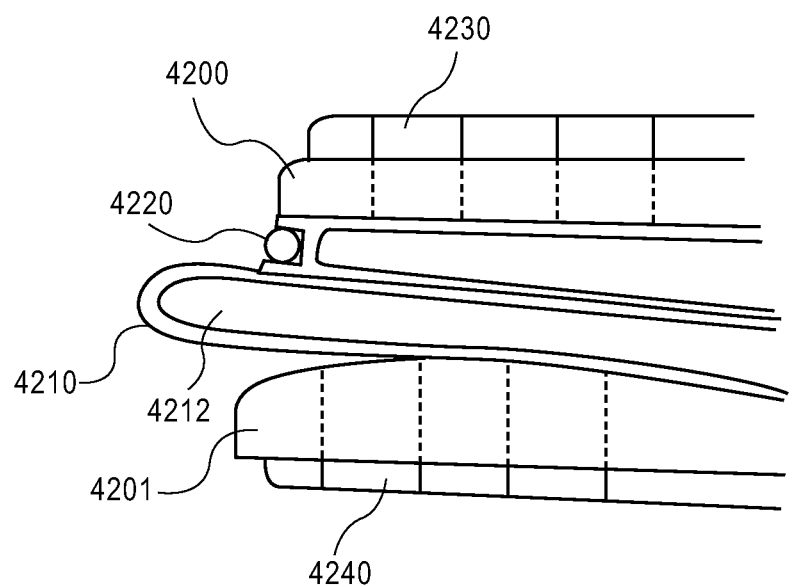
FIG. 41 shows another example of an oral device as described herein.

FIG. 41 shows another variation of an oral device that may provide expiratory resistance (with or without PEEP) and may advance the tongue to an anterior position (which increases the size of the upper airway) through the use of suction. In FIG. 41, upper jaw anchor 4200 and lower jaw anchor 4201 serve to secure the device to the upper jaw 4230 and lower jaw 4240 respectively, and suction cavity 4210 is positioned between jaw anchors 4200 and 4201 to receive and retain the tongue 4212 during use. Thus, the tongue may be pulled (via the suction) toward the anterior direction (e.g., out of the mouth). The device may have an airflow opening at any location between jaw anchors 4200 and 4201, where resistor 4220 may be positioned. At least some of the subject's airflow must pass through the resistor in one or more directions. Any appropriate resistor may be used, including those described above (e.g., resistors that offer preferential expiratory resistance, with or without PEEP). The device may be made of any appropriate materials, particularly those suitable for oral use, including hard or soft materials. In some embodiments, the devices in FIG. 40 may be coupled with some lower jaw advancement as described in FIG. 41.

In some variations, it may also be desirable to occlude the nostrils of a user wearing an oral device (including the mandibular or tongue displacement devices described above). Thus, a second device may be used in conjunction with an oral device to plug the nose so that airflow is restricted to the mouth. In some variations, the oral device may include a nostril-occluding region integral to the oral device. Restricting airflow to the subject's mouth may enhance the effects of any of the various oral resistance devices (with or without PEEP) described herein.

Uses of the Respiratory Devices

The respiratory devices and methods described herein may be used for a variety of therapeutic and non-therapeutic purposes, particularly uses in which PEEP would be helpful. A description of some of these uses is given below. The respiratory devices and methods described herein may be used in other ways as well, and these examples are not to be considered exhaustive.

Generally, the respiratory devices described herein may improve the respiratory and cardiovascular function of a person in need thereof (e.g., a patient). Thus, these respiratory devices may be used therapeutically, for example, to cure, treat or ameliorate the symptoms of a variety of medical disease states. Furthermore, the respiratory devices may be useful in generally improving the health and well being of any person.

Disease states which may be treated by the devices and methods described herein include but are not limited to: heart failure (right-sided and/or left-sided), COPD, pulmonary edema, sleep apnea (obstructive and/or central), sleep-disordered breathing, Cheyne-Stokes respiration, insomnia, snoring and other sleep disorders, asthma, bronchomalacia, acute lung injury, ARDS, cystic fibrosis, hypoxemic respiratory failure, gastroesophageal reflux disease, hiatal hernia, heartburn, hypertension, myocardial infarction, arrhythmia, cardiomyopathy, cardiac valve disease (either stenosis or regurgitation of the mitral, aortic, tricuspid, or pulmonic valves), stroke, transient ischemic attack, increased cerebral pressure, a variety of inflammatory diseases, and degenerative neurologic conditions. Moreover, the devices may be beneficial for patients being weaned off mechanical ventilation, as well as post-operative patients.

The increased pressure within the airways may reduce the amount and frequency of pulmonary edema, a common consequence of heart failure. Afterload and preload on the heart may also be affected; for example, afterload and preload may be decreased in patients with heart failure. Filling pressures may be increased or, more likely, decreased. Decreasing filling pressure may potentially benefit patients with failing hearts. Gas exchange may improve in many cases, leading to increases in $pO_2$ and decreases in $pCO_2$. In some cases, the level of $pCO_2$ may actually increase or become more stable and less likely to fluctuate. This increase in the stability of $pCO_2$ levels may lead to profound benefits in patients with central sleep apnea and in patients with Cheyne-Stokes breathing, for example. Oxygen saturation levels may improve. Oxygen desaturations which may result from apneas or hypopneas may no longer drop as far. For example there may be fewer oxygen desaturations to the 80-89% range. Fewer oxygen desaturations may drop below 90%. Duration of desturations may also be reduced. The use of the device to reduce oxygen desaturations (perhaps leading to performance enhancement) while awake or asleep may represent a viable market opportunity for the device.

In some cases, the use of a expiratory resistor will interfere with loop gain, and will thus promote more stable breathing. In other cases, the device will reduce the amplitude, duration, and frequency of snoring.

Any location within the body that is exposed to respiratory airflow (including but not limited to the upper airway, trachea, bronchi, nasopharynx, oropharynx, nasal cavity, oral cavity, vocal cords, larynx, tonsils and related structures, back of the tongue, sinuses, and turbinates) may benefit from the increased airway pressure and increased duration of expiratory airflow. In some cases, there will be a reduction in swelling and edema in these locations, leading to increased diameters of the airways and conduits in which the airflow passes. This leads to less of a tendency for these structures to collapse upon inhalation. Moreover, these structures may be less prone to create noise on inspiration or expiration, thereby reducing the quantity and/or quality of snoring. Put another way, the reduction of edema in the airways may make it less likely that these structures will collapse and may reduce the volume and frequency of snoring, apnea, or hypopnea. Furthermore, reduction in swelling and edema and improved lymphatic flow due to these positive pressures may reduce nasal congestion, inflammation, and sinusitis for example.

The respiratory device may also increase lung compliance. For example, lung compliance may increase partly if fluid which might otherwise be in the lung and alveoli is driven away by the increased airway pressure. This increased lung compliance may make it easier to breathe and may require less effort and force on the part of the patient to displace the diaphragm a certain distance to achieve a certain tidal volume. Moreover, increased lung compliance may decrease the pressure differential between the alveoli and mouth. As this pressure differential decreases, it becomes less likely that an inhalation attempt will induce a collapse of the upper airway. Thus, an increase in lung compliance may herald a reduction in the frequency or severity of obstructive sleep apnea or hypopnea episodes. Similarly, snoring frequency and severity (volume) may be reduced for similar reasons.

The respiratory device may also improve ejection fraction. This effect may be mediated via increases in intra-thoracic pressure and alterations in transmural pressures and the beneficial effects on preload and afterload on the failing heart. In addition to left-sided benefits to the heart, there may also be benefits afforded to the right side of the heart. Improving ejection fraction with the respiratory devices described herein may result in positive short- and long-term changes to the energetics and biologic properties of the heart tissue. Some of these positive changes may mimic the positive remodeling changes seen in hearts treated with various complicated cardiac support devices such as those developed by Acorn Cardiovascular (St. Paul, Minn.) and Paracor Medical (Sunnyvale, Calif.). These expiratory resistors use the patient's own intra-thoracic pressure to "support" the patient's heart. Moreover, because the support potentially provided by the respiratory devices described herein is not limited to just the ventricle, it may support the atria, which can also be severely affected by heart failure and other cardiac or pulmonary diseases. There may be reductions in left ventricular and left atrial sizes, both in the shorter and longer term. Furthermore, cardiac sympathetic activation may be reduced, and cardiac output may be increased or decreased depending on the nature of the resistance provided.

There are a variety of other beneficial effects of enhanced expiratory resistance and increases in intra-thoracic pressure that may be achieved with the respiratory devices described herein. Examples include decreased heart rate and blood pressure. There may be a reduction in the number of arrhythmias, including but not limited to atrial/supraventricular and ventricular fibrillation, atrial/supraventricular and ventricular tachycardias, heart block, and other common arrhythmias. Thus, the respiratory devices described herein may also reduce the incidence of sudden cardiac death and other cardiac disorders. Furthermore, coronary perfusion may be expected to increase. Further, expiratory resistance and increased intra-thoracic pressures may lead to improvements in gastroesophageal reflux disease (i.e., heartburn), gastritis, Barrett's esophagus, esophageal cancer, hiatal hernia, and other causes of diaphragmatic hernia. This effect may be mediated by the compression of the esophagus located within the thorax due to the increased intra-thoracic pressures. As a result, food and other stomach contents may no longer be able to reflux superiorly into the esophagus, which is otherwise common when patients are lying down. Furthermore, hernias (primarily hiatal) may be reduced and pushed back into the abdomen by the increased intra-thoracic pressure. The use of these respiratory devices may have beneficial effects on other gastroenterologic conditions beyond those already described.

Cardiac valve disease, including but not limited to mitral, tricuspid, pulmonic and aortic regurgitation, and mitral, tricuspid, pulmonic and aortic stenosis may also benefit from the respiratory devices described herein. In particular, the respiratory device may effect mitral regurgitation and may help prevent further annular dilatation (a byproduct of heart failure and generalized heart dilation).

Use of the respiratory devices described herein will result in a reduction in respiratory rate, which may be very helpful in diseases such as COPD, asthma, hyperventilation, and anxiety disorders including panic attacks, among others. The ratio of inspiratory time to expiratory time (I:E ratio) may be decreased with the device. Tidal volumes may increase as well. For example, in COPD, the increased resistance may facilitate improved expiratory function. This may also allow the patient to benefit from larger tidal volumes and increased minute ventilation. In still other cases, respiratory rate may be increased and in other cases, minute ventilation may be decreased.

The amount of PEEP (or resistance generated by the device) may overcome some, or all, of the intrinsic PEEP that is common in patients with COPD. In patients with COPD or other pulmonary disorders, or even patients without disease, gas exchange may improve. In this case, gas exchange refers to the removal of $CO_2$ from the body and addition of $O_2$ into the blood stream from inspired air. Thus, $pO_2$ may increase and $pCO_2$ may decrease, particularly in patients with COPD, but more generally in all patients treated with the device. Moreover, oxygen saturation may increase, reflecting an increase of oxygen binding to hemoglobin.

Other benefits offered by the respiratory device may include a reduction in diaphragm fatigue and improved efficiency of the accessory muscles of inspiration. This may make breathing significantly easier in patients with pulmonary disease, and more specifically COPD and cystic fibrosis.

As previously mentioned, the respiratory devices described herein may decrease respiratory rate. It has been shown that slowed breathing techniques can lead to a reduction in blood pressure. Thus, the device may reduce blood pressure in a patient, including patients with hypertension (systemic and pulmonary). The reduction in blood pressure may be systolic and/or diastolic. Reductions in blood pressure may be on the order of 1-70 mm Hg systolic or diastolic. This may bring the patient to normal (<140/80 mm Hg) or near normal (<160/100 mm Hg) levels. In patients who are being treated for hypertension, the device could be used as an adjunctive therapy to drugs or as a stand-alone therapy in some patients. In some versions, a respiratory device as described herein may be used for short periods (minutes, hours, or longer) over a span of days to weeks to months to offer longer term benefits for weeks or months after the cessation of therapy. Treatments may last 15 seconds to 24 hours and may be repeated over a regular or irregular interval, for example, on the order of hours to days. The devices may be worn at night or day, while awake or during sleep, to slow respiratory rate. A reduction in blood pressure and/or heart rate may be seen while the device is in place, or after the device has been removed. This may be due to hormonal influences whose effects last longer than the period in which the device is in place. More specifically, the device may work though either a sympathetic or parasympathetic pathway.

Expiratory resistance may also prolong expiratory time, which may reduce the respiratory rate. Thus, the devices described herein may be used to reduce respiratory rate. This may have benefits in treating insomnia, since it may promote a sense of relaxation in the user, through increased parasympathetic stimulation, decreased sympathetic simulation, and/or other hormonal and non-hormonal effects. This may also promote a sense of well being or relaxation that may allow the user to fall asleep easier and quicker and improve sleep quality and quantity. Thus, the respiratory devices described herein represent a novel non-pharmacologic method of treating insomnia and promoting relaxation. The device may be used throughout the day and/or night to promote said relaxation and well being.

The respiratory devices described herein may also be used to treat or ameliorate disorders characterized by ineffective, non-productive, or otherwise disturbed inspiration (including but not limited to obstructive sleep apnea or restrictive pulmonary disease). For example, with the device in place, a patient may be more likely to have slightly elevated lung volumes after exhalation. Put another way, more air than normal may be present in the lungs after exhalation when using some versions of the device. Fewer alveoli may be collapsed; thus inhalation may be easier because it will require less effort to re-open the alveoli during the subsequent breath. Moreover, pulmonary congestion and pulmonary edema may also be reduced, so compliance may be improved. As a result, it may require less effort for patients to inhale. It follows that a smaller pressure differential (between the alveoli and the mouth) will be required. The smaller the pressure differential, the less likely that the patient's conducting airways (including the upper airways and pharyngeal tissues) will collapse, thus reducing the likelihood of obstructive sleep apnea, hypopnea, and snoring.

Infectious diseases may also benefit from the respiratory devices described herein. These diseases include but are not limited to pneumonia (community and hospital acquired), tuberculosis, bronchitis, HIV, and SARS.

The respiratory devices may also be useful in pulmonary or cardiac rehabilitation. For example, the device may find use in patients with chronic pulmonary disease including but not limited to chronic bronchitis, emphysema, asthma, pulmonary fibrosis, cystic fibrosis, and pulmonary hypertension. Alternatively, the devices may benefit patients with cardiac disease, including but not limited to: angina, myocardial infarction, right or left sided heart failure, cardiomyopathy, hypertension, valve disease, pulmonary embolus, and arrhythmia.

Patients with obesity may also benefit from the use of the respiratory devices described herein. Obesity can contribute to exercise intolerance partly because it increases the metabolic requirement during activity and alters ventilatory mechanics by reducing functional residual capacity (FRC)

and promoting atelectasis. Obesity may also reduce cardiac reserve, since a higher than normal cardiac output response is required during physical activity. This in turn may cause systemic hypertension, which increases left ventricular afterload. Thus, the device, through its potential reduction in atelectasis and beneficial effects on FRC, cardiac output, and blood pressure may be useful in patients with obesity.

It has been suggested that expiratory positive airway pressure (as induced by the subject devices) may increase neural drive to the muscles that serve to maintain upper airway patency. Furthermore, FRC increases may improve length-tension relationships of the inspiratory muscles, allowing inspiratory pressures to decrease. This reduction of inspiratory pressure would thus make it less likely for the upper airway to obstruct, presumably due to a reduction in the transmural pressure gradient. As previously suggested, positive end expiratory pressure may improve ventilation-perfusion relationships which may improve oxygen saturation.

Furthermore, it is known that the upper airway partially or completely occludes during the expiratory phase of the breaths preceding an occlusive apnea. It is this narrowing of the upper airway at end-expiration that sets the stage for total occlusion during the next inspiration as subatmospheric pressures are generated within the airway. Expiratory positive airway pressure may therefore prevent airway narrowing during expiration, thus reducing the propensity toward total occlusion during inspiration. The phenomena of lung hysteresis may also provide therapeutic benefit.

The subject devices are also expected to improve sleep quality, duration and architecture. For example, there may be increased REM, slow wave, deep and/or stage 3 and 4 sleep and reduced light and/or stage 1 and 2 sleep. Sleep fragmentation may be improved with reduced transitions between sleep stages. There may be fewer arousals and/or awakenings. Subjects may experience REM or slow wave sleep rebound when the device is used. Subjects may have reduced central sleep apnea including central sleep apneas associated with sleep onset. Furthermore, subjects may experience more restful sleep and may awake more refreshed.

The respiratory devices may also be used by athletes, for example, during both aerobic and non-aerobic activities, partially because of the potentially beneficial direct effects on the heart and on gas exchange. In some versions, the respiratory device may be oversized, to increase the amount of inspiratory airflow, potentially increasing the amount of oxygen transmitted to the lungs for gas exchange.

The respiratory devices described herein may also be used for therapeutic and non-therapeutic effects on sleep. Sleep quality may be improved, with more slow-wave sleep, fewer arousals, and improved REM sleep. The user may have more productive sleep and may be less tired during the day. Furthermore, the beneficial effects of the device may extend beyond the period of use, and into the daytime as well, even when the device's use is limited to the night (e.g., when the user is sleeping). In some cases, sympathetic discharge may be reduced and/or parasympathetic discharge may be increased. Thus, the device may have positive benefits on the autonomic nervous system. This may offer beneficial systemic effects as well as local effects, some of which have already been described.

The respiratory devices described herein may also be used in other locations besides the nasal and oral cavities. Indeed, any location in the body that serves as an entry or exit location for respiratory airflow or serves as a conducting airway or conduit for airflow may benefit from the use of the devices described herein. For example, a device may be used within, on the external surface of, or near a stoma site (e.g., for use in a patient after a tracheostromy). Alternatively, devices may be adapted for use in ventilatory circuits within ventililators and other positive pressure breathing means (invasive and non-invasive) and in portable breathing devices such as Ambu-bags and the like.

Inflammation (which is present in a variety of disease states) may also be reduced using the respiratory device, possibly via the aforementioned parasympathetic or sympathetic mediated effects and/or effects of the vagus nerve and its stimulation. The treatment of any condition mediated by an inflammatory cytokine cascade is within the scope of the devices and methods described herein. In some embodiments, the respiratory device is used to treat a condition where the inflammatory cytokine cascade is affected through release of pro-inflammatory cytokines from a macrophage. The condition may be one where the inflammatory cytokine cascade causes a systemic reaction, such as with septic shock. Alternatively, the condition may be mediated by a localized inflammatory cytokine cascade, as in rheumatoid arthritis. Examples of conditions which may be usefully treated using the respiratory devices described herein include, but are not limited to: appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, diabetes, ankylosing spondylitis, Berger's disease, Retier's syndrome, or Hodgkins disease.

Furthermore, the respiratory devices and methods of using them may be used by or applied to a variety of different types of animals. Representative animals with which the methods and devices find use include, but are not limited to: canines; felines; equines; bovines; ovines; etc. and primates, particularly humans. The respiratory devices described herein may also be packaged for use. For example, the respiratory devices may be packaged individually or as a set (e.g., in sets of pairs, particularly in variations in which an individual device is used with each nostril). Furthermore, the packaging may be sterile, sterilizable, or clean.

The respiratory devices described herein may also be provided as part of a kit that includes at least one of the devices. Examples of kits may include a respiratory device and instructions for how to use the device. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. The instructions may take any form, including complete instructions on how to use the device, or references, directing a user to using additional sources for instructions (e.g., a website address with which instructions posted on the world wide web).

The device may be used in a clinical study, wherein said clinical study involves comparing sleep data from a patient with the device in place to sleep data from the same patient without the device in place. Any duration of the sleep study shall suffice, from minutes to hours.

The device may be used in patients who have already undergone ENT surgery to help their sleep apnea and/or snoring. This combination of surgery and use of the device may thus reduce AHI, snoring and other relevant parameters. Similarly, the use of weight reduction or sleep position therapy may find use in conjunction this device.

As mentioned above, a respiratory device adapted for use in the nasal cavity may be placed into one or both of a subject's nostrils by medical personnel or by the subject himself. The respiratory device may be secured in place in the subject's nostrils by the interaction between the nostril cavity and the holdfast of the device. The device may be worn during the night or day, while the patient is awake or sleeping. In some cases, the device may be worn around the clock. For example, the device may be worn at night to prevent snoring.

All publications and patent applications cited in this specification are herein incorporated by reference in their entirety, as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An adjustable nasal respiratory device for inhibiting expiration more than inspiration in a sleeping subject when worn in communication with a subject's nose, the device comprising:
   an opening;
   an adjustable airflow resistor in communication with the opening, wherein the airflow resistor is configured to inhibit expiration more than it inhibits inspiration, further wherein the resistance to expiration is adjustable; and
   a holdfast configured to secure the nasal device in communication with the subject's nose without covering the subject's mouth.

2. The device of claim 1 further comprising a nasal airflow monitor to measure nasal airflow.

3. The device of claim 1 further comprising a leak path configured to be open during expiration.

4. The device of claim 1, wherein the holdfast is an adhesive holdfast.

5. The device of claim 1, wherein the holdfast is a shapeable holdfast.

6. The device of claim 1, wherein the airflow resistor is configured to have a non-zero threshold for opening during expiration that is adjustable.

7. A method of treating a disorder using a nasal device configured to be worn by a sleeping subject, the method comprising:
   securing a nasal respiratory device in communication with a subject's nasal cavity without covering the subject's mouth, wherein the nasal respiratory device is secured at least partially within the subject's nasal cavity, further wherein the nasal respiratory device includes an airflow resistor that has a non-zero threshold pressure for opening during expiration;
   opening the airflow resistor from a closed position during expiration through the device when the pressure across the airflow resistor exceeds the threshold pressure for opening during expiration; and
   providing a resistance to expiration through the airflow resistor that is greater than the resistance to inspiration.

8. The method of claim 7 further comprising closing the airflow resistor during expiration through the device when the pressure across the airflow resistor is below the threshold pressure for opening.

9. The method of claim 7, wherein the disorder treated is selected from the group consisting of: respiratory disorders, sleep disorders, gastroenterologic disorders, and cardiovascular disorders.

10. The method of claim 7, wherein the nasal respiratory device is secured at least partially over the subject's nasal cavity.

11. The method of claim 7 further comprising adjusting a resistance to expiration provided by the airflow resistor.

12. A nasal respiratory device for inducing positive end-expiratory pressure that is configured to be worn in communication with a subject's nose, the device comprising:
    an opening;
    an airflow resistor in communication with the opening, wherein the airflow resistor is configured to have a non-zero threshold pressure for opening from a closed position during expiration, so that the airflow resistor opens when the pressure across the airflow resistor exceeds the threshold pressure for opening during expiration, further wherein the airflow resistor provides a resistance to expiration that is greater than the resistance to inspiration, and the resistance to expiration is adjustable; and
    a holdfast configured to secure the entire device in communication with the subject's nose without covering the subject's mouth.

13. A nasal respiratory device for inducing positive end-expiratory pressure that is configured to be worn in communication with a subject's nose, the device comprising:
    an opening;
    an airflow resistor in communication with the opening, wherein the airflow resistor comprises a biased valve having a non-zero threshold pressure for opening during expiration, so that the airflow resistor opens from a closed position during expiration when the pressure across the valve exceeds the threshold pressure for opening, further wherein the airflow resistor comprises a second valve;
    wherein the airflow resistor provides a resistance to expiration that is greater than the resistance to inspiration, and the resistance to expiration is adjustable and a holdfast configured to secure the device in communication with the subject's nasal cavity or both nasal cavities but not the subject's mouth.

14. A nasal respiratory device for inducing positive end-expiratory pressure that is configured to be worn in communication with a subject's nose, the device comprising:
- an opening;
- an airflow resistor in communication with the opening, wherein the airflow resistor comprises a biased valve having a non-zero threshold pressure for opening during expiration, so that the airflow resistor opens from a closed position during expiration when the pressure across the valve exceeds the threshold pressure for opening, further
- wherein the airflow resistor provides a resistance to expiration that is greater than the resistance to inspiration, and the resistance to expiration is adjustable; and
- a holdfast configured to secure the device in communication with the subject's nasal cavity or both nasal cavities but not the subject's mouth.

* * * * *